(12) United States Patent
Deasy et al.

(10) Patent No.: US 12,042,320 B2
(45) Date of Patent: Jul. 23, 2024

(54) MULTI-MODAL, MULTI-RESOLUTION DEEP LEARNING NEURAL NETWORKS FOR SEGMENTATION, OUTCOMES PREDICTION AND LONGITUDINAL RESPONSE MONITORING TO IMMUNOTHERAPY AND RADIOTHERAPY

(71) Applicant: MEMORIAL SLOAN KETTERING CANCER CENTER, New York, NY (US)

(72) Inventors: Joseph O. Deasy, New York, NY (US); Harini Veeraraghavan, New York, NY (US); Yu-Chi Hu, New York, NY (US); Gig Mageras, New York, NY (US); Jue Jiang, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 553 days.

(21) Appl. No.: 17/264,048

(22) PCT Filed: Jul. 30, 2019

(86) PCT No.: PCT/US2019/044166
§ 371 (c)(1),
(2) Date: Jan. 28, 2021

(87) PCT Pub. No.: WO2020/028382
PCT Pub. Date: Feb. 6, 2020

(65) Prior Publication Data
US 2021/0383538 A1 Dec. 9, 2021

Related U.S. Application Data

(60) Provisional application No. 62/712,175, filed on Jul. 30, 2018.

(51) Int. Cl.
*G06K 9/00* (2022.01)
*A61B 6/00* (2006.01)
(Continued)

(52) U.S. Cl.
CPC .......... *A61B 6/5211* (2013.01); *G06T 3/4053* (2013.01); *G06T 5/50* (2013.01);
(Continued)

(58) Field of Classification Search
None
See application file for complete search history.

(56) References Cited

U.S. PATENT DOCUMENTS

2009/0116710 A1  5/2009 Futami et al.
2015/0317792 A1  11/2015 Wiemker et al.
(Continued)

FOREIGN PATENT DOCUMENTS

| CN | 104484886 A | 4/2015 |
| CN | 106373109 A | 2/2017 |
| WO | WO-2017/223560 A1 | 12/2017 |

OTHER PUBLICATIONS

Jiang et al. ("Multiple resolution residually connected feature streams for automatic lung tumor segmentation from CT images", published online Jul. 23, 2018 (Year: 2018).*
(Continued)

*Primary Examiner* — SJ Park
(74) *Attorney, Agent, or Firm* — Foley & Lardner LLP

(57) ABSTRACT

Systems and methods for multi-modal, multi-resolution deep learning neural networks for segmentation, outcomes prediction and longitudinal response monitoring to immunotherapy and radiotherapy are detailed herein. A structure-specific Generational Adversarial Network (SSGAN) is used to synthesize realistic and structure-preserving images not produced using state-of-the art GANs and simultaneously
(Continued)

incorporate constraints to produce synthetic images. A deeply supervised, Multi-modality, Multi-Resolution Residual Networks (DeepMMRRN) for tumor and organs-at-risk (OAR) segmentation may be used for tumor and OAR segmentation. The DeepMMRRN may combine multiple modalities for tumor and OAR segmentation. Accurate segmentation is may be realized by maximizing network capacity by simultaneously using features at multiple scales and resolutions and feature selection through deep supervision. DeepMMRRN Radiomics may be used for predicting and longitudinal monitoring response to immunotherapy. Auto-segmentations may be combined with radiomics analysis for predicting response prior to treatment initiation. Quantification of entire tumor burden may be used for automatic response assessment.

20 Claims, 52 Drawing Sheets

(51) Int. Cl.
    *G06T 3/4053*     (2024.01)
    *G06T 5/50*     (2006.01)
    *G06T 7/00*     (2017.01)
    *G06T 7/11*     (2017.01)
    *G06T 7/187*     (2017.01)
    *A61B 6/03*     (2006.01)

(52) U.S. Cl.
    CPC .............. *G06T 7/0012* (2013.01); *G06T 7/11* (2017.01); *G06T 7/187* (2017.01); *A61B 6/03* (2013.01); *A61B 6/5229* (2013.01); *G06T 2207/10072* (2013.01); *G06T 2207/20081* (2013.01); *G06T 2207/20084* (2013.01); *G06V 2201/03* (2022.01)

(56) References Cited

U.S. PATENT DOCUMENTS

2017/0200067 A1     7/2017     Zhou et al.
2018/0144465 A1     5/2018     Hsieh et al.

OTHER PUBLICATIONS

Gu et al., "CE-Net: Context Encoder Network for 2D Medical Image Segmentation," Mar. 7, 2019 (Mar. 7, 2019). [retrieved on Nov. 5, 2019]. Retrieved from the Internet: URL: https://arxiv.org/pdf/1903.02740.pdf.

Gu et al., "Multi-Scale Wavelet Domain Residual Learning for Limited-Angle CT Reconstruction," Mar. 4, 2017 (Mar. 4, 2017). [retrieved on Nov. 5, 2019]. Retrieved from the Internet: URL: https://arxiv.org/pdf/1703.01382.pdf.

International Search Report and Written Opinion in International Application No. PCT/US2019/044166, mailed on Nov. 20, 2019.

Jiang et al., "Multiple Resolution Residually Connected Feature Streams for Automatic Lung Tumor Segmentation From CT Images," Jan. 31, 2019 (Jan. 31, 2019). [retrieved on Nov. 5, 2019]. Retrieved from the Internet: URL: https://www.ncbi.nlm.nih.gov/pmc/articles/PMC6402577/pdf/nihms-1009891.pdf.

* cited by examiner

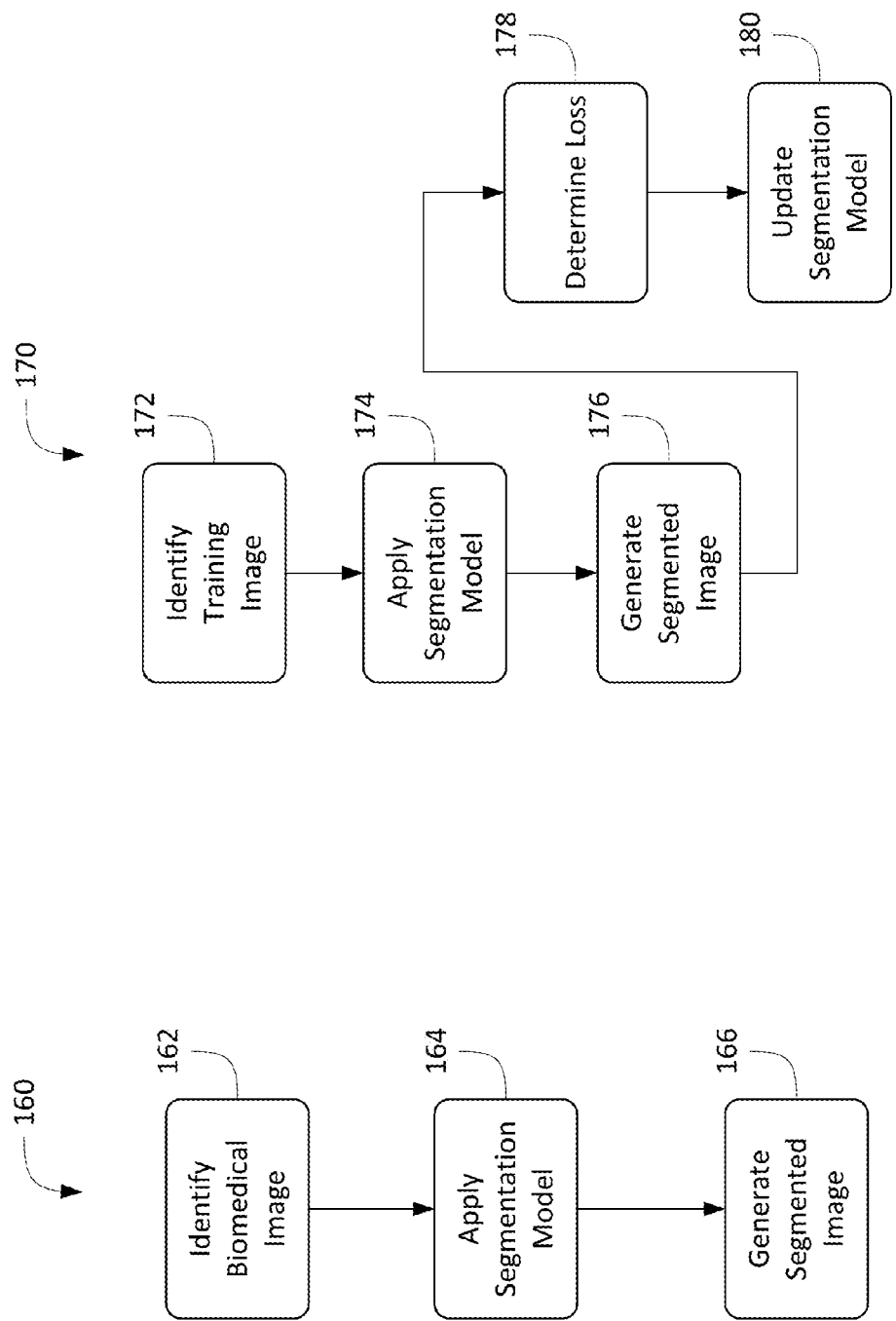

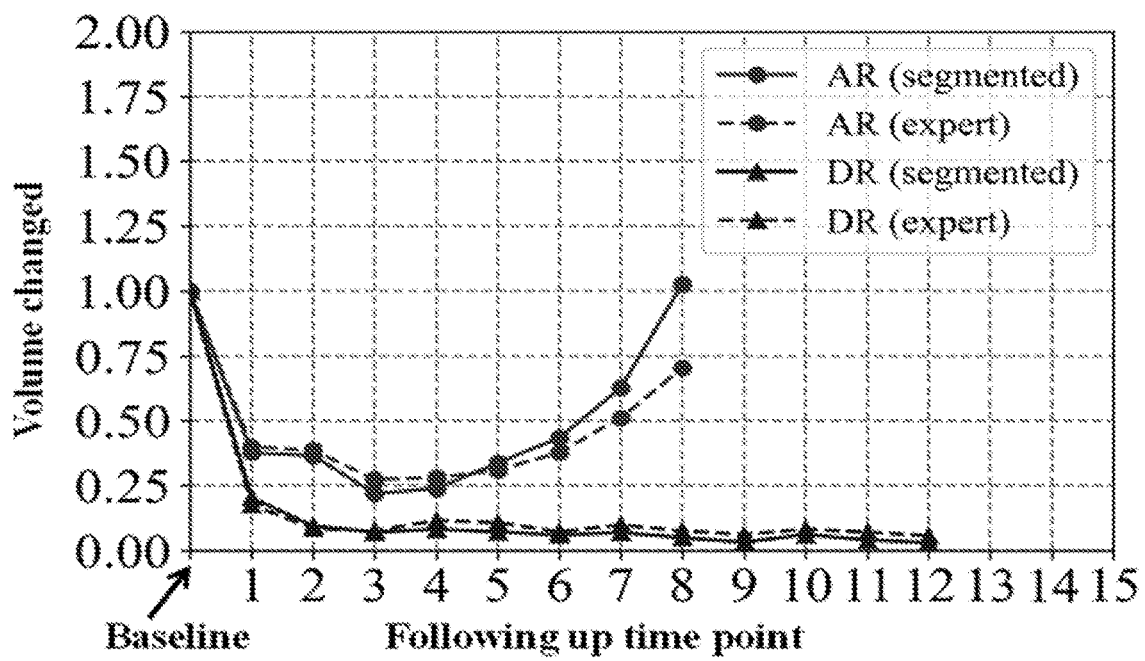
(a) Tumor volume changing plot compared with expert delineation
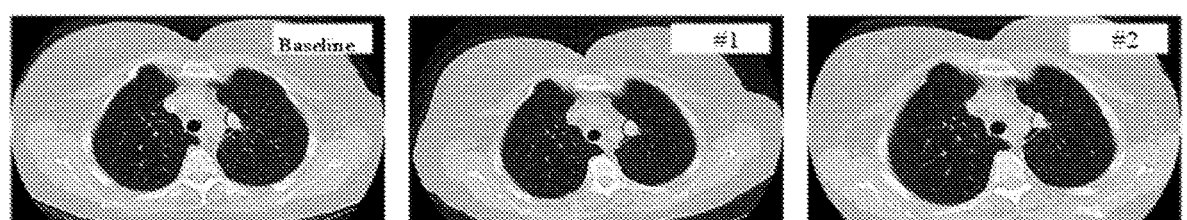
(b) Acquired resistance
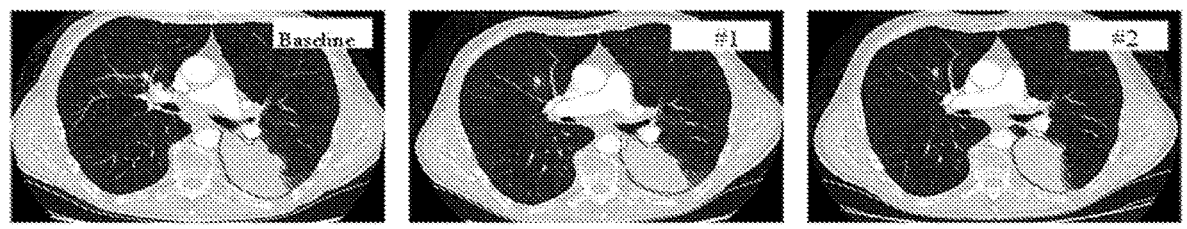
(c) Durable resistance
FIG. 5B

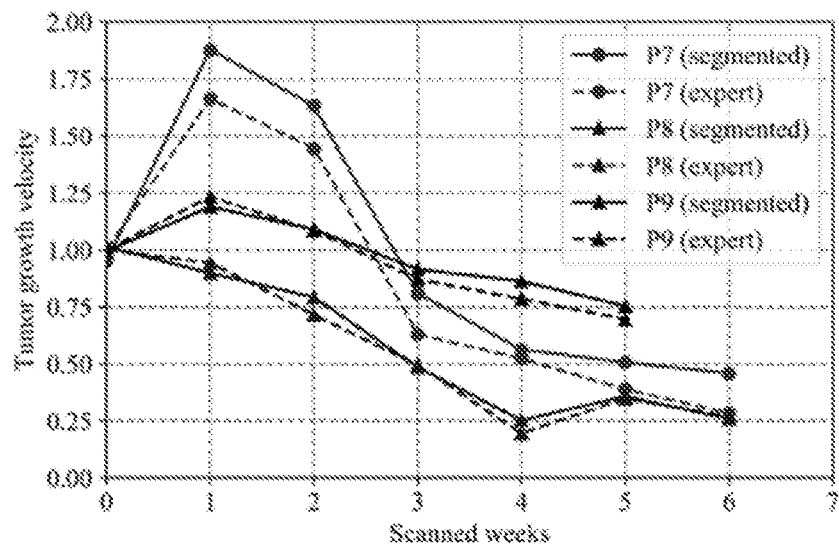
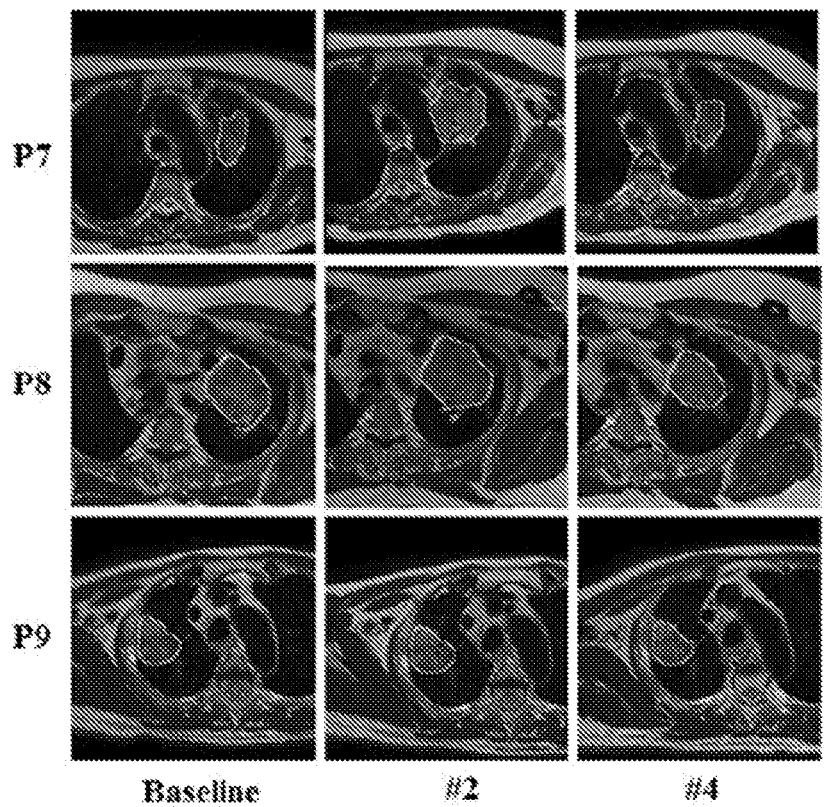
FIG. 14

MULTI-MODAL, MULTI-RESOLUTION DEEP LEARNING NEURAL NETWORKS FOR SEGMENTATION, OUTCOMES PREDICTION AND LONGITUDINAL RESPONSE MONITORING TO IMMUNOTHERAPY AND RADIOTHERAPY

CROSS REFERENCES TO RELATED APPLICATIONS

The present application claims priority under PCT Article 8 to U.S. Provisional Application No. 62/712,175, titled "MULTI-MODAL, MULTI-RESOLUTION DEEP LEARNING NEURAL NETWORKS FOR SEGMENTATION, OUTCOMES PREDICTION AND LONGITUDINAL RESPONSE MONITORING TO IMMUNOTHERAPY AND RADIOTHERAPY," filed Jul. 30, 2018, which is incorporated herein by reference in its entirety.

FIELD OF THE DISCLOSURE

This disclosure generally relates to systems and methods for image segmentation.

BACKGROUND

For some image classification applications, such as those relating to military or medical fields, accurate and reliable segmentation of images can be very important, and may typically be performed by people having specialized training. It is difficult to accurately and reliably segment various objects within images in an automated fashion.

BRIEF SUMMARY

In one aspect, methods, systems, and apparatus disclosed herein are directed to multi-modal, multi-resolution deep learning neural networks for segmentation, outcomes prediction and longitudinal response monitoring to immunotherapy and radiotherapy. In overview, a structure-specific Generational Adversarial Network (SSGAN) is used to synthesize realistic and structure-preserving images not produced using state-of-the art GANs and simultaneously incorporate constraints for multiple structures, shape, location and appearance to produce synthetic images. A deeply supervised, Multi-modality, Multi-Resolution Residual Networks (DeepMMRRN) for tumor and organs-at-risk (OAR) segmentation may be used for tumor and OAR segmentation. The DeepMMRRN may combine multiple modalities (e.g., regular-dose CT & MRI, low-dose or Cone-beam CBCT & MRI) for tumor and OAR segmentation. Accurate segmentation is may be realized by maximizing network capacity by simultaneously using features at multiple scales and resolutions and feature selection through deep supervision. DeepMMRRN Radiomics may be used for predicting and longitudinal monitoring response to immuno/radiotherapy. Auto-segmentations may be combined with radiomics analysis for predicting response prior to treatment initiation. Quantification of entire tumor burden may be used for automatic response assessment.

In another aspect, the present disclosure is directed to multi-modal, multi-resolution deep learning segmentation of tumors and organs at risk. A multi-modal (integrating CT and MR) neural network may be developed and implemented for tumor and normal organs at risk of radiation from radiotherapy treatments. Network architecture may simultaneously combine features from multiple image resolutions and levels, namely low level (edges, and local textures), mid-level (local appearance within and between structures), and high-level (long-range spatial dependencies between structures) for tumor and OAR segmentation. Deep supervision losses may automatically select relevant features at different levels and resolutions for individual structures segmentation. Deep supervision-based dynamic feature fusion may be performed from multiple modalities from different network layers for specific structures. Deep supervision may add an attention mechanism to dynamically weight the deep supervision loss in a pixel-level and channel wise. This mechanism can further faster the training convergence and prevents over-fitting.

In another aspect, the present disclosure is directed to machine learning automated segmentation from small datasets through structure preserving synthetic MRI generation from CT. A multi-modal (integrating CT and MR) generational adversarial neural network may be developed and implemented for synthetic MRI and CT generation. A network architecture may incorporate structure-specific loss integrating location, shape, appearance, and texture to synthesize modality with better soft-tissue contrast (MR) from low-contrast modality namely CT and vice versa. Loss from multiple structures can be integrated to simultaneously learn to accurately transform images from one modality to another. Learned models may produce synthetic MRI or CT images that can be used for: (a) creating large labeled datasets for training machine learning methods in a different modality for unsupervised learning; (b) combining large number of synthetic data with a very small number of labeled data in a different modality for semi-supervised learning; and (c) Combined segmentation using multi-modal datasets for segmentation.

In another aspect, the present disclosure is directed to deep learning-based segmentation for predicting treatment outcomes and longitudinal treatment monitoring. Deep learning may be used to automatically segment 240 patients with longitudinal follow-up (9 week following treatment initiation). Follow up may range from 27 weeks to 117 weeks after treatment initiation with PD-1 checkpoint blockade. Each patient may have tumors ranging from one to twenty individual lesions in each scan. The largest at baseline tumor was segmented and radiomics analysis may be performed for the first 65 patients treated with mono-immunotherapy. The immunotherapy may include pembrolizumab, durvalumab, nivolumab, and atezolizumab, among others.

In other aspects, the present disclosure is directed to systems and methods of segmenting biomedical images using multi-resolution residual neural networks. A computing device having one or more processors may identify an initial tomographic biomedical image derived from a tomographic biomedical imaging scan. The initial tomographic biomedical image may have a first image resolution. The computing device may a segmentation model for biomedical images to the initial tomographic biomedical image. The segmentation model may include a plurality of residual layers. The segmentation model may include a first residual layer to maintain a first residual stream using the initial tomographic biomedical image and feature maps from succeeding residual layers. The first residual stream may carry a first plurality of feature maps. The first plurality of feature maps each may have the first image resolution. The segmentation model may include a second residual layer to maintain a second residual stream using a subset of the first plurality of feature maps of the first residual stream and feature maps from successive residual layers. The second residual stream may carry a second plurality of feature maps to be fed into the first residual stream. The second plurality of feature maps each may have a second image resolution lower than the first image resolution. The segmentation model may include a third residual layer to maintain a third residual stream using a subset of feature maps from at least one of the first residual stream or the second residual stream. The third residual stream may carry a third plurality of feature maps to be fed into at least one of the first residual stream and the second residual stream. The third plurality of feature maps each may have a third image resolution lower than the first image resolution and the second image resolution.

In some embodiments, the computing device may identify a labeled tomographic biomedical image for training the segmentation model. In some embodiments, the computing device may determine a loss metric between the labeled tomographic biomedical image and the segmented tomographic biomedical image. The loss metric may indicate at least one difference between the labeled tomographic biomedical image and the segmented tomographic biomedical image. In some embodiments, the computing device may modify at least one parameter of the segmentation model based on the loss metric.

In some embodiments, the computing device may identify the initial tomographic biomedical image of a first modality. In some embodiments, the computing device may train the segmentation model using training data in. The training data may include a plurality of tomographic biomedical images of the first modality and of a second modality different from the first modality.

In some embodiments, the computing device may identify a plurality of sample feature maps for each residual layer derived from a sample tomographic biomedical image for training the segmentation model. In some embodiments, the computing device may determine, for each residual layer of the segmentation model, a loss metric between a corresponding plurality of feature maps and a corresponding plurality of sample feature maps. In some embodiments, the computing device may modify, for each residual layer of the segmentation model, at least one parameter of the residual layer based on the loss metric for the residual layer.

In some embodiments, the segmentation model may a pooling operator to select in accordance to a pooling operation the subset of feature maps from one of the plurality of residual layers for another of the plurality of residual layers. In some embodiments, the first residual layer may include a set of residual units, a set of aggregator operators, and a convolution operator to process the first plurality of feature maps carried by the first residual stream and at least one of the second plurality of feature maps or the third plurality of feature maps. In some embodiments, the second residual layer may include a set of residual connection units and a set of aggregator operators to process the second plurality of feature maps carried by the second residual stream, the first plurality of feature maps from the first residual stream, and the third plurality of feature maps from the third residual stream.

In some embodiments, the third residual layer may include a set of residual connection units and a set of aggregator operators to process the third plurality of feature maps carried by the third residual stream and at least one of the first plurality of feature maps from the first residual stream and the second plurality of feature maps from the second residual stream. In some embodiments, each layer residual connection units of the third residual layer each may have a first number of the residual connection unit of the third residual layer equal to or larger than a second number of each residual connection unit of the second residual layer.

In some embodiments, the second residual layer may include a set of residual connection units, a set of aggregator operators, and at least one skip aggregator unit to process the second plurality of feature maps carried by the second residual stream. The at least one skip aggregator unit may combine feature maps outputted by a first residual connection unit of the set and by a second residual connection unit of the set of residual connection units.

In some embodiments, the computing device may generate the segmented tomographic biomedical image by combining outputs from the plurality of residual layers of different image resolutions. In some embodiments, the computing device may use the segmented tomographic biomedical image to determine a health metric of a subject from which the initial segmented tomographic biomedical is acquired.

In other aspects, the present disclosure is directed to systems and methods of training models for segmenting biomedical images based on cross-domain adaptations. A computing device having one or more processors may identify a first tomographic biomedical image of a first modality and a second tomographic biomedical image of a second modality. The second tomographic biomedical image may be independent of the first tomographic biomedical image. The computing device may apply, to the first tomographic biomedical image of the first modality, a first synthesis model to translate the first tomographic biomedical image from the first modality to the second modality. The computing device may apply, to the second tomographic biomedical image of the second modality, a second synthesis model to translate the second tomographic biomedical image from the second modality to the first modality. The computing device may determine a synthesis loss among the first tomographic biomedical image of the first modality, the first tomographic biomedical image of the second modality, the second tomographic biomedical image of the first modality, the second tomographic biomedical image of the first modality from the synthesis model. The synthesis loss may indicate at least one difference from translation between the first modality and the second modality. The computing device may apply a first segmentation model for generating segmented tomographic biomedical images to the first tomographic biomedical image of the second modality. The computing device may apply a second segmentation model for generating segmented tomographic biomedical images to the second tomographic biomedical image of the first modality. The computing device may determine, from applying the first segmentation model and to the second segmentation models, an object attention loss indicating at least one difference among layers of the first segmentation model and networks of the second segmentation model. The computing device may modify at least one of the first synthesis model, the second synthesis mode, the first segmentation model, and the second segmentation model based on the synthesis loss and the object attention loss.

In some embodiments, the computing device may apply the first synthesis model to the first tomographic biomedical image. The first synthesis model may include a first generator unit and a first discriminator unit. The first generator unit may translate the first tomographic biomedical image from the first modality to the second modality. The first discriminator unit may be used to determine the synthesis loss for the first synthesis model. In some embodiments, the computing device may apply the second synthesis model to the second tomographic biomedical image. The second synthesis model may include a second generator unit and a second discriminator unit. The second generator unit may translate the second tomographic biomedical image from the second modality to the first modality. The second discriminator unit may be used to determine the synthesis loss for the second synthesis model.

In some embodiments, the computing device may determine the synthesis loss including at least one of an adversarial loss and a cycle consistency loss among the first tomographic biomedical image of the first modality, the first tomographic biomedical image of the second modality, the second tomographic biomedical image of the first modality, the second tomographic biomedical image of the first modality from the synthesis model. In some embodiments, the computing device may determine the object attention loss including at least one of a feature loss, a structure texture loss, a structure shape loss, and a location loss.

In some embodiments, the computing device may determine the object attention loss by identifying a first subset of layers from the first segmentation model and a second subset of layers form the second segmentation model. In some embodiments, the computing device may determine the object attention loss by comparing the first subset of layers of the first segmentation model with the corresponding second subset of layers of the second segmentation model.

In some embodiments, the computing device may determine a first segmentation loss based on the first segmented tomographic biomedical image generated by the second segmentation model from the first tomographic biomedical image and a first annotated image corresponding to the first tomographic biomedical image. In some embodiments, the computing device may determine a second segmentation loss based on the a second segmented tomographic biomedical image generated by the first segmentation model from the second tomographic biomedical image and a second annotated image corresponding to the second tomographic biomedical image. In some embodiments, the computing device may modify at least one of the first segmentation model and the second segmentation model based on the first segmentation loss and the second segmentation loss.

In some embodiments, the computing device may modify at least one of the first synthesis model, the second synthesis mode, the first segmentation model, and the second segmentation model based on a weighted combination of the synthesis loss and the object attention loss. In some embodiments, the computing device may identify the first synthesis model as to be applied to the first tomographic biomedical image based on the first modality and the second modality. In some embodiments, the computing device may identify the second synthesis model as to be applied to the second tomographic biomedical image based on the first modality and the second modality.

In some embodiments, the computing device may identify a third tomographic biomedical image of one of the first modality or the second modality. The third tomographic biomedical image may be independent of the first tomographic biomedical image and the second tomographic biomedical image. In some embodiments, the computing device may apply one of the first segmentation model for the first modality or the second segmentation model for the second modality to the third tomographic biomedical image to generate a segmented tomographic biomedical image. In some embodiments, the computing device may use the segmented tomographic biomedical image to determine a health metric of a subject from which the initial segmented tomographic biomedical is acquired.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 1O and IP are flow diagrams of example methods of segmenting biomedical images using multi-resolution residual neural networks;

Figure 4A:
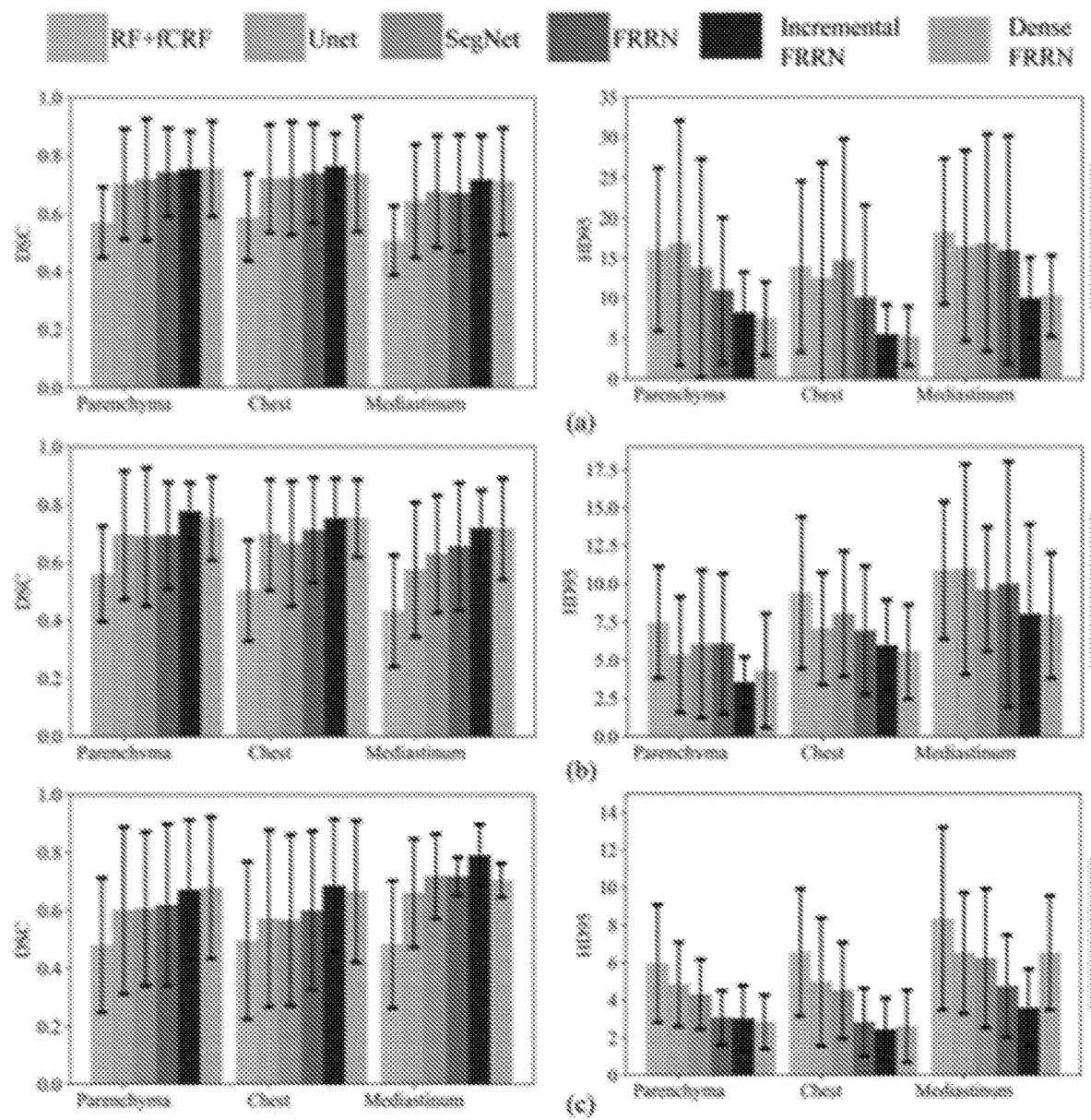
FIG. 4A is a graph showing segmentation accuracy of analyzed methods using (a) TCIA, (b) MSKCC, and (c)
Figure 4B:
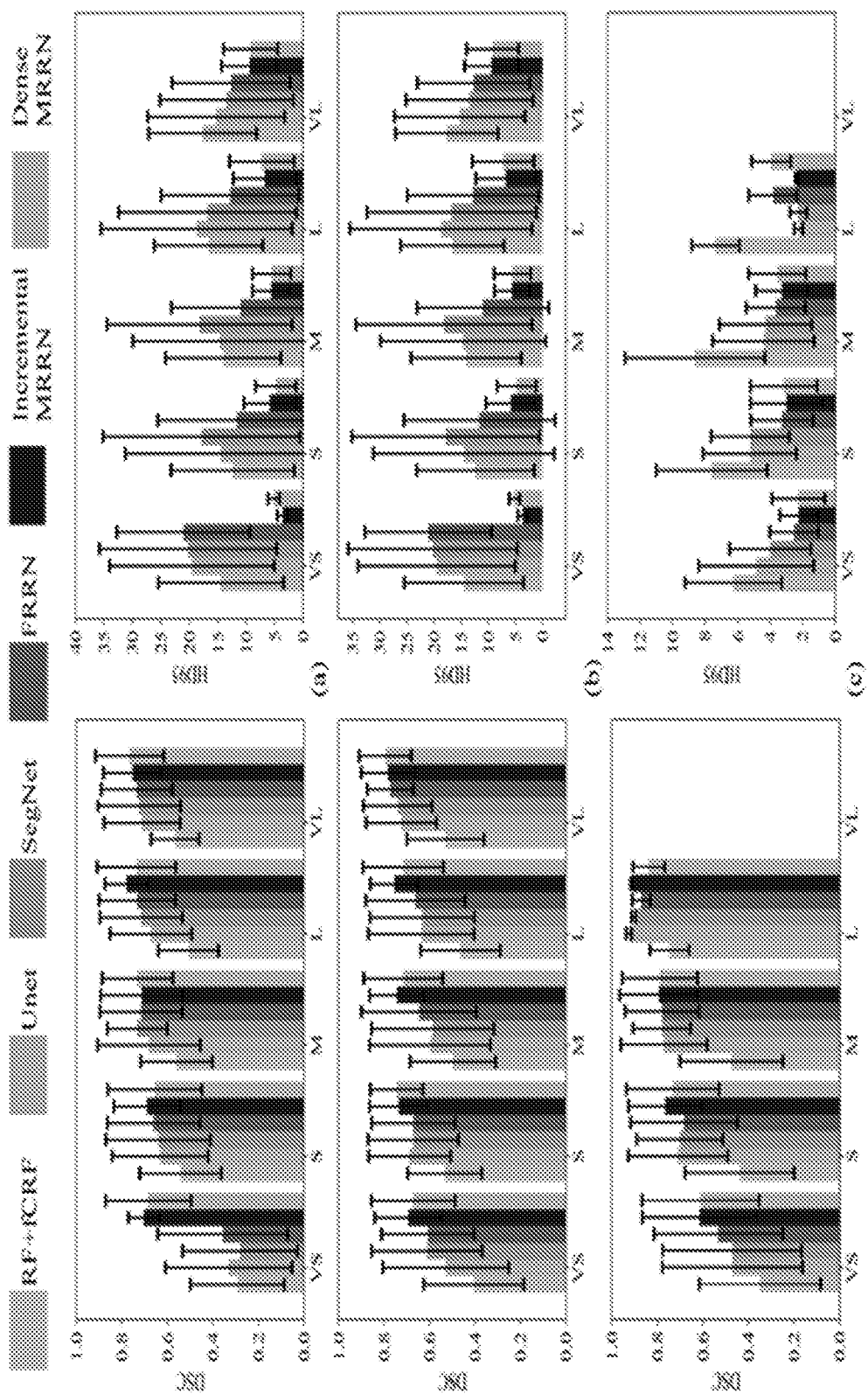
Figure 4C:
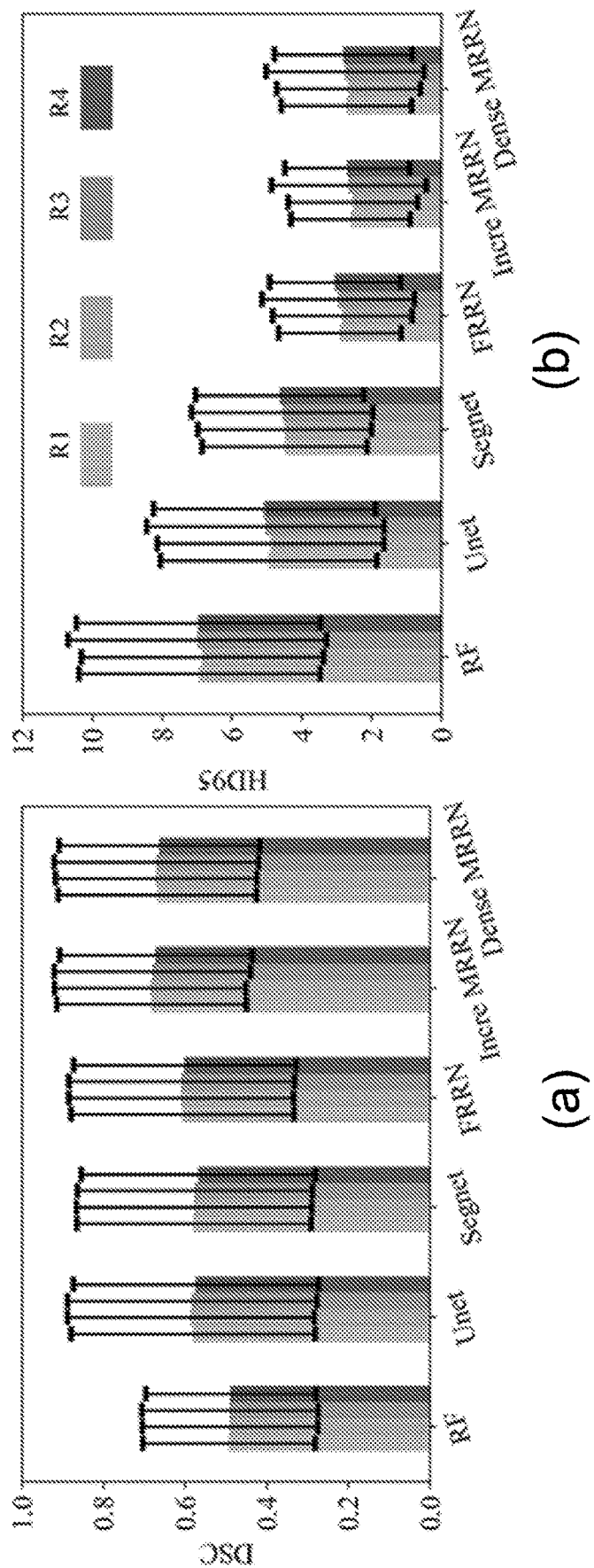
Figure 5A:
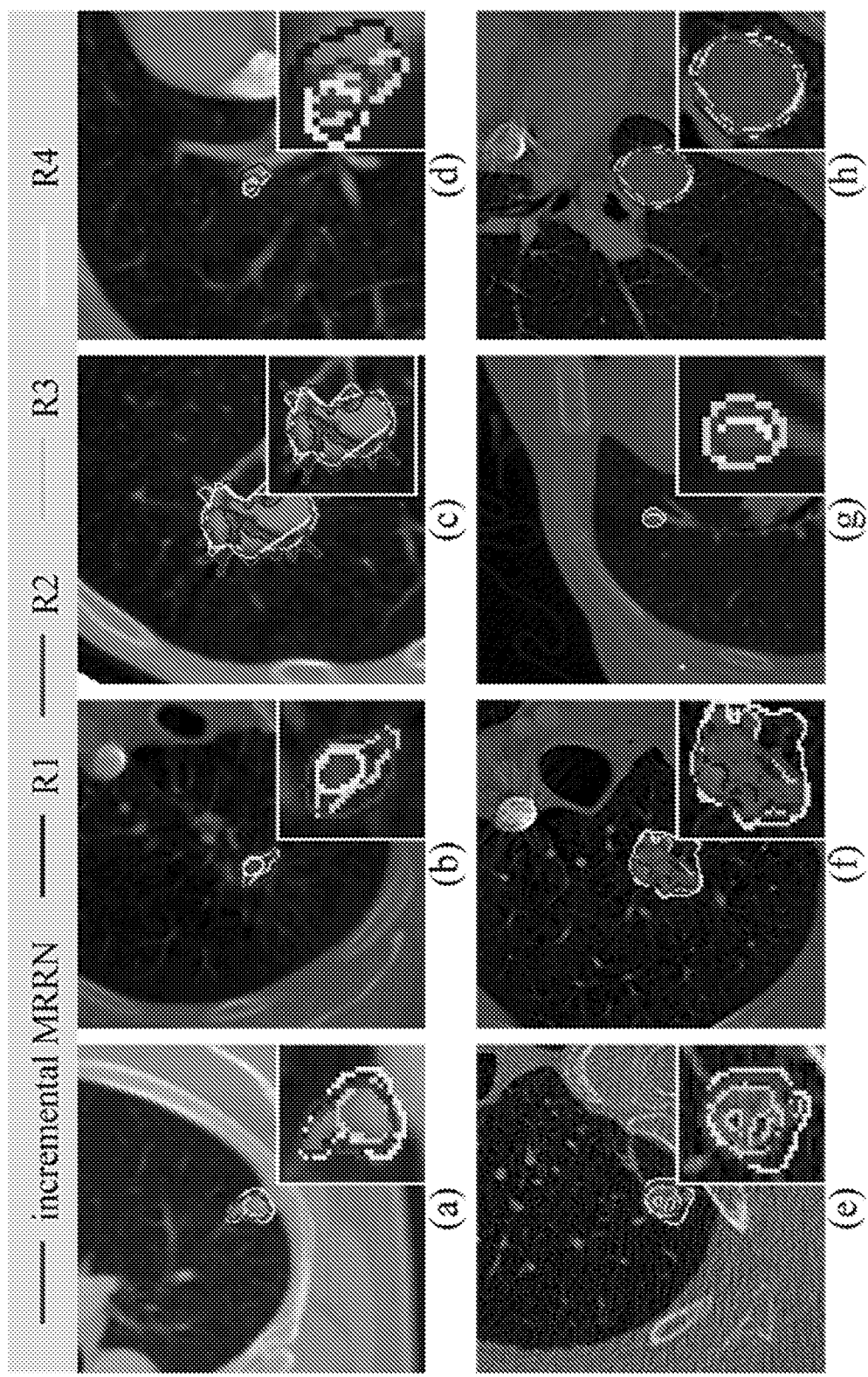
Figure 5C:
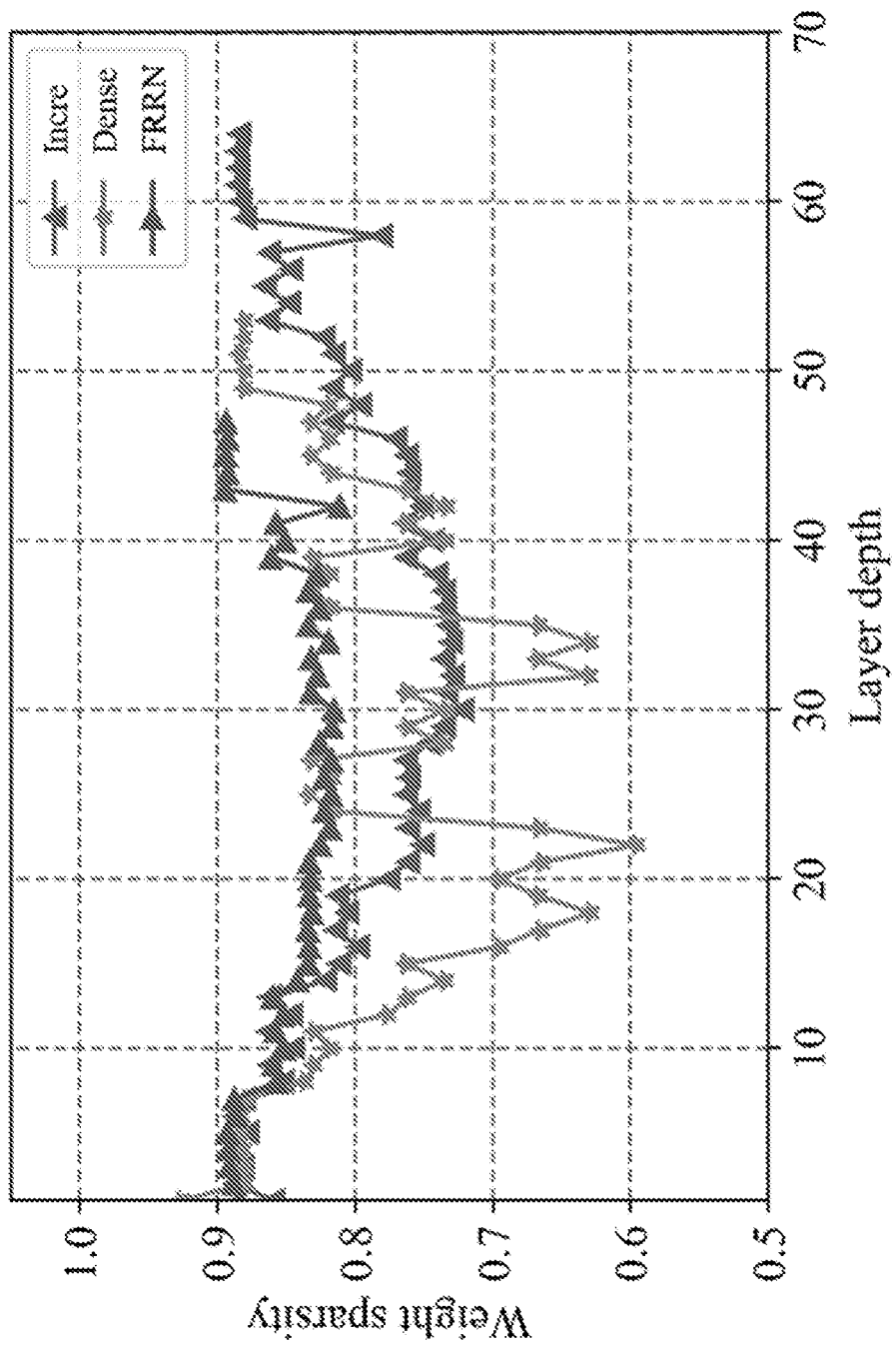
Figure 6A:
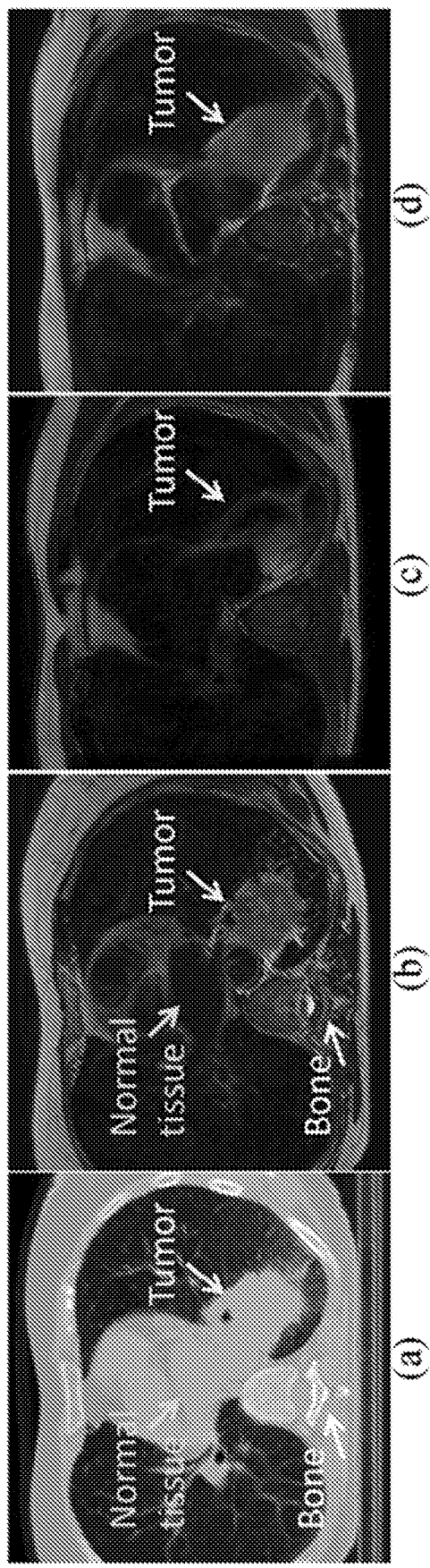
Figure 6B:
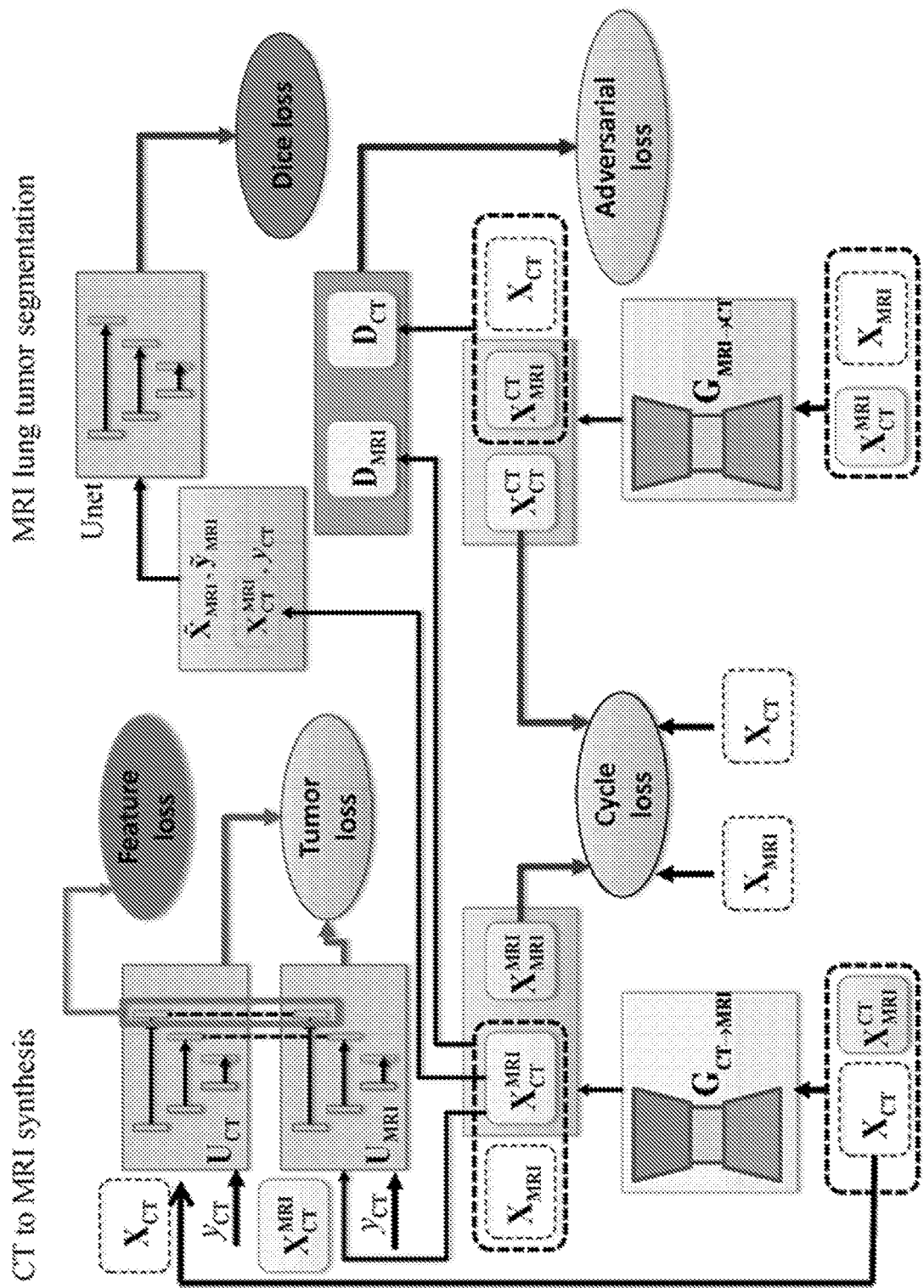
Figure 7A:
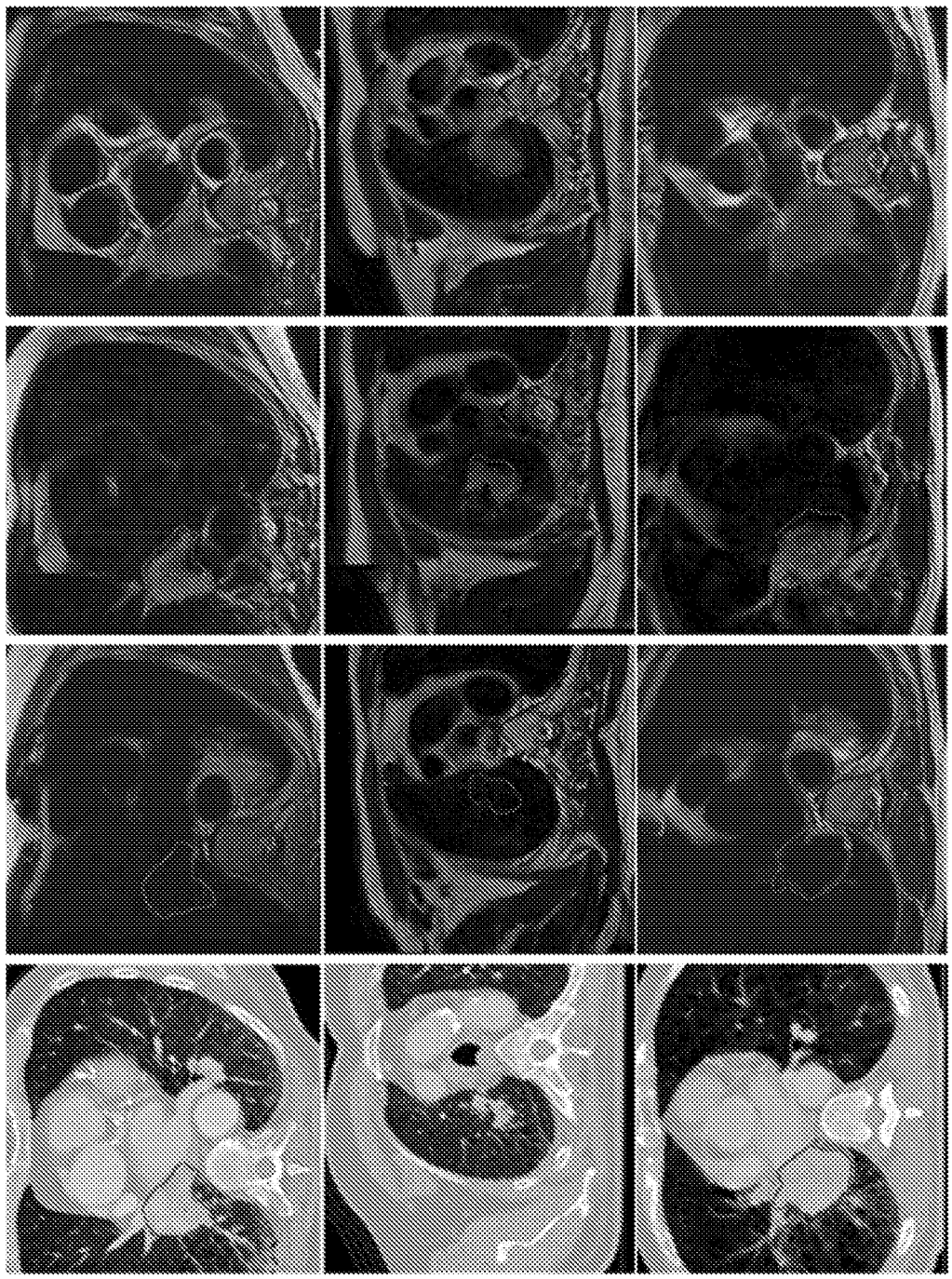
Figure 7B:
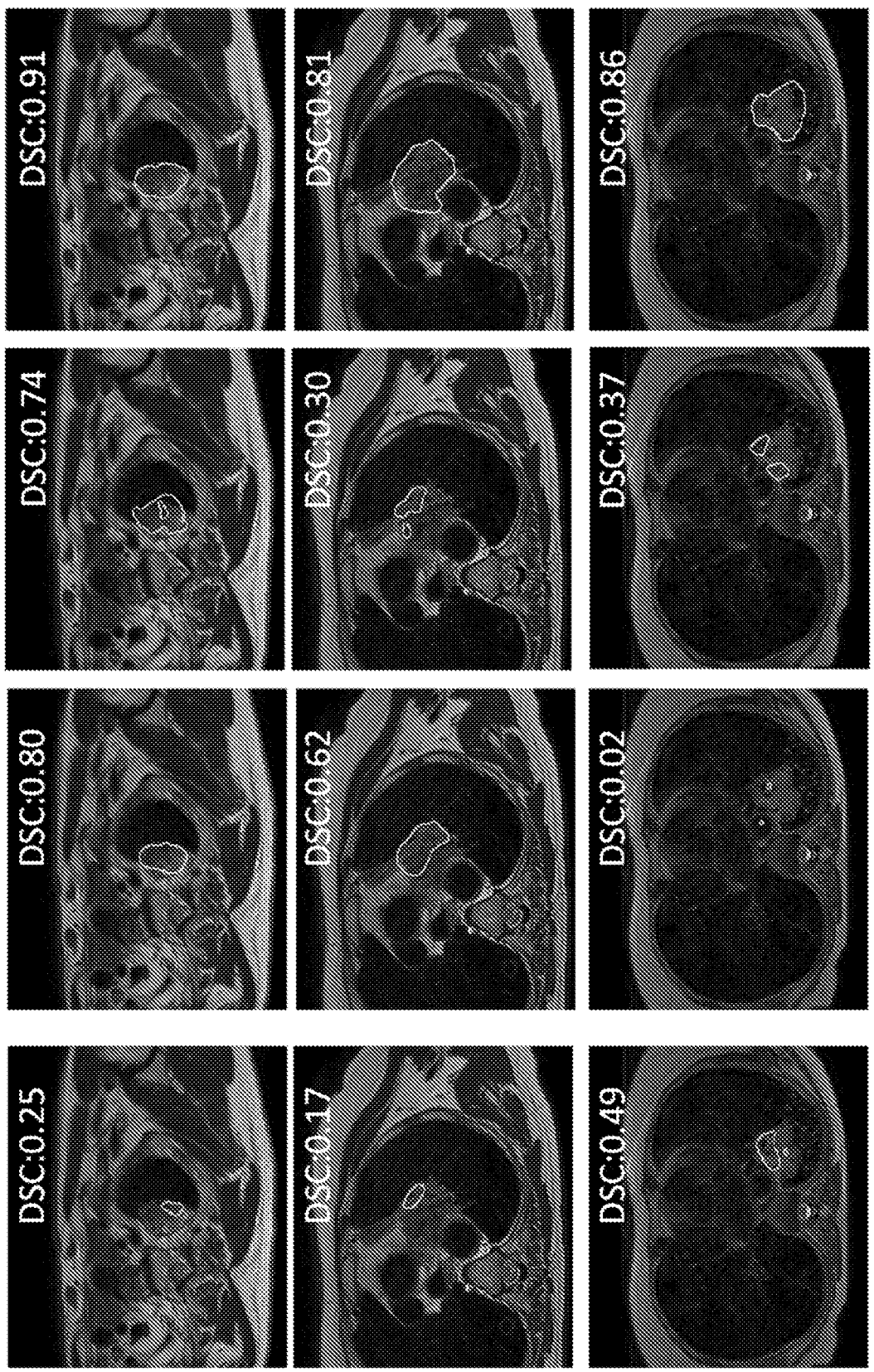
Figure 7C:
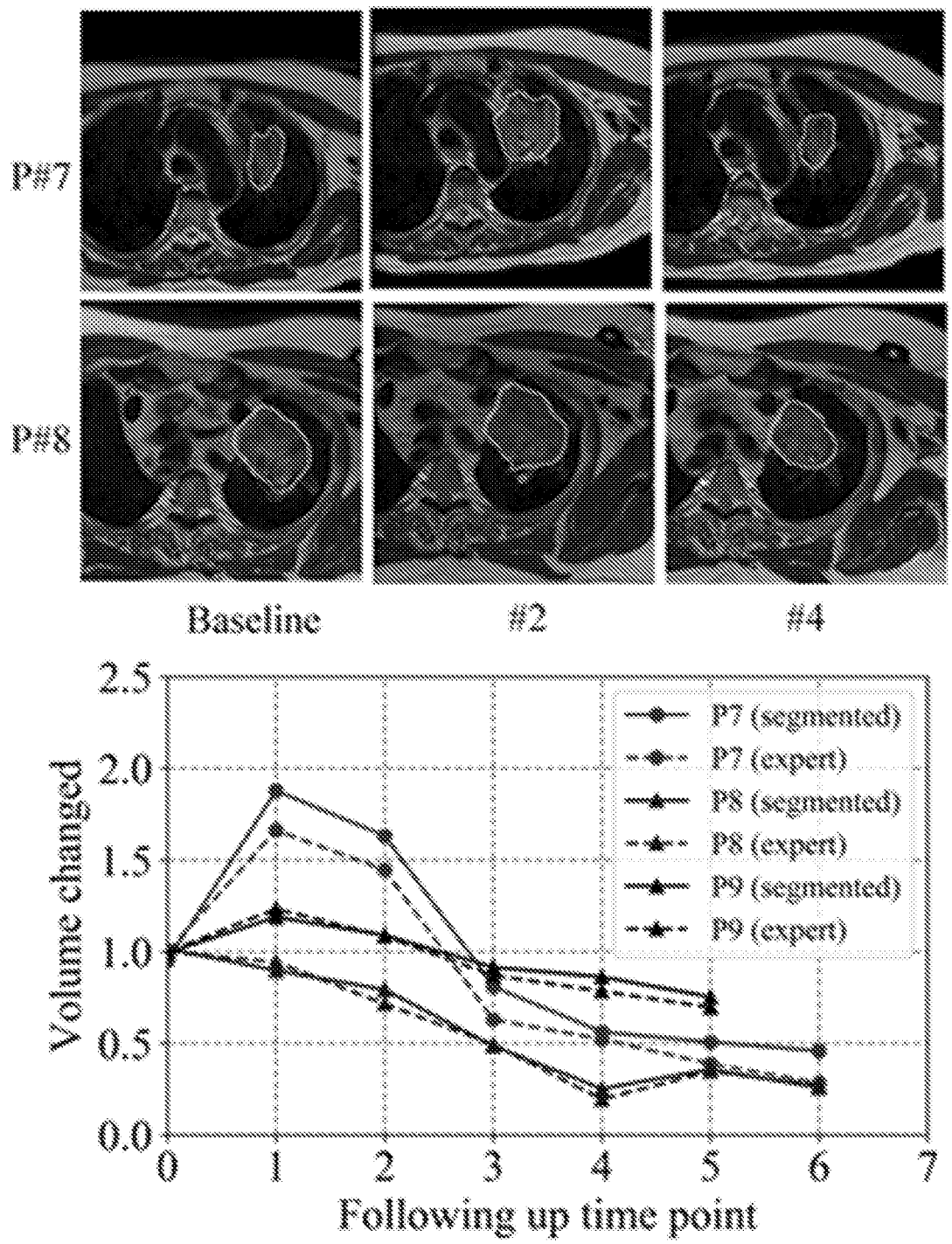
Figure 8A:
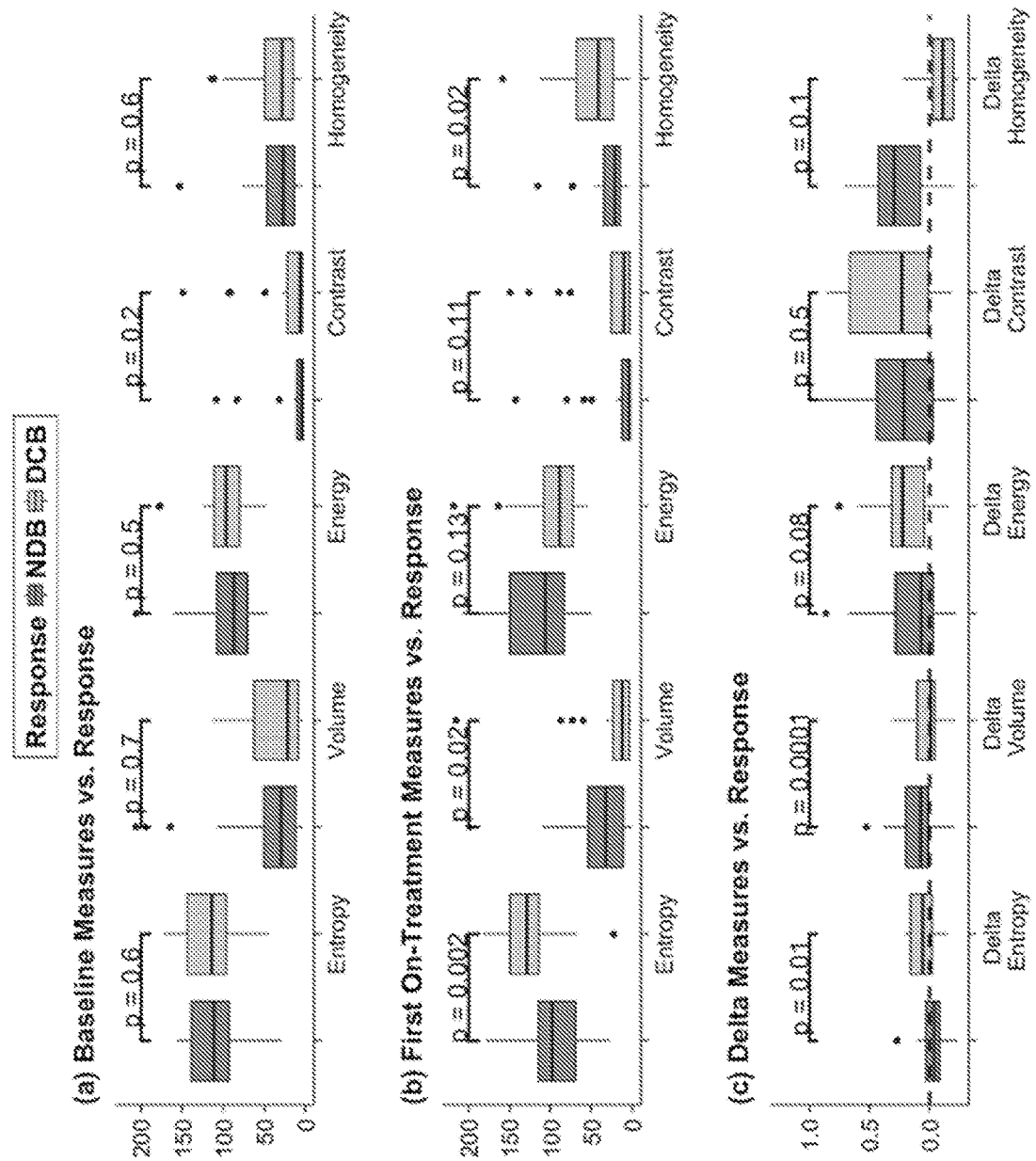

LIDC with varying tumor sizes is shown for DSC and HD95 metrics. VS: very small tumor; S: small tumor; M: middle size tumor; L: large tumor; VL: very large tumor;

FIG. 4B is a graph showing segmentation accuracy using DSC and HD95 metrics of different methods for (a) TCIA, (b) MSKCC and (c) LIDC by tumor locations;

FIG. 4C is a screenshot showing segmentation results of different methods compared to the four radiologists;

FIG. 5A is a screenshot showing segmentation results of incremental MRRN comparison to the four radiologists;

FIG. 5B is a screenshot tumor response with respect measured times. The red solid line and red dot line show the acquired resistance (AR) tumor volume changing calculated by incremental MRRN and delineated by expert, respectively. The blue solid line and blue dot line show the durable resistance (DR) tumor volume changing calculated by incremental MRRN and delineated by expert, respectively. (b) and (c) show the segmentation performance at measurement point: baseline, #1 and #2 of the AR and DR in (a), respectively. The blue contour shows the delineation from expert while the red contour shows the segmentation results;

FIG. 5C is a graph showing weights sparsity with increasing layer depth;

FIG. 6A is a screenshot depicting MRI synthesized from a representative (a) CT image using (c) cycle-GAN and (d) proposed method. The corresponding MRI scan for (a) is shown in (b). As shown, the proposed method (d) using tumor-aware loss helps to fully preserve tumor in the synthesized MRI compared with (c);

FIG. 6B is a block diagram depicting a system architecture for a tumor-aware unsupervised cross-domain adaptation (CT to MRI), followed by (ii) semi-supervised tumor segmentation using Unet trained with synthesized and limited number of original MRIs;

FIG. 6C-I each is a block diagram depicting a system architecture for machine learning automated segmentation from small datasets through structure preserving synthetic MRI generation from CT;

FIG. 7A is a screenshot showing MRI synthesized from CT using different deep learning methods. The red contour indicates the manually delineated tumor region in the NSCLC datasets (a) CT image; (b) cycle-GAN; (c) Masked cycle-GAN; (d) Proposed;

FIG. 7B is a screenshot showing segmentation results on the representative examples from the validation and test set of different methods. The red contour stands for the expert delineations and the yellow contour stands for the segmentation results. (a) segmentation with only week 1 MRI; (b) segmentation using MRI synthesized by cycle-GAN; (c) segmentation using MRI synthesized by masked cycle-GAN; (d) tumor-aware unsupervised learning; (e) tumor-aware semi-supervised learning;

FIG. 7C is a graph showing longitudinal tracking results of three test patients. The red contour stands for the expert delineations and the yellow contour stands for the segmentation results;

FIG. 8A is a graph showing relation between CT image textures and response. A reduction in tumor volume, higher entropy after first treatment, and an increase in entropy, were associated with DCB. P values are shown before adjusting for multiple comparisons.

Figure 8B:
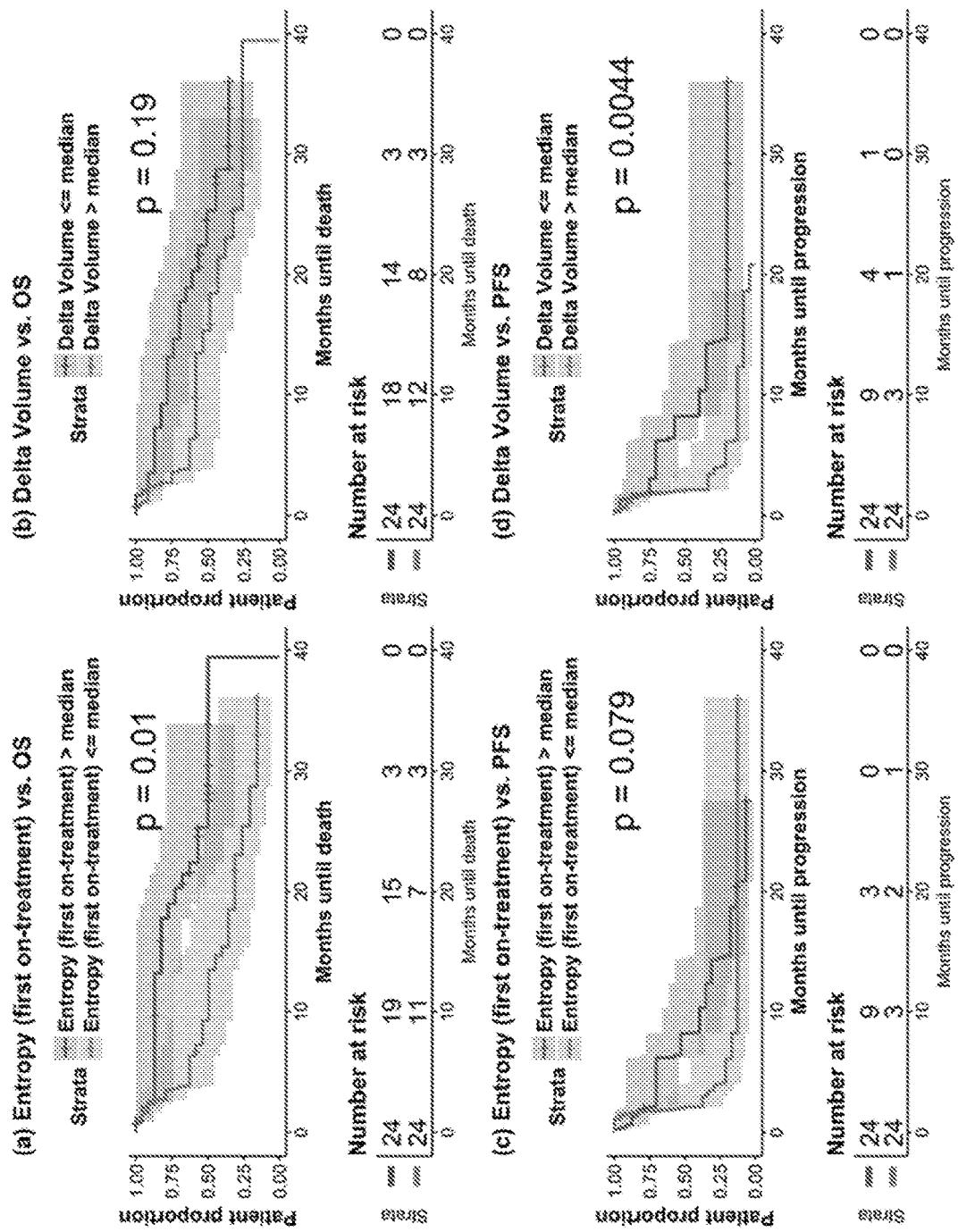

FIG. 8B is a graph showing Kaplan-Meier curves for predicting OS (a,b) and PFS (c,d) using patient groups dichotomized by (a,c) median entropy and (b,d) median $\Delta$volume. Entropy was computed from first on-treatment CT scan.

Figure 8C:
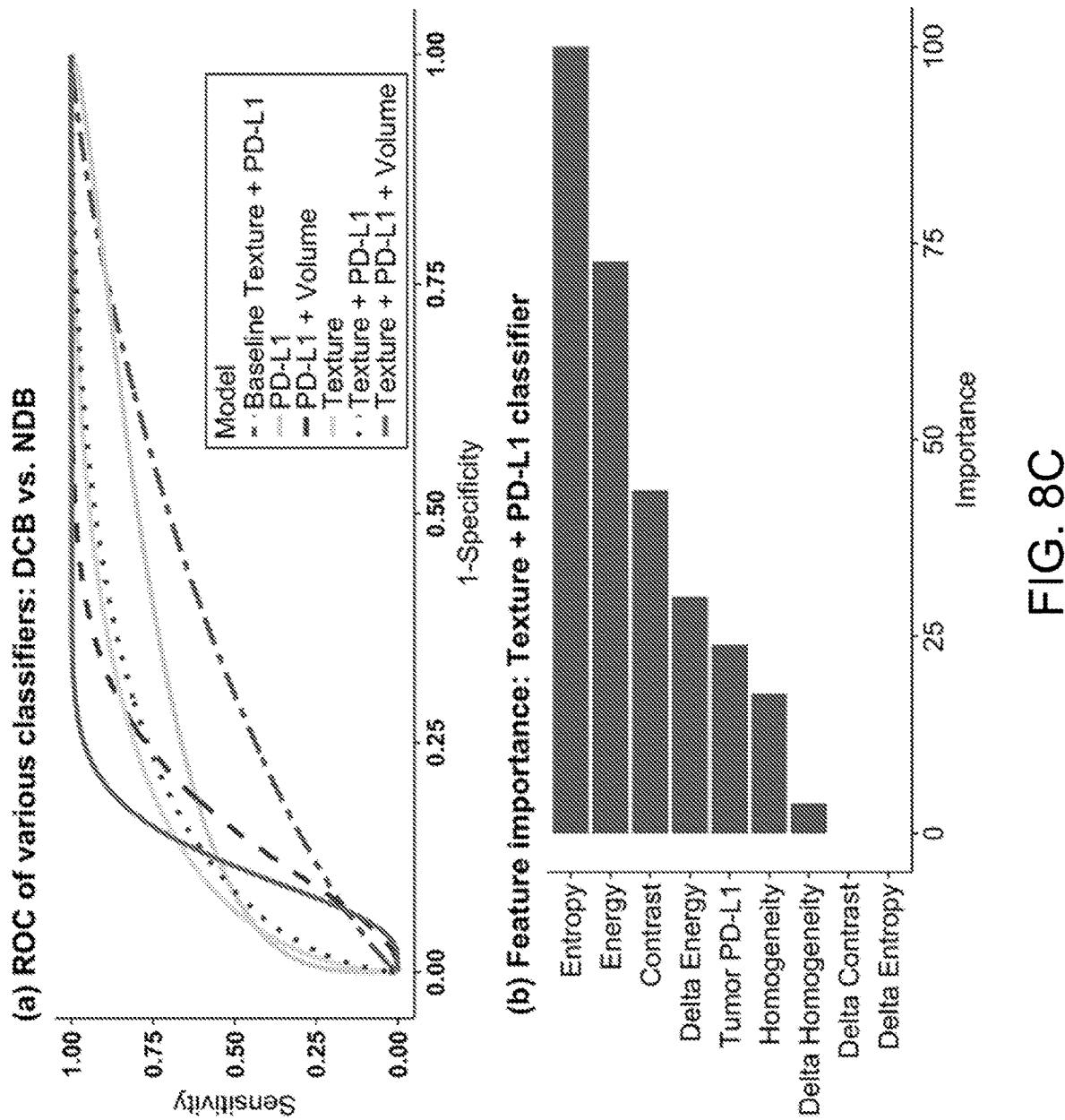

FIG. 8C is a graph showing receiver operating curves (ROC) computed from classifiers trained with texture, volume, tumor-PD-L1 expression for predicting durable clinical response (a), and feature importance ranking for a classifier that combined texture measures (first on-treatment and delta) with quantitative tumor-PD-L1 classifier (b)

Figure 8D:
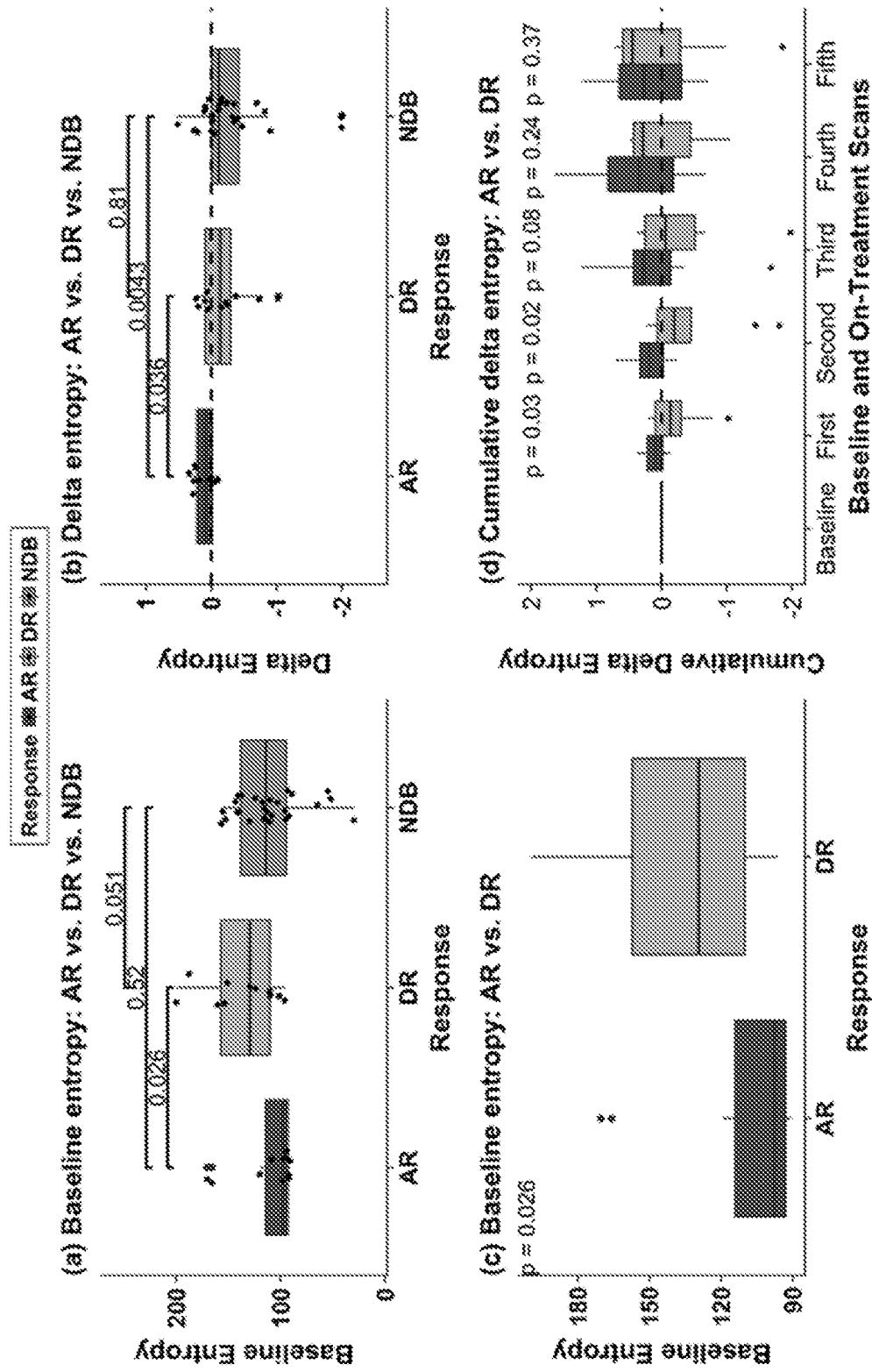
Figure 9:
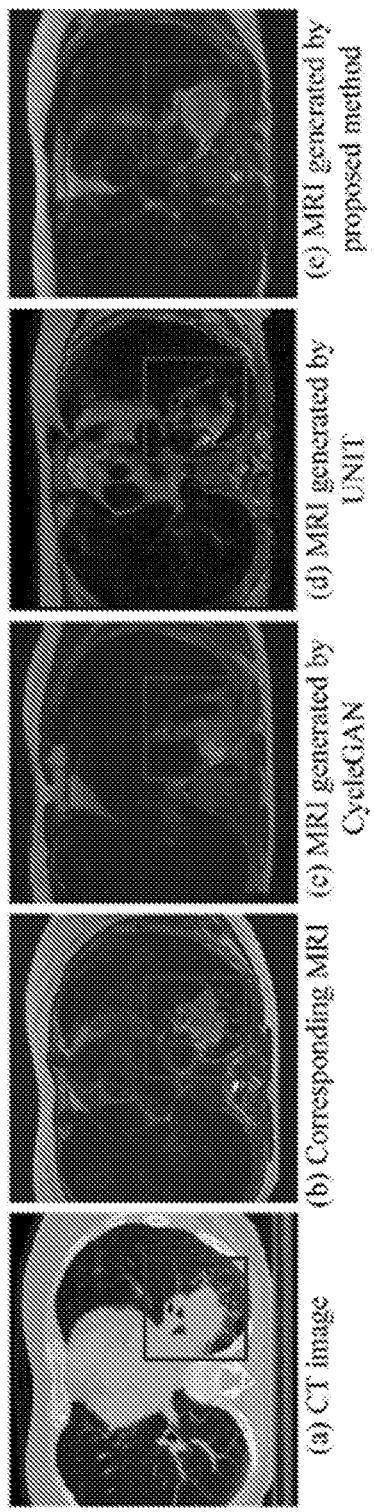

FIG. 8D is a graph showing an increase in entropy associated with acquired resistance. (a,c) High baseline entropy predicted durable response (b) delta entropy was significantly lower for durable responders and non-responders to therapy in comparison to patients who developed acquired resistance, (d) cumulative delta entropy computed at multiple on-treatment CT scans showed significant difference between patients who develop acquired resistance from those with on-going durable response early in treatment FIG. 9 is a set of screenshots showing Pseudo MR image synthesized from a representative (a) CT image using (c) CycleGAN (d) UNIT and 82 (e) proposed method. The corresponding T2w MRI scan for (A) is shown in (b).

Figure 10A:
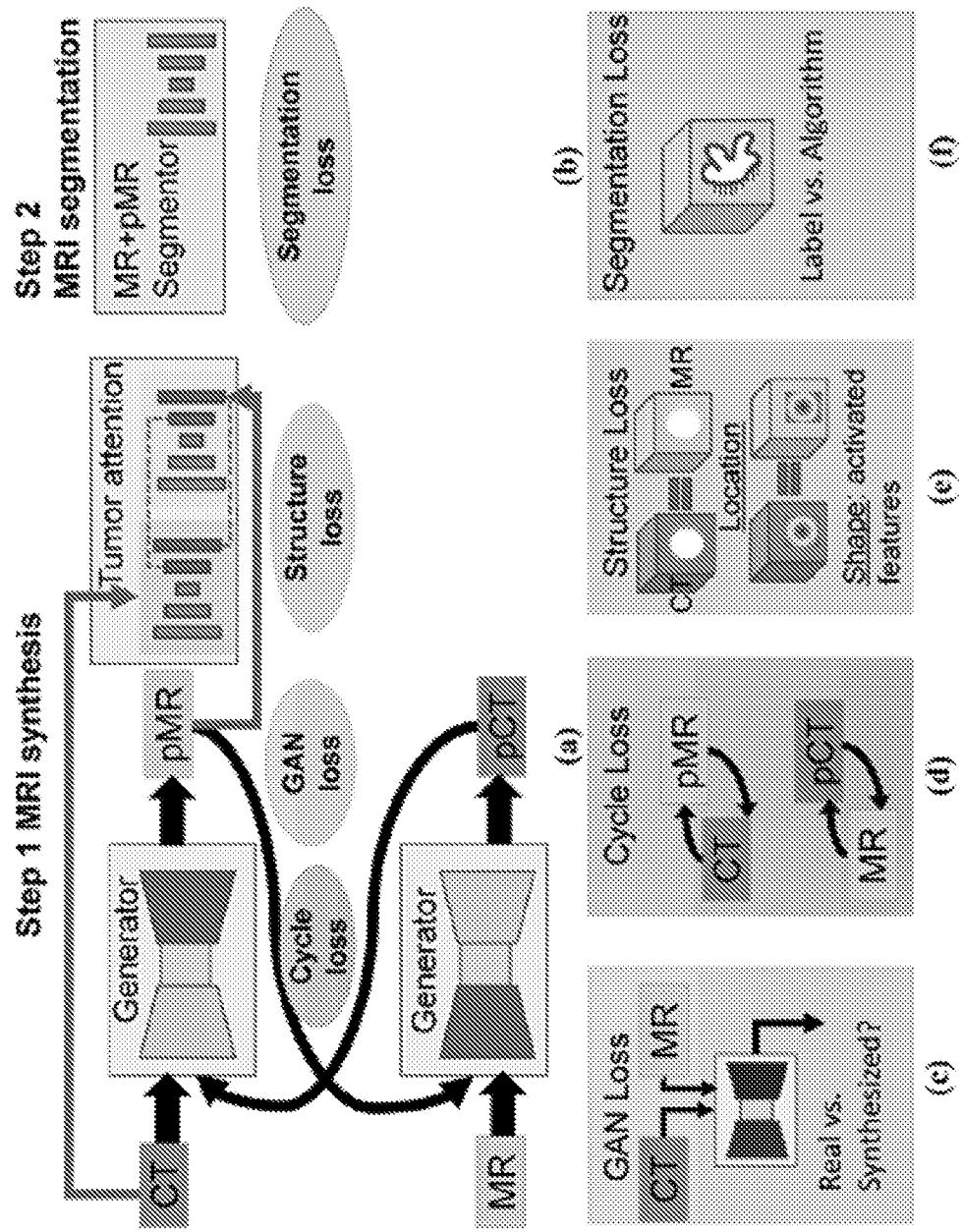
Figure 10B:
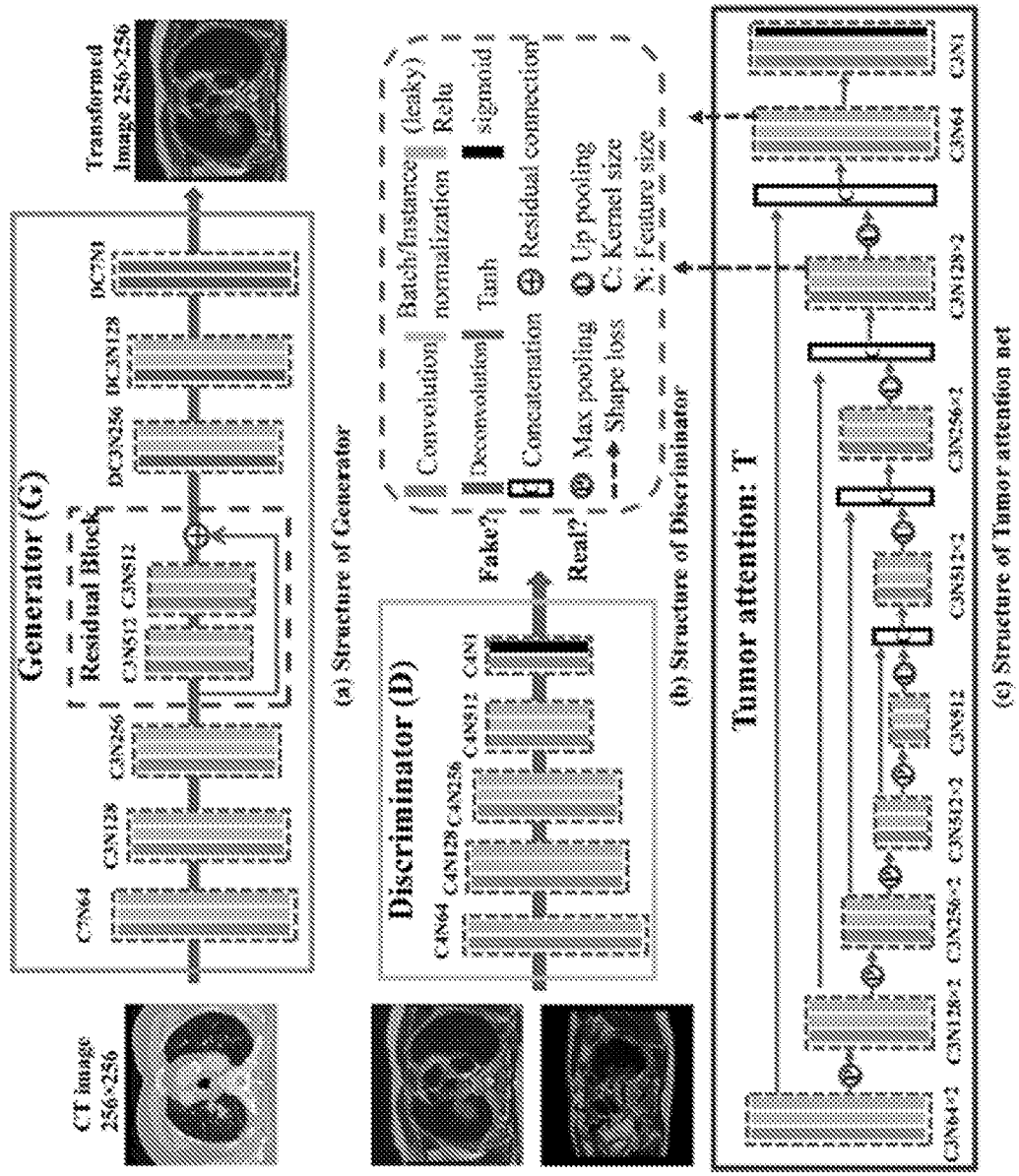

FIG. 10A is a block diagram showing a two-step approach for segmentation: (a) Pseudo MR synthesis, (b) MR segmentation training using pseudo MR with T2w MR. Visual description of losses used in training the networks in (a) and (b), namely, (c) GAN or adversarial loss, (d) cycle or cycle consistency loss, (e) tumor-attention loss enforced using structure and shape loss, and (f) segmentation loss computed using Dice overlap coefficient;

FIG. 10B is a block diagram showing an example structure of the generator, discriminator and tumor attention net. The convolution the kernels size, the number of features are indicated as C and N. For instance, C3N512 denotes a convolution with kernel size of 3×3 and feature size of 512.

Figure 10C:
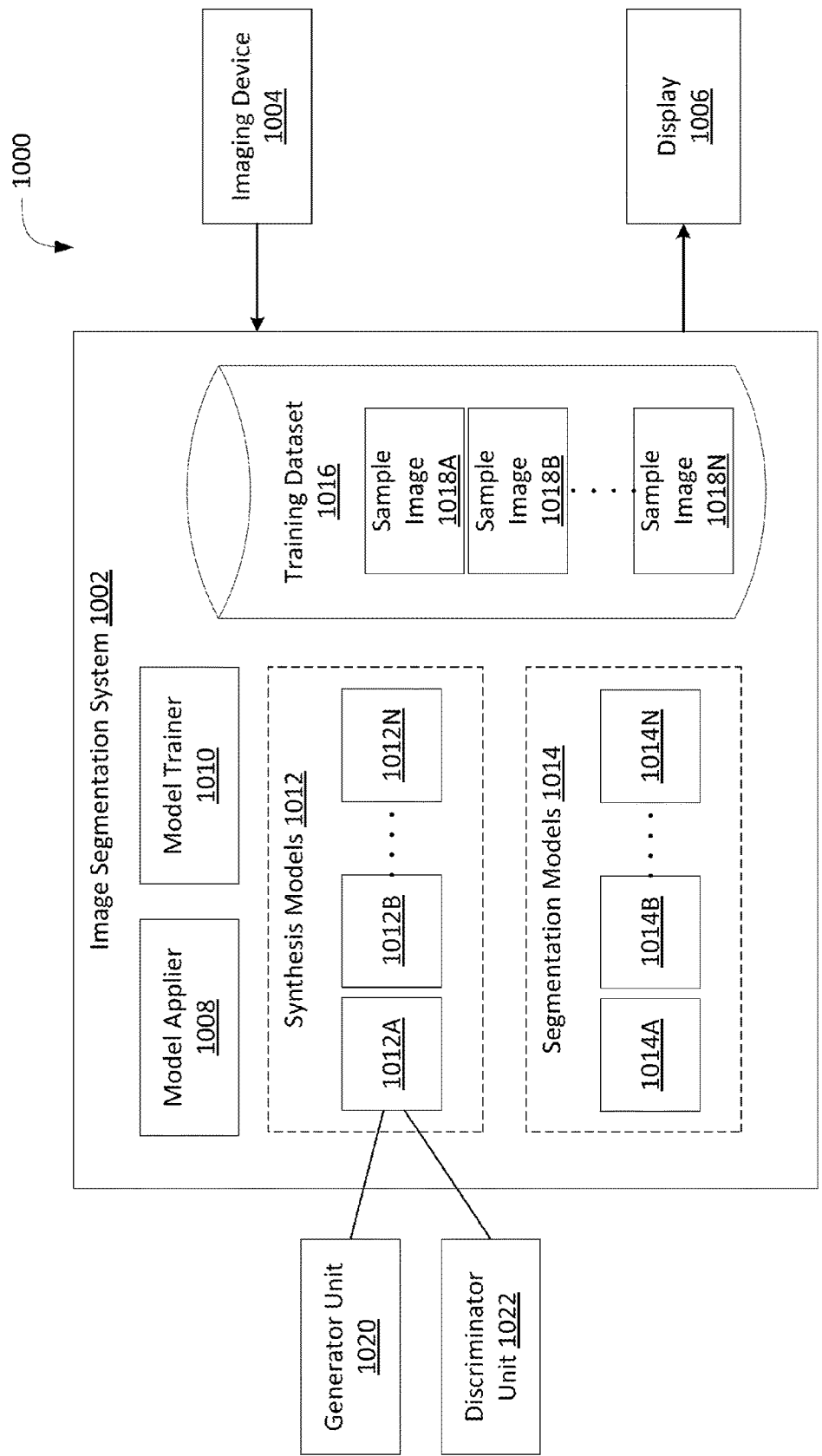
Figure 10D:
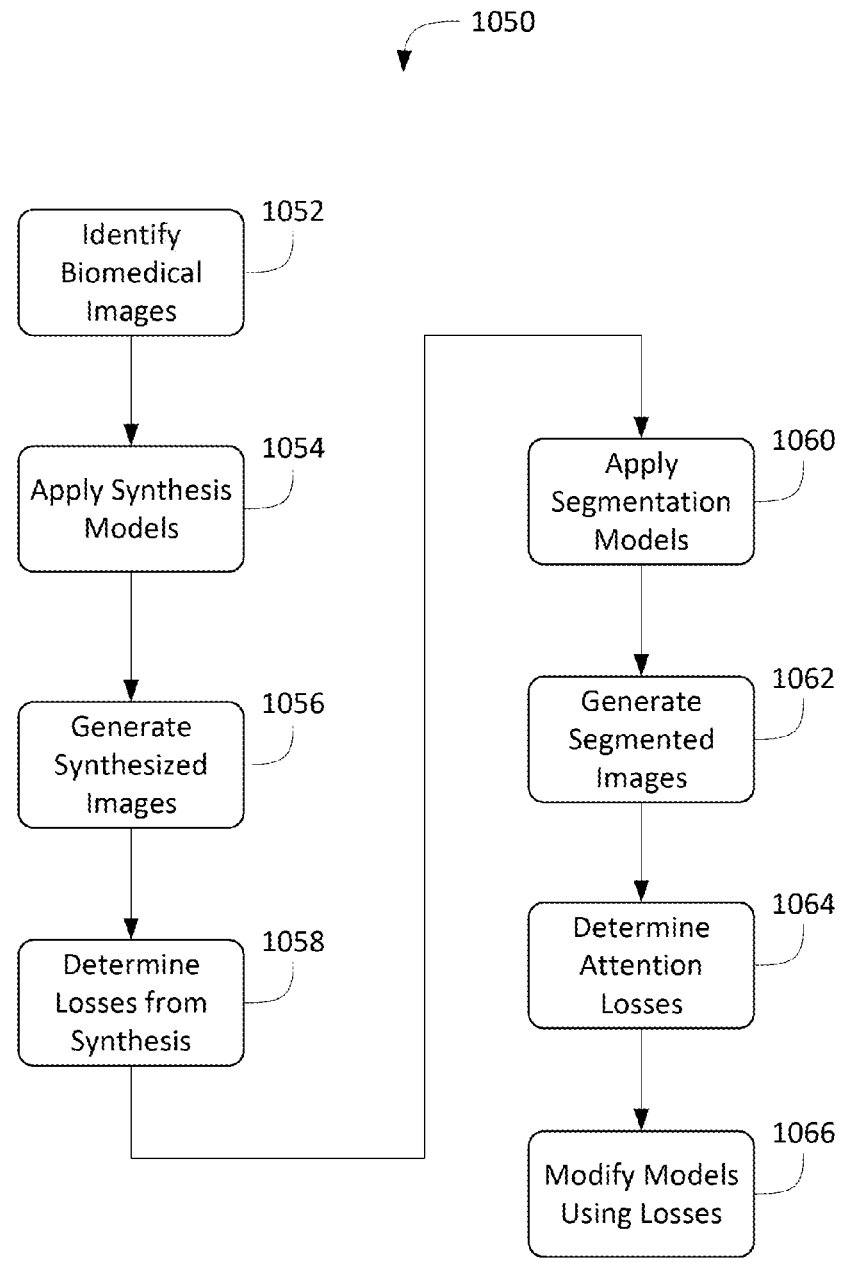
Figure 11:
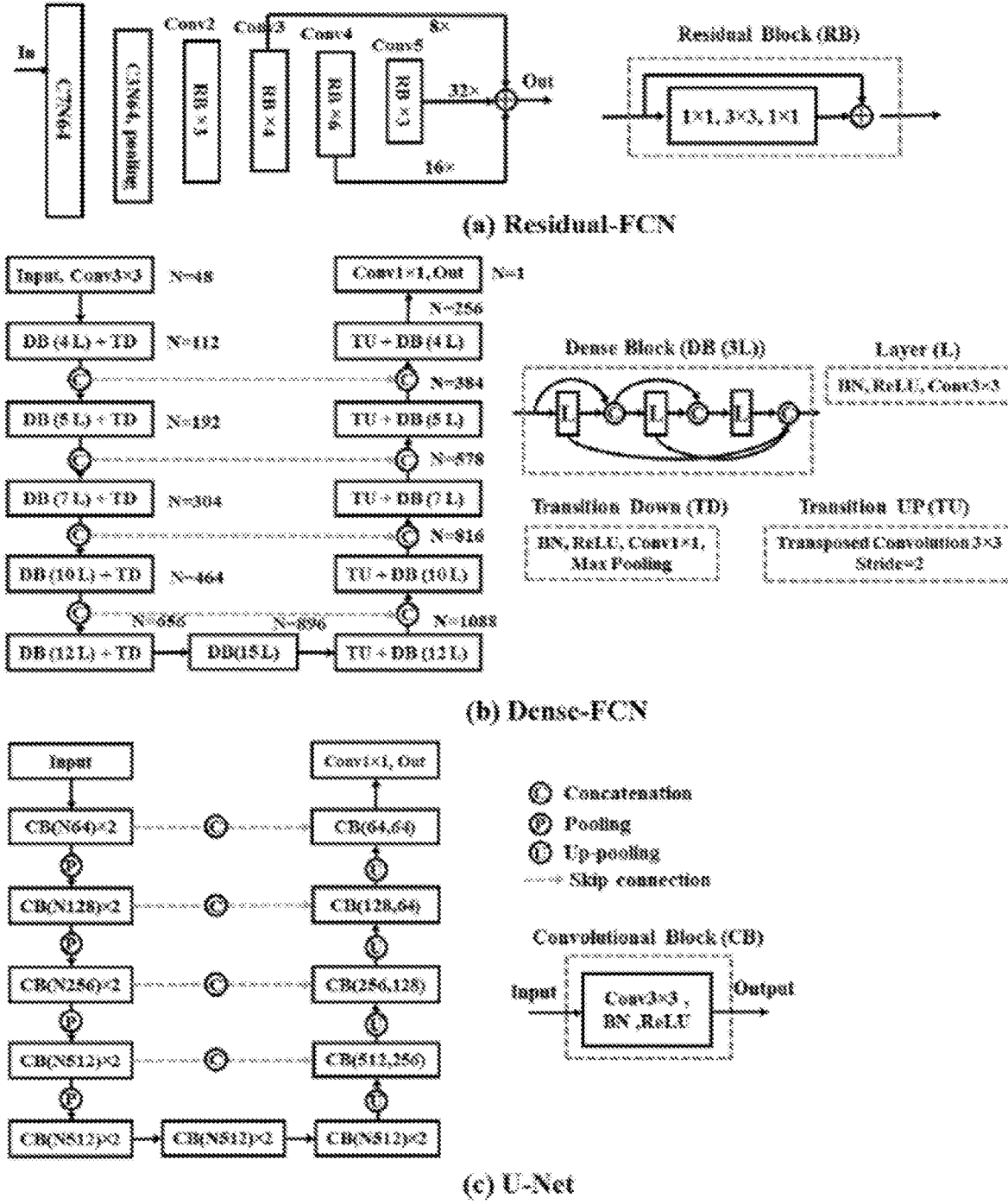

FIG. 10C is a block diagram of an example system for training models for segmenting biomedical images based on cross-domain adaptations;

FIG. 10D is a flow diagram of an example method of training models for segmenting biomedical images based on cross-domain adaptations;

FIG. 11 is a block diagram of an example schematic of segmentation architectures, consisting of (A) Residual FCN, (B) Dense-FCN and (c) UNet. The convolutional kernel size and the number of features are indicated as C and N.

Figure 12A:
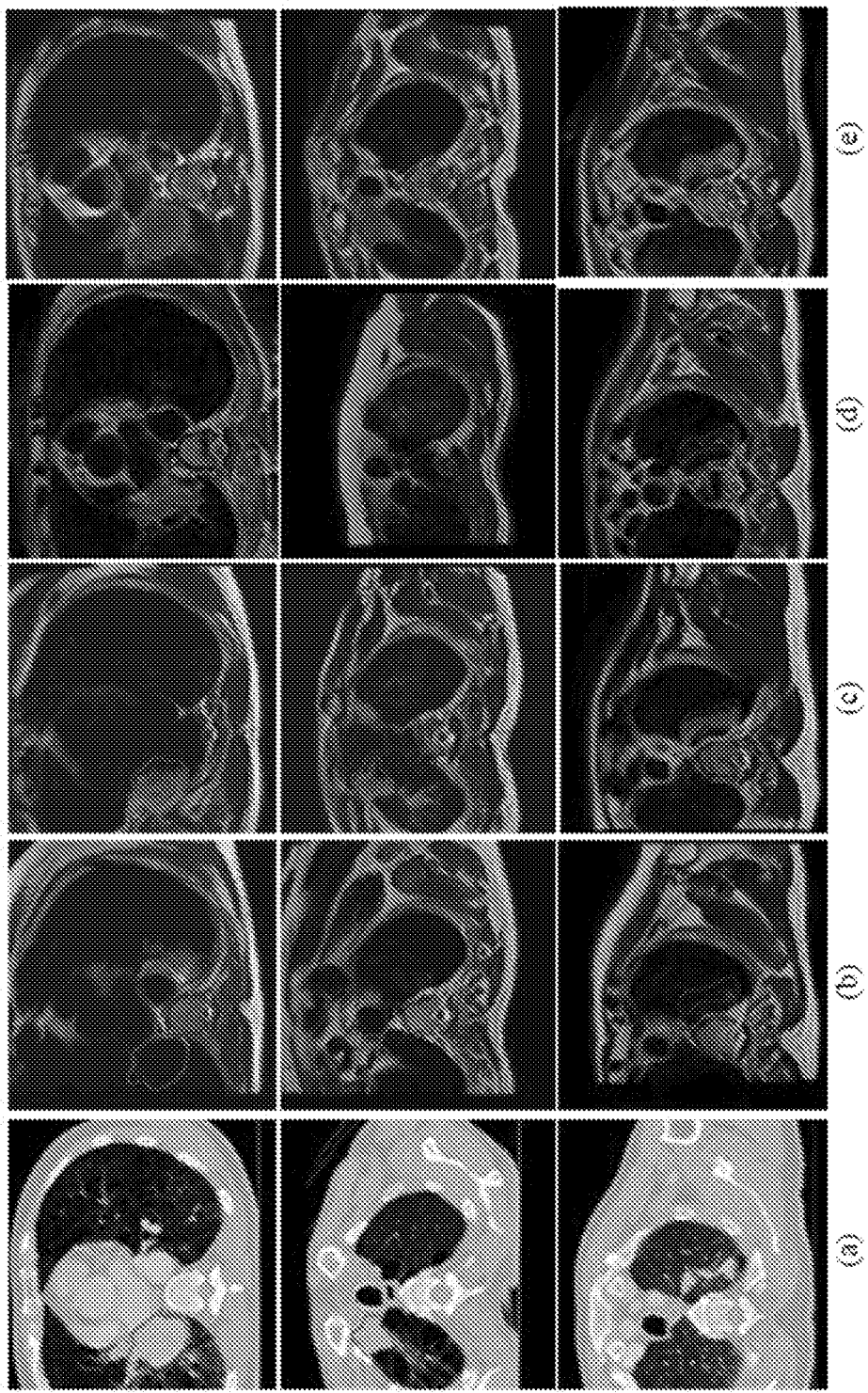

FIG. 12A is a set of screenshots showing CT to pseudo MRI transformation using the analyzed methods. (a) Original CT; pseudo MR image produced using (b) CycleGAN; (c) masked CycleGAN (d) UNIT and (e) the method of the present disclosure.

Figure 12B:
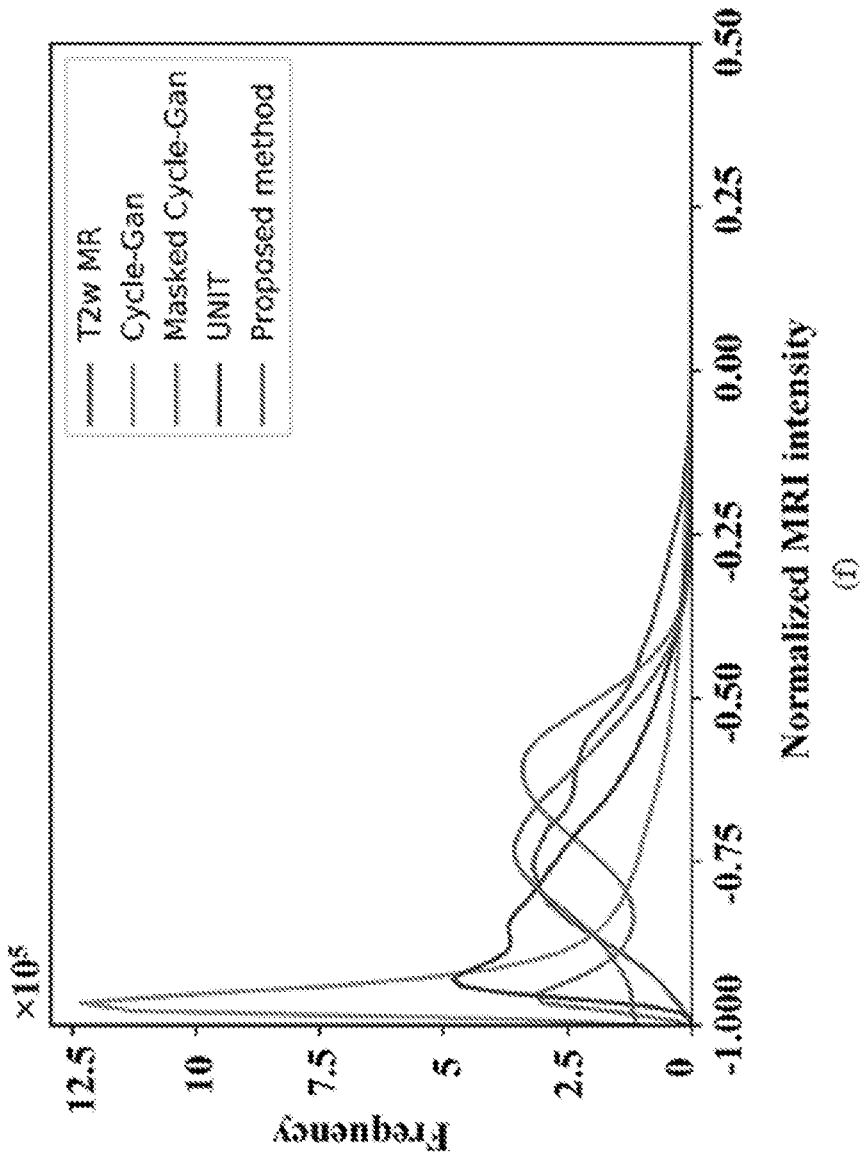

FIG. 12B is a graph showing the abscissa (x-axis) shows the normalized MRI intensity and the ordinate (y-axis) shows the frequency of the accumulated pixel numbers at that intensity for each method in the tumor region. The T2w MR intensity distribution within the tumor regions from the validation patients is also shown for comparison.

Figure 13:
Figure 15A:
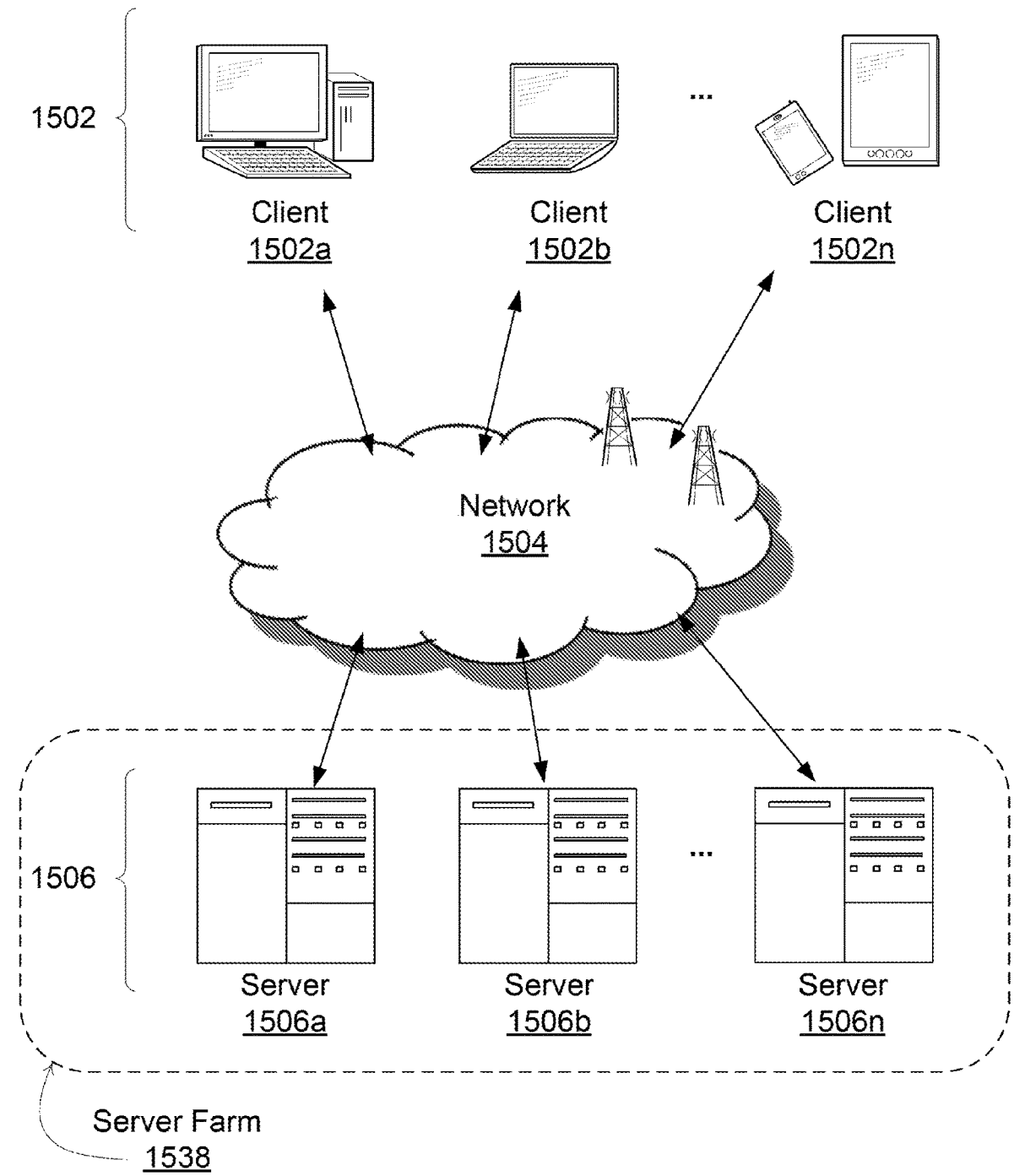
Figure 15B:
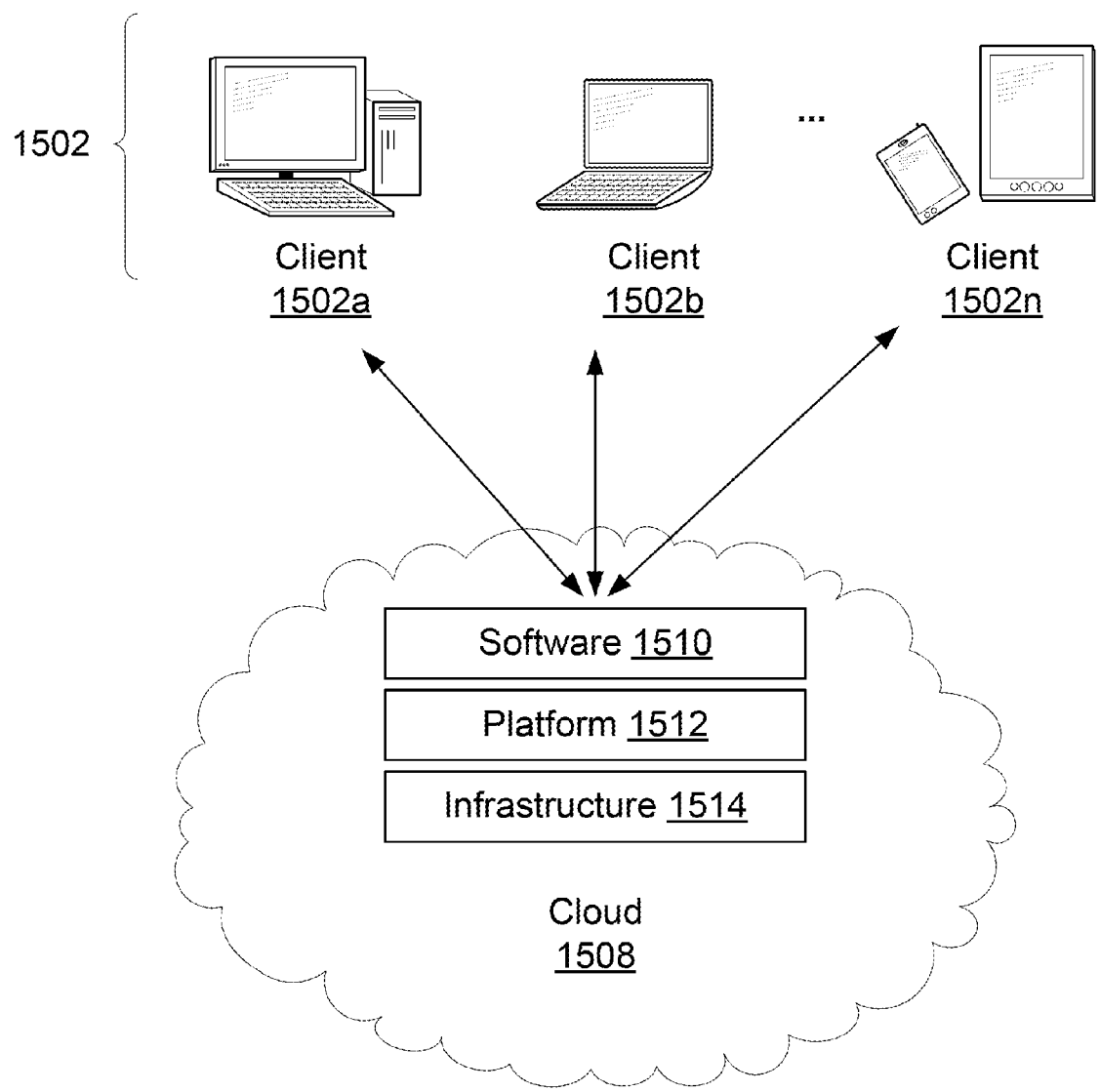
Figure 15C:
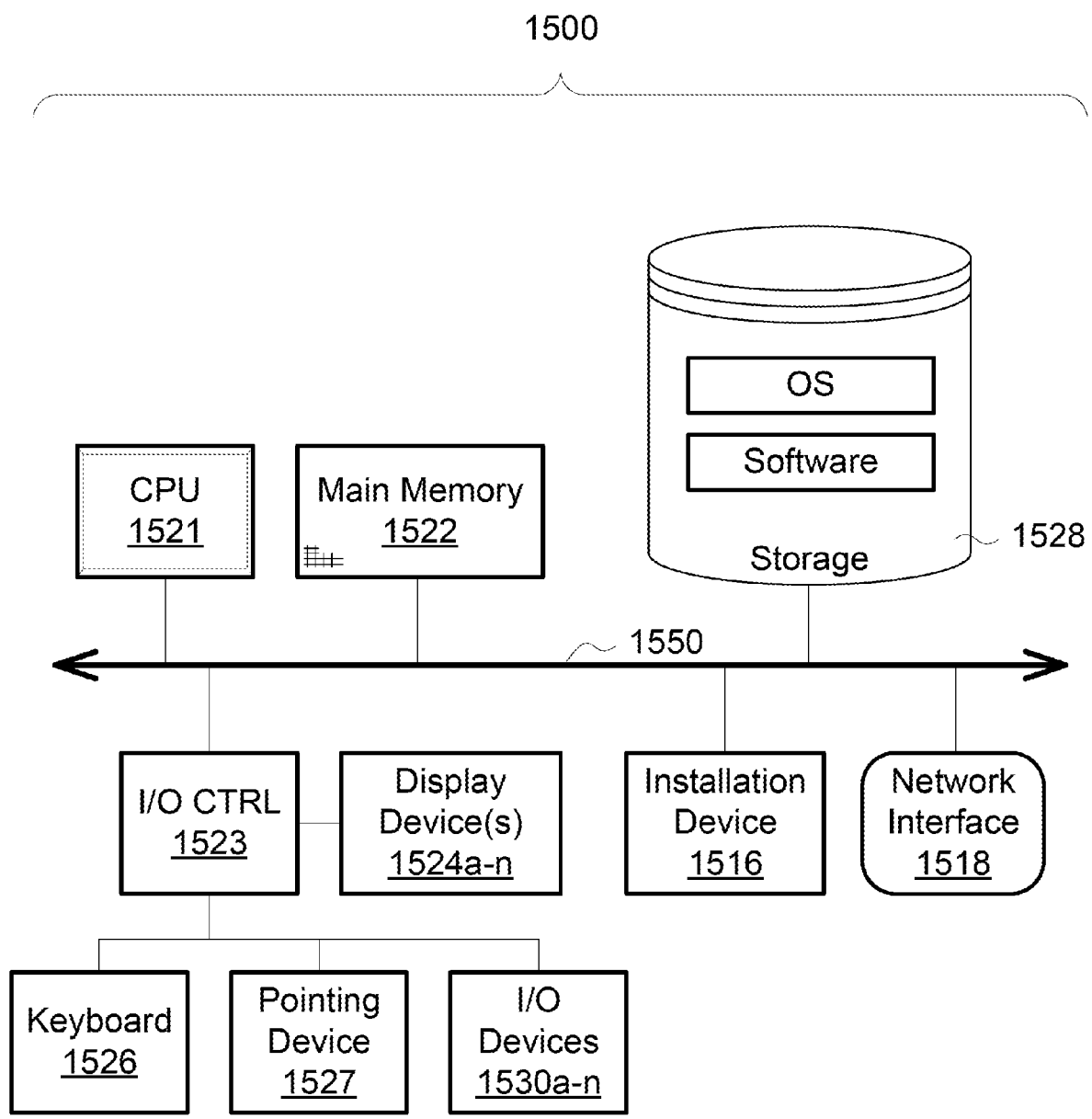
Figure 15D:
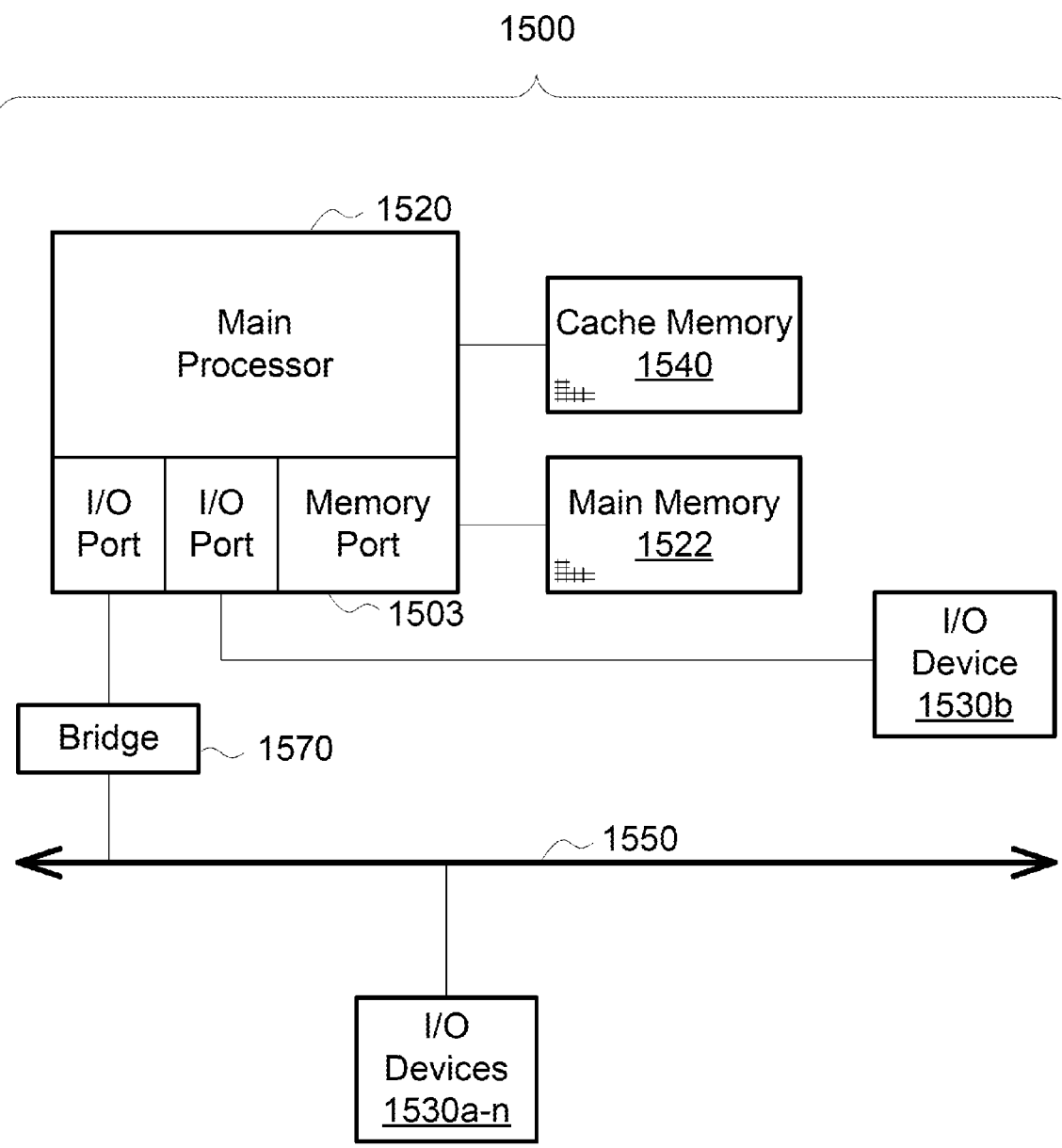

FIG. 13 is set of screenshots showing segmentations from representative examples from five different patients using different data augmentation methods. (a) RF+fCRF segmentation; (b) segmentation using only few T2 W MRI; training combining expert-segmented T2w MRI with pseudo MRI produced using (c) CycleGAN; (d) masked CycleGAN; (e) UNIT; (g) method of the present disclosure. (f) shows segmentation results from training using only the pseudo MRI produced using proposed method. The red contour corresponds to the expert delineation while the yellow contour corresponds to algorithm generated segmentation;

FIG. 14 is a graph and a set of screenshots. Longitudinal tumor volumes computed from three example patients using proposed method. (a) Volume growth velocity calculated by proposed versus expert delineation (b) Segmentation results from patient 7 and patient 8. The red contour corresponds to the expert delineation while the yellow contour corresponds to algorithm generated segmentation FIG. 15A is a block diagram depicting an embodiment of a network environment comprising a client device in communication with a server device;

FIG. 15B is a block diagram depicting a cloud computing environment comprising a client device in communication with cloud service providers;

FIGS. 15C and 15D are block diagrams depicting embodiments of computing devices useful in connection with the methods and systems described herein.

DETAILED DESCRIPTION

For purposes of reading the description of the various embodiments below, the following descriptions of the sections of the specification and their respective contents may be helpful:

Section A describes embodiments of systems and methods for multi-modal, multi-resolution deep learning segmentation of tumors and organs at risk;

Section B describes embodiments of systems and methods for automated segmentation from small datasets through structure preserving synthetic magnetic resonance imaging (MRI) generation from computed tomography (CT);

Section C describes embodiments of systems and methods for deep learning-based segmentation enables predicting treatment outcomes and longitudinal treatment monitoring;

Section D describes embodiments of systems and methods for cross modality prior-augmented deep learning for robust lung segmentations from small datasets; and Section E describes a network environment and computing environment which may be useful for practicing embodiments described herein.

A. Systems and Methods for Multi-Modal, Multi-Resolution Deep Learning Segmentation of Tumors and Organs at Risk Volumetric lung tumor segmentation and accurate longitudinal tracking of tumor volume changes from computed tomography (CT) images are essential for monitoring tumor response to therapy. Hence, two multiple resolution residually connected network (MRRN) formulations called incremental-MRRN and dense-MRRN were developed. The networks simultaneously combine features across multiple image resolution and feature levels through residual connections to detect and segment lung tumors. The method was evaluated on a total of 1210 non-small cell (NSCLC) lung tumors and nodules from three datasets consisting of 377 tumors from the open-source Cancer Imaging Archive (TCIA), 304 advanced stage NSCLC treated with anti-PD-1 checkpoint immunotherapy from internal institution MSKCC dataset, and 529 lung nodules from the Lung Image Database Consortium (LIDC). The algorithm was trained using the 377 tumors from the TCIA dataset and validated on the MSKCC and tested on LIDC datasets. The segmentation accuracy compared to expert delineations was evaluated by computing the Dice Similarity Coefficient (DSC), Hausdorff distances, sensitivity and precision metrics. In comparison to other methods, the best performing incremental-MRRN method produced the highest DSC of 0.74±0.13 for TCIA, 0.75±0.12 for MSKCC and 0.68±0.23 for the LIDC datasets. There was no significant difference in the estimations of volumetric tumor changes computed using the incremental-MRRN method compared with expert segmentation. In summary, a multi-scale CNN approach was developed and applied for volumetrically segmenting lung tumors which enables accurate, automated identification of and serial measurement of tumor volumes in the lung.

Introduction

Lung cancer is the most common cause of cancer death worldwide. In patients with lung cancer treated with systemic therapy, the relative benefits of treatment are routinely determined by measurement of changes in size of tumor lesions, usually using unidimensional measurement, such as RECIST v1.1. The applications of automatic tumor segmentation are broad, including measuring treatment response, planning of radiation treatment, and to facilitate extraction of robust features for high-throughput radiomics.

Manual delineation of tumor volumes is extremely laborious and prior studies have shown that semi-automatic computer-generated segmentations are more repeatable than manual delineations especially for radiomics analysis. Representative semi-automated tumor segmentation approaches applied to lung cancers include single-click ensemble methods and marker-controlled watershed method. However, such methods when applied to lung nodule segmentation produce varying results. Interactive methods that adapt their segmentation to user inputs suffer from inter-rater variability.

Reproducible segmentation is essential for longitudinal monitoring of tumor response to therapy. Learning even on a tumor-by-tumor basis can lead to more reproducible tumor segmentations for multiple cancers. Fully automatic convolutional neural network (CNN) based approaches such as AlexNet, VGG, GoogleNet have shown remarkable success in a variety of computer vision and medical image analysis tasks (e.g., UNet, Vnet). Residual networks (ResNet) achieve fast and stable training irrespective of the network depth and are robust to layer removal at training and inference time due to learning through iterative feature refinement.

However, the residual connections alone used in ResNet do not eliminate the issue of poor localization and blurring resulting from successive pooling operations which is undesirable for segmentation. Therefore, the full resolution residual neural network (FRRN) extended ResNet by passing features at full image resolution to each layer. By concatenating features with lower resolution features, FRRN has demonstrated better segmentation performance compared with six different CNNs when using street images. The present disclosure extends and improves over the FRRN by residually combining features computed at multiple image resolutions, whereby, a dense feature representation is computed by simultaneously combining feature maps at multiple image resolutions and feature levels. Such a dense feature representation increases the network capacity and ultimately enables the network to recover the input image spatial resolution better than the existing methods.

The contribution includes two different multiple resolution residual networks (MRRN) called the incremental and dense MRRN. Feature map input in each residual stream is produced through pooling (for dense MRRN) and followed by convolutions with residual connections (for the incremental MRRN). Additionally, the feature maps in each residual stream are refined as they are combined with subsequent layers.

Schematics

Figure 1A:
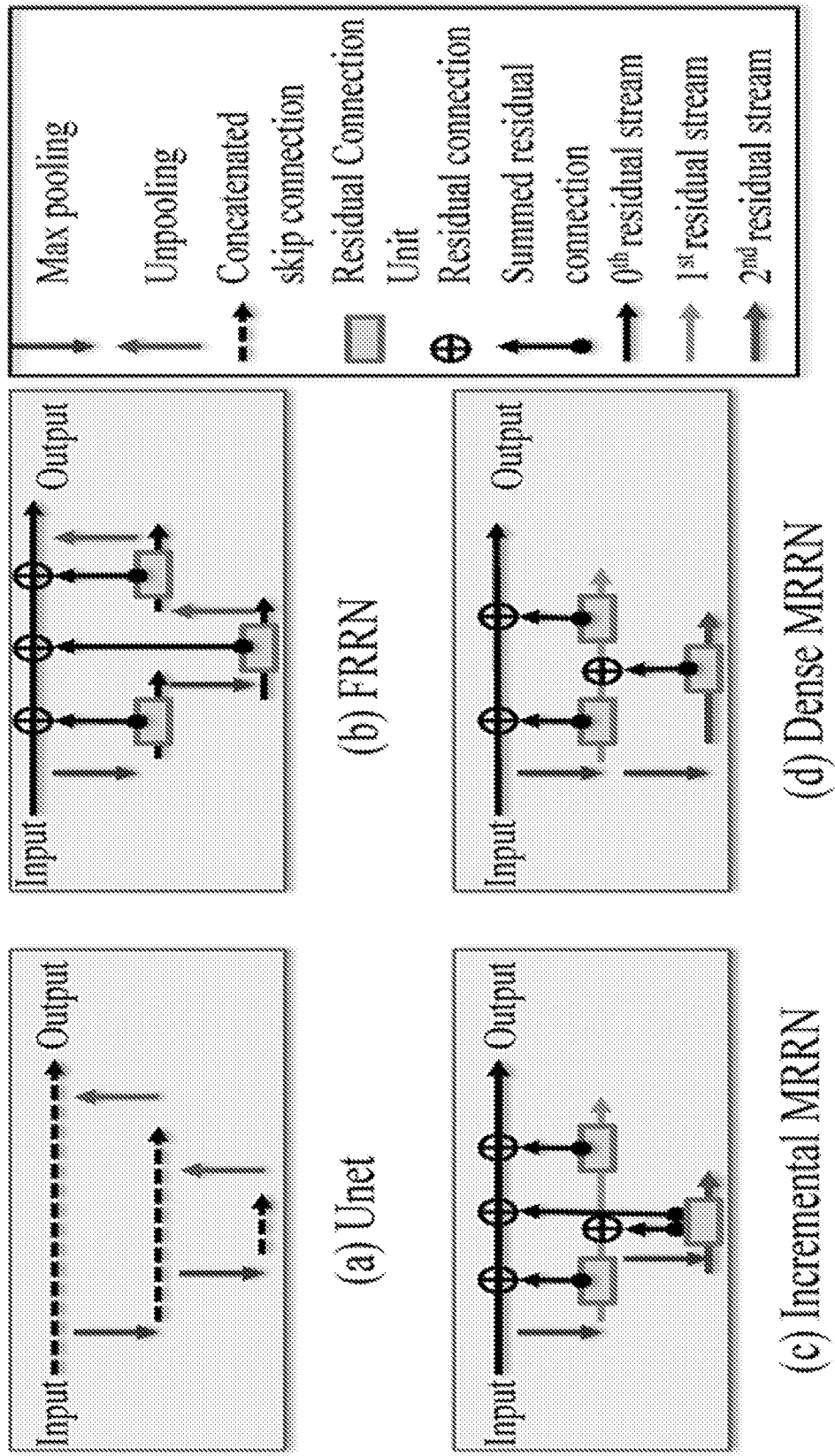
FIG. 1A is a block diagram depicting a schematic structure of Unet, full resolution residual neural network (FRRN), incremental multiple resolution residual network (MRRN), and dense MRRN.

FIG. 1A depicts the schematic of the various network used in this is work namely, the UNet, the FRRN, and the proposed incremental and dense MRRN methods. UNet (a) employs sequential long skip connections to concatenate features computed at different feature resolutions in the encoding path with those in the decoding path. Long skip connection restricts feature map combination to those produced at the same image resolution and leads to under-utilization of the rich feature representation in the image. ResNet and highway networks reduce feature under-utilization by connecting output from the previous layer to the input of a current layer through an element-wise summation that enables local feature combination with immediate higher resolution. The FRRN (b) extends ResNet by maintaining features maps computed at full image resolution that are combined with lower resolution feature maps in addition to residual concatenation with features of immediately higher resolution.

Figure 1B:
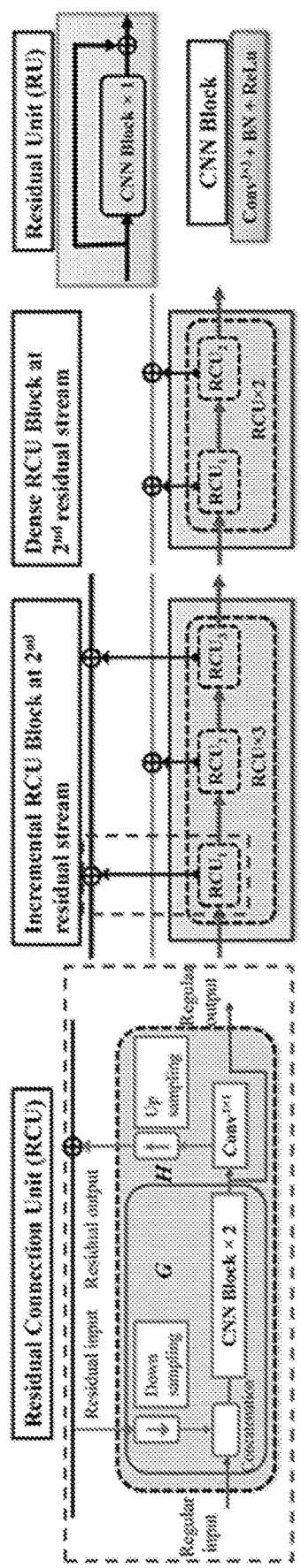
FIG. 1B is a block diagram depicting a configuration of each component in incremental MRRN and dense MRRN.

Two multiple resolution residual network (MRRN) may be used for extracting dense feature representations using incremental MRRN (c) and dense MRRN (d) that pass feature maps of different levels at varying image resolutions. Table I depicts the comparison between the multiple networks The various components used in the networks as depicted in FIG. 1B may include:

Residual streams carry feature maps computed at an image resolution and provide the residual inputs to residual connection units (RCU). For example, zero residual stream, shown by horizontal black arrow in FIG. 1A, carries feature maps at full image resolution (R). The Nth residual stream (N>0) as used in MRRN is generated by N pooling operations and carries feature maps at R/2N resolution.

CNN Block includes 3×3 convolutions, batch normalization (BN) and ReLU activation and is used for feature extraction.

Residual Unit or RU is a convolutional layer with residual connection placed at the beginning and at the end of the network like the FRRN.

Residual Connection Unit (RCU) is the work horse for the network where the feature maps are computed through a sequence of convolutions using CNN blocks.

Residual Connection Unit Block (RCUB) includes sequentially connected RCUs.

The residual connection unit (RCU) constitutes the filters used in each layer. The structure of an RCU is shown in (a) of FIG. 1B. RCU has two inputs, namely, residual stream feature map and regular CNN feature map and two outputs, namely, the regular and residual feature maps. The residual stream input includes feature maps from one of the preceding higher resolution residual streams. The residual feature map input is downsampled through pooling and then concatenated with the regular CNN feature map computed from the previous layer. An RCU is composed of one or more CNN blocks (FIG. 1). The CNN blocks output the processed regular feature map that is passed as input to the subsequent RCU block or the next CNN layer. The residual output is computed through a 1×1 convolution with upsampling of the regular output and passed back to the corresponding residual input stream. In summary, the RCU residually connects feature maps from residual streams and the feature maps at particular resolutions and jointly learns features between different residual streams to refine features computed at lower resolution.

The RCU block (RCUB) is composed of sequentially connected RCUs. Two different RCU blocks can be distinguished, namely, the incremental RCU block and the dense RCU block based on their inputs and the number of RCUs used in those blocks.

An incremental RCUB consists of serially connected RCUs. Each RCU successively refines feature maps of increasing feature resolution starting from the nearest lower stream up to the 0th stream. FIG. 1B depicts an example of incremental RCU block at 2nd residual stream. The dot-solid arrow (see legend) is an abstraction that represents a bi-directional connection between the residual stream and the current layer. RCU blocks are only placed in streams that can have input from at least one residual stream. Therefore, the 0th residual stream does not contain an RCU block. RCU×3 were used in the first residual stream like the FRRN. A residual stream produced using N (N>1) pooling operations contains (N+1) RCUs in its RCU block. The first RCU in an RCU block is residually connected to the 0th stream to use the full resolution information. The subsequent RCUs are sequentially connected to the residual streams of increasing spatial resolution starting from the immediately preceding residual stream.

Unlike the incremental RCUB, every dense RCUB integrates information residually only from the immediate higher spatial resolution feature maps. The additional RCU blocks in a residual stream further refine the feature maps computed at that stream thereby, resulting in dense residual feature maps. Each RCUB has 2 RCUs to refine features from preceding residual stream with the feature maps at current resolution.

Figure 1C:
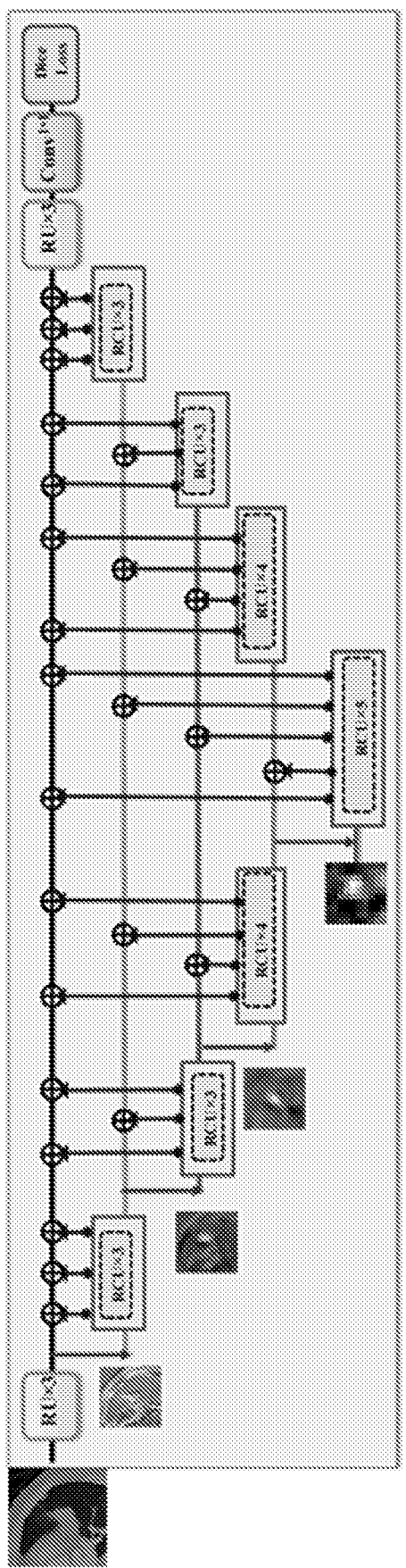
FIG. 1C is a block diagram depicting an incremental MRRN.
Figure 1D:
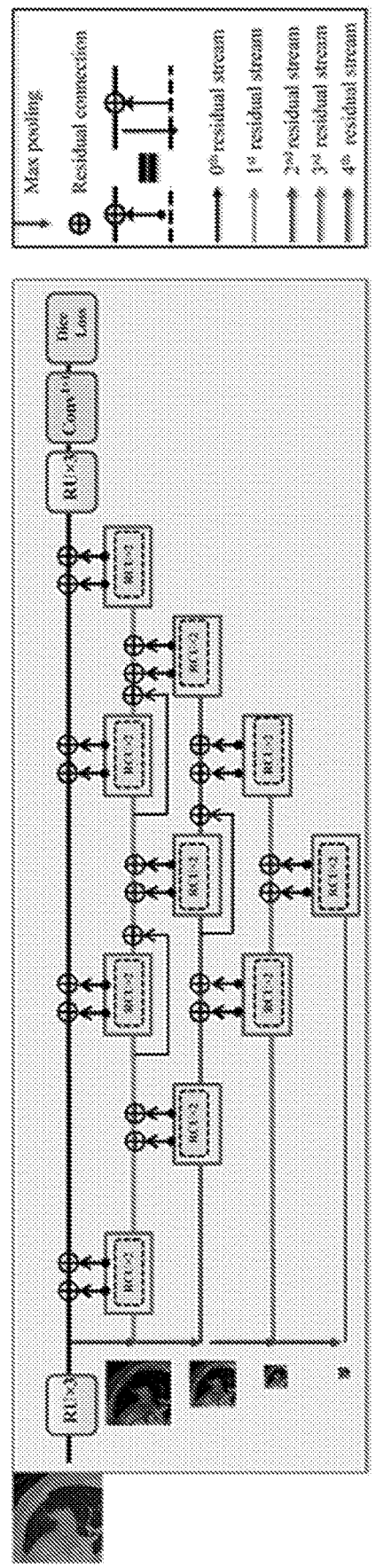
FIG. 1D is a block diagram depicting a dense MRRN.

Incremental MRRN is composed of multiple incremental RCUB and residual feature streams (FIG. 1C). The two ends of all residual streams except the 0th and the last stream contain two RCUB to encode and decode the information. The 0th residual stream does not contain any RCUB while the last stream contains one RCUB. Feature integration from multiple resolutions obviates the need for additional unpooling following RCUBs as used in conventional encoder-decoder like the Unet. The incremental MRRN at a given layer n with multiple residual feature streams k (=0, 1, N), preceding n is defined as:

$$z_n^k = z_{n-1}^k + H(y_{f(n,k)-1}^{p(n-1,k)}, z_{n-1}^k; W_n^k)$$

$$y_{f(n,k)}^{p(n,k)} = G(y_{f(n,k)-1}^{p(n-1,k)}, z_{n-1}^k; W_n^k) \quad k=0,1,\ldots N, \qquad (1)$$

where, N is the total number of residual feature streams at n; $z_n$ is the n-th residual connection of kth feature stream; $y_{f(n,k)}^{p(n,k)}$ is the output produced by concatenating $z_n$ with p(n,k)-th residual feature stream after f(n,k) RCU connection (see Table I(c)). Note that (1) is identical to the FRRN formulation following the first pooling operation when k=0. The number of residual connections to RCUB increase and decrease with addition of pooling and unpooling operations, respectively.

The backpropagated loss/is computed by taking the derivative with respect to the weights $W_{n-1}$ at layer n as:

$$\begin{aligned}\frac{\partial l}{\partial W_{n-1}^k} &= \frac{\partial l}{\partial y_{f(n-1,k)}^{p(n-1,k)}} \frac{\partial y_{f(n-1,k)}^{p(n-1,k)}}{\partial W_{n-1}^k} + \frac{\partial l}{\partial z_{n-1}^k} \frac{\partial z_{n-1}^k}{\partial W_{n-1}^k} \\ &= \frac{\partial l}{\partial y_{f(n-1,k)}^{p(n-1,k)}} \frac{\partial y_{f(n-1,k)}^{p(n-1,k)}}{\partial W_{n-1}^k} + \frac{\partial z_n^k}{\partial W_n^k} \frac{\partial l}{\partial z_n^k} \frac{\partial z_n^k}{\partial z_{n-1}^k} \\ &= \frac{\partial l}{\partial y_{f(n-1,k)}^{p(n-1,k)}} \frac{\partial y_{f(n-1,k)}^{p(n-1,k)}}{\partial W_{n-1}^k} + \\ &\quad \frac{\partial z_n^k}{\partial W_n^k}\left(\frac{\partial l}{\partial z_n^k} + \frac{\partial l}{\partial z_n^k}\frac{\partial H(y_{f(n,k)-1}^{p(n-1,k)}, z_{n-1}^k; W_n^k)}{\partial z_{n-1}^k}\right) \\ &= \frac{\partial l}{\partial y_{f(n-1,k)}^{p(n-1,k)}} \frac{\partial y_{f(n-1,k)}^{p(n-1,k)}}{\partial W_{n-1}^k} + \end{aligned} \qquad (2)$$

-continued $$\frac{\partial z_n^k}{\partial W_n^k}\left(\frac{\partial l}{\partial z_n^k} + \frac{\partial l}{\partial z_n^k}\frac{\partial H(y_{f(n-1,k)}^{p(n-1,k)}, z_{n-1}^k; W_n^k)}{\partial y_{f(n,k)-1}^{p(n-1,k)}}\cdot\right.$$

$$\left.\prod_{i=f(n-1,k)}^{f(n,k)-1}\frac{\partial G(y_i)}{\partial y_i}\times\frac{\partial y_{f(n-1,k)}^{p(n-1,k)}}{\partial z_{n-1}^k}\right)$$

As seen, the gradient $$\frac{\partial l}{\partial z_n^k}$$

is independent of depth similar to the FRRN formulation. However, the formulation adds an addition term $$\prod_{i=f(n-1,k)}^{f(n,k)-1}\frac{\partial G(y_i)}{\partial y_i}$$

to further constrain weight update and regularize learning.

Dense MRRN uses down-sampled feature maps computed at image resolution as input to the first RCUB in all streams (FIG. 1D) to produce dense residual streams. Similar to incremental MRRN, the 0th residual stream does not contain RCUB. All other residual streams have as many intermediate RCUBs corresponding to the number of following residual streams placed in between the end RCUBs. The feature maps are computed as:

$$z_n^k = z_{n-1}^k + H(z_{n-1}^k, z_n^{k+1}; W_n^k)$$

$$z_{n'}^{k+1} = z_{n'-1}^{k+1} + H(z_{n'-1}^{k+1}, z_{n'k+2}; W_n^{k+1}), \quad (3)$$

where $W_n^k$ is the parameter of nth RCU output refined using residual stream k (Table I (d)). The derivative of the loss l with respect to $W_{n-1}^k$ is calculated as:

$$\frac{\partial l}{\partial W_{n-1}^k} = \frac{\partial l}{\partial z_{n-1}^k}\frac{\partial z_{n-1}^k}{\partial W_{n-1}^k} + \frac{\partial l}{\partial z_{n'-1}^k}\frac{\partial z_{n'-1}^k}{\partial W_{n-1}^k} \quad (4)$$

$$= \frac{\partial l}{\partial z_{n'-1}^k}\frac{\partial z_{n'-1}^k}{\partial W_{n-1}^k} + \frac{\partial z_{n-1}^k}{\partial W_{n-1}^k}\frac{\partial l}{\partial z_n^k}\frac{\partial z_n^k}{\partial z_{n-1}^k}$$

$$= \frac{\partial l}{\partial z_{n'-1}^k}\frac{\partial z_{n'-1}^k}{\partial W_{n-1}^k} +$$

$$\frac{\partial z_{n-1}^k}{\partial W_{n-1}^k}\left(\frac{\partial l}{\partial z_n^k} + \frac{\partial l}{\partial z_n^k}\frac{\partial H(z_{n-1}^k, z_{n'}^{k+1}; W_n^k)}{\partial z_{n-1}^k}\right)$$

$$= \frac{\partial l}{\partial z_{n'-1}^k}\frac{\partial z_{n'-1}^k}{\partial W_{n-1}^k} + \frac{\partial z_{n-1}^k}{\partial W_{n-1}^k}$$

$$\left(\frac{\partial l}{\partial z_n^k} + \frac{\partial l}{\partial z_n^k}\frac{\partial H(z_{n-1}^k, z_{n'}^{k+1}; W_n^k)}{\partial z_{n-1}^k}\frac{\partial z_{n'}^{k+1}}{\partial z_{n-1}^k}\right)$$

$$= \frac{\partial l}{\partial z_{n'-1}^k}\frac{\partial z_{n'-1}^k}{\partial W_{n-1}^k} + \frac{\partial z_{n-1}^k}{\partial W_{n-1}^k}\frac{\partial l}{\partial z_n^k}$$

$$\left(\frac{\partial l}{\partial z_n^k} + \frac{\partial l}{\partial z_n^k}\frac{\partial H(z_{n-1}^k, z_{n'}^{k+1}; W_n^k)}{\partial z_{n-1}^k}\cdot\frac{\partial z_{n'}^{k+1}}{\partial z_{n'-1}^k}\frac{\partial z_{n'-1}^{k+1}}{\partial z_{n-1}^k}\right)$$

$$= \frac{\partial l}{\partial z_{n'-1}^k}\frac{\partial z_{n'-1}^k}{\partial W_{n-1}^k} + \frac{\partial z_{n-1}^k}{\partial W_{n-1}^k}\frac{\partial l}{\partial z_n^k}$$

$$\left(\frac{\partial l}{\partial z_n^k} + \frac{\partial l}{\partial z_n^k}\frac{\partial H(z_{n-1}^k, z_{n'}^{k+1}; W_n^k)}{\partial z_{n-1}^k}\cdot\right.$$

$$\left.\left(1 + \frac{\partial H(z_{n'-1}^k, z_{n''}^{k+1}; W_{n'}^{k+1})}{\partial z_{n'-1}^k}\right)\frac{\partial z_{n-1}^{k+1}}{\partial z_{n-1}^k}\right),$$

where, $$\left(1 + \frac{\partial H(z_{n'-1}^{k+1}, z_{n''}^{k+2}; W_{n'}^{k+1})}{\partial z_{n'-1}^k}\right)$$

results from the presence of intermediate RCUBs.

The networks were trained using the Tensorflow library on Nvidia GTX 1080Ti with 12 GB memory processor. A kernel size of 3×3 with 32 features was used to produce features following the $0^{th}$ residual stream. The number of features was increased at a rate of $2^k+5$ with each additional pooling ultimately resulting in 28,620,001 parameters for incremental MRRN and 25,542,241 parameters for dense MRRN. A batch size of 16 was used due to GPU memory constraints and employed the ADAM algorithm with the initial learning rate of $1e^{-4}$. Early stopping with a maximum epoch number of 100 was used to prevent overfitting. To reduce the impact of data imbalance during training, the DSC loss was used, which is defined as:

$$L_{DSC} = 1 - \frac{2\sum_i p_i g_i}{\sum_i p_i + \sum_i p_i}, \quad (5)$$

where $p_i \in [0,1]$ represents the $i^{th}$ output of the last layer and $g_i \in [0,1]$ is the ground truth label. Additionally, real-time data augmentation was used during training by using image flipping, shifting, elastic deformation, with Gaussian noise.

The final volumetric segmentation was obtained by combining the segmentations from the individual 2D slices using connected components extraction. No additional post-processing of the segmentations was performed.

Experimental Setup

Three datasets were used for the analysis, namely, the open-source The Cancer Imaging Archive (TCIA) dataset of 377 NSCLC scanned at the MAASTRO clinic, internal institution (MSKCC) dataset of 304 tumors from 50 NSCLC patients treated with PD-1 inhibitor immunotherapy using pembrolizumab, and the Lung Image Database Consortium (LIDC) dataset consisting of 2669 nodules from 1018 patients from seven different institutions.

The tumors in the TCIA and MSKCC were confirmed advanced stage malignant tumors while those from the LIDC were lung nodules (>3 mm and confirmed by at least 1 radiologist) with varying degrees of malignancy. The MSKCC dataset also included longitudinal CT scans imaged before and every 9 weeks during therapy up to a maximum of 17 weeks after treatment initiation. The training (TCIA) and validation set (MSKCC) consisted of contrast enhanced CT scans while the testing set from the LIDC included both regular dose and low-dose CT images. Tumor contours for the TCIA were verified and edited when necessary by radiologist. All ground truth tumor contours in the MSKCC dataset were confirmed by a chest radiologist with several years of experience reviewing chest CT images. The LIDC datasets were manually delineated by four radiologists who also assigned a malignancy score between 1-5 with 1 being low and 5 being high malignancy. Out of 2669, 928 were confirmed and delineated by all four radiologists and were at least 3 mm in diameter. 529 nodules of the 928 that were assigned an average malignancy score of >3 were analyzed. This resulted in a total of 1210 analyzed tumors from all the three datasets.

There was a wide variation in the size and distribution of tumors between the datasets. The tumors in the TCIA dataset ranged in size from 1.88 cc to 1033 cc, MSKCC from 2.96 cc to 413.8 cc, and the LIDC from 0.031 cc to 19.18 cc (all calculated according to radiologist delineation). The distributions of tumor sizes discretized by size are shown in Table I. Finally, predominant lesions in the TCIA and MSKCC dataset were in the mediastinum or attached to chest wall while the tumors in LIDC were the most frequent in the lung parenchyma (Table II).

TABLE I

TUMOR SIZES IN THREE DIFFERENT DATASETS (TCIA, MSKCC AND LIDC)

| Group | Tumor size range(cm³) | TCIA | MSKCC | LIDC |
|---|---|---|---|---|
| Very small (VS) | [0, 1) | 8 | 38 | 324 |
| Small (S) | [1, 5) | 57 | 75 | 164 |
| Medium (M) | [5, 10) | 41 | 56 | 38 |
| Large (L) | [10, 20) | 44 | 51 | 3 |
| Very large (VL) | >20 | 227 | 84 | 0 |

TABLE II

TUMOR LOCATION IN THREE DIFFERENT DATASETS (TCIA, MSKCC AND LIDC)

| Tumor Location | TCIA | MSKCC | LIDC |
|---|---|---|---|
| Within lung parenchyma | 103 | 89 | 387 |
| Abutting to mediastinum | 157 | 104 | 6 |
| Attached to chest wall | 117 | 111 | 136 |

The TCIA dataset was used as the training cohort as it had the largest tumors and contained many difficult to detect tumors such as those attached to the mediastinum and the chest wall. The MSKCC dataset was used as validation set for selecting the best model. The LIDC dataset was used as an independent test set. Additionally, K=5 fold cross-validation was performed on the TCIA dataset with part of the data withheld to evaluate and report accuracy on the data not used for training.

Training was performed using patches of size 160×160 or region of interest (ROI) centered on the tumor. All ROIs were resized to the size of 160×160 resulting in a total number of 57793 training image samples followed by data augmentation as described previously.

The absence of any fully connected layer enables evaluation of images of sizes other than the 160×160 used in training. The MSKCC and LIDC datasets consisted of 256×256 and 160×160 images, respectively. Detections from individual slices were then stacked into full volumetric segmentation through connected components extraction.

Random forest with fully connected conditional random field (RF+fCRF): A random forest (RF) classifier was implemented with fully connected conditional random field (CRF) approach for the lung tumor segmentation. Maximum CT intensity, minimum CT intensity, mean minimum CT intensity, mean gradient, standard deviation gradient, entropy and Gabor edge features were used at angles ($\theta=0$, $\pi/4$, $\pi/2$, $3\pi/4$) at bandwidth of ($\gamma=0.1, 0.2, 0.3, 0.4$). The RF classifier was trained with (k=5) fold cross-validation using 50 trees and maximum depth of 30. Voxel-wise RF classifications were refined by a fully connected CRF.

Unet is a commonly used neural network for medical image segmentation and has been applied on a variety of medical image segmentation tasks including in liver, and breast. The fully connected layer was not used as proposed in to enable application of the network for segmenting images of varying sizes.

The SegNet that combines an encoder and decoder structure was used. The encoder network consists of 13 convolutional layers as the first 13 convolutional layers in the VGG16 network and a corresponding number of decoder layers.

FRRN can be considered as a special case of the proposed methods where the FRRN uses only the 0th residual stream (carrying full resolution feature).

The segmentation accuracy was quantitatively analyzed using Dice overlap coefficient (DSC), sensitivity, precision, and Hausdorff distance. The DSC calculates the overlap between the segmentation results and ground truth, and is defined as:

$$DSC = \frac{2TP}{FP + 2TP + FN}, \quad (6)$$

where, TP is the number of true positives, FP is the number of false positives and FN is the number of false negatives. Sensitivity and precision metrics were computed as, $$\text{Sensitivity} = \frac{TP}{TP + FN}, \quad (7)$$

$$\text{Precision} = \frac{TP}{TP + FP}, \quad (8)$$

The Hausdorff distance is defined as:

$$\text{Haus}(P, T) = \max\{\sup_{p \in S_P} \inf_{t \in S_T} d(p, t), \sup_{t \in S_T} \inf_{p \in S_P} d(t, p)\}, \quad (9)$$

where, P and T are ground truth and segmented volumes, and p,t are points on P and T, respectively. $S_P$ and $S_t$ correspond to the surface of P and T, respectively. The Hausdorff Distance (95%) was used to remove undue influence of outliers.

The tumor detection rate of the analyzed methods was evaluated by using segmentation overlap threshold T determined using the DSC metric. Tumors were considered detected when the overlap between the segmentation and ground truth was at least r, computed as, $$\tau = \frac{TP}{N}, \quad (10)$$

where, TP is the true positives and N is the total number of ground truth tumor pixels. Tumor detection rate is then $$\text{Rate} = \frac{D_{tumor}}{N_{tumor}}, \quad (11)$$

where, $D_{tumor}$ is the detected tumor number and $N_{tumor}$ is the total tumor numbers.

Thirty-six patients in the MSKCC dataset were imaged at multiple times (>3) starting from baseline and during treatment (every 9 weeks) with immunotherapy. Only the best performing segmentation method was used for this analysis. The relative volume with respect to the baseline volume (v0) was computed as:

$$v'_i = \frac{v_i}{v_0}, \quad (12)$$

where, v, is the volume at the time t=i. Next, the average slope of the relative volumes was calculated from baseline to the last available imaged time (t ranged from 3 to 13) for both the expert and the algorithm segmentations. The two trends were compared statistically using paired Student's T-test.

The impact of features from the residual feature streams was evaluated using weight sparsity with respect to layer depths for FRRN, incremental MRRN and dense MRRN. These three methods were selected as these are the only ones that used residual streams. The weight sparsity was defined as:

$$S_i = \frac{N_i(|w|<T)}{N_i}, \quad (13)$$

where $N_i(|w<T|)$ is the number of weights whose absolute value is less than a threshold T and N, is the total number of weights in layer of depth i. Larger sparsification at a certain layer indicates that fewer features from that layer are used which in turn means that those features have lower impact on the performance of the network compared to another layer with smaller sparsification.

Figure 1E:
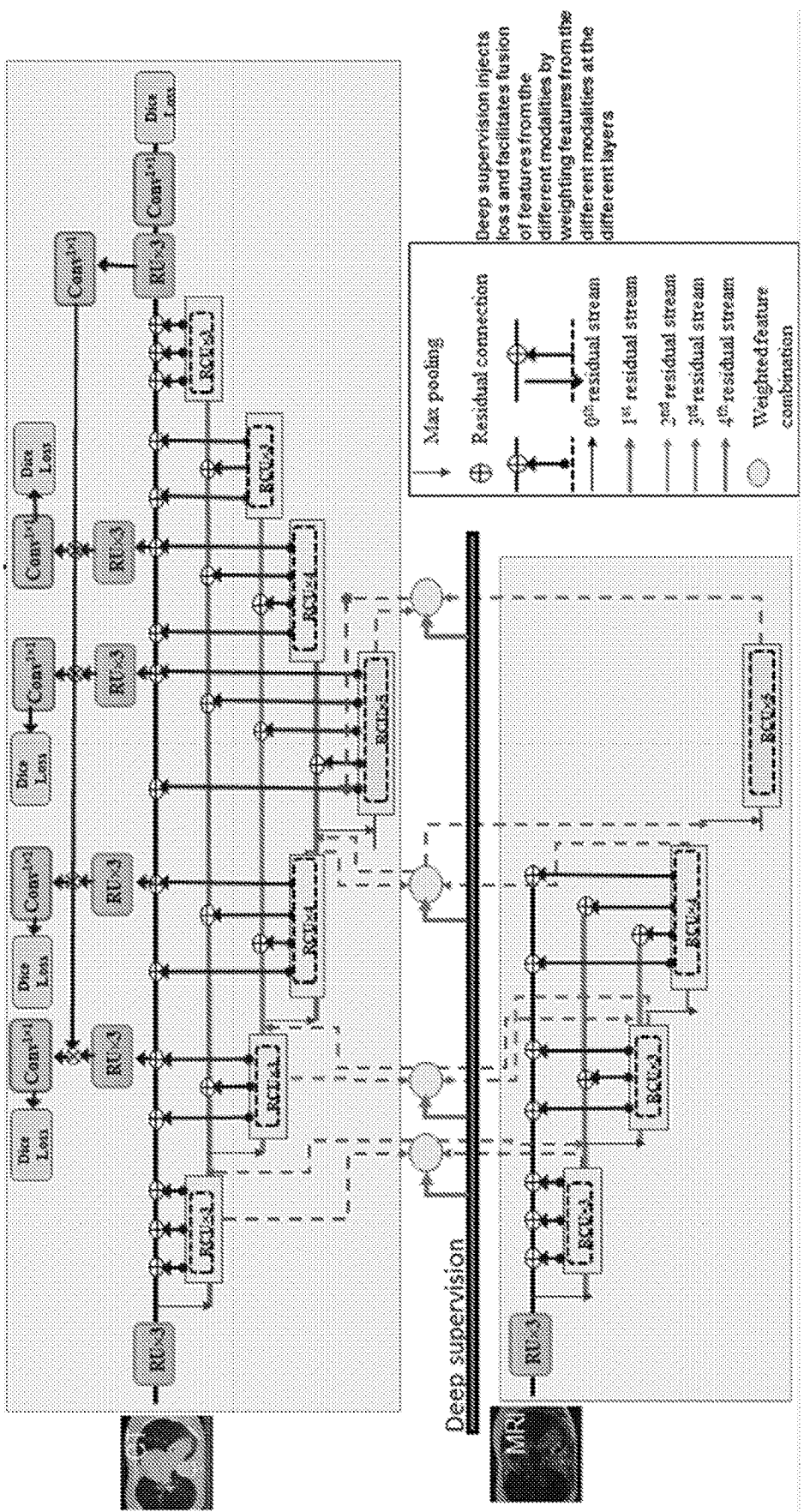
FIG. 1E is a block diagram depicting a network architecture for deep multi-modal resolution residual network (MMRRN)

FIG. 1E shows a multi-modal (integrating CT and MR) neural network for tumor and normal organs at risk of radiation from radiotherapy treatments. The network architecture simultaneously combines features from multiple image resolutions and levels, namely low level (edges, and local textures), mid-level (local appearance within and between structures), and high-level (long-range spatial dependencies between structures) for tumor and OAR segmentation. Deep supervision losses automatically select relevant features at different levels and resolutions for individual structures segmentation. Deep supervision-based dynamic feature fusion from multiple modalities from different network layers for specific structures. Deep supervision adds an attention mechanism to dynamically weight the deep supervision loss in a pixel-level and channel wise. This mechanism can further faster the training convergence and prevents over-fitting.

Figure 1F:
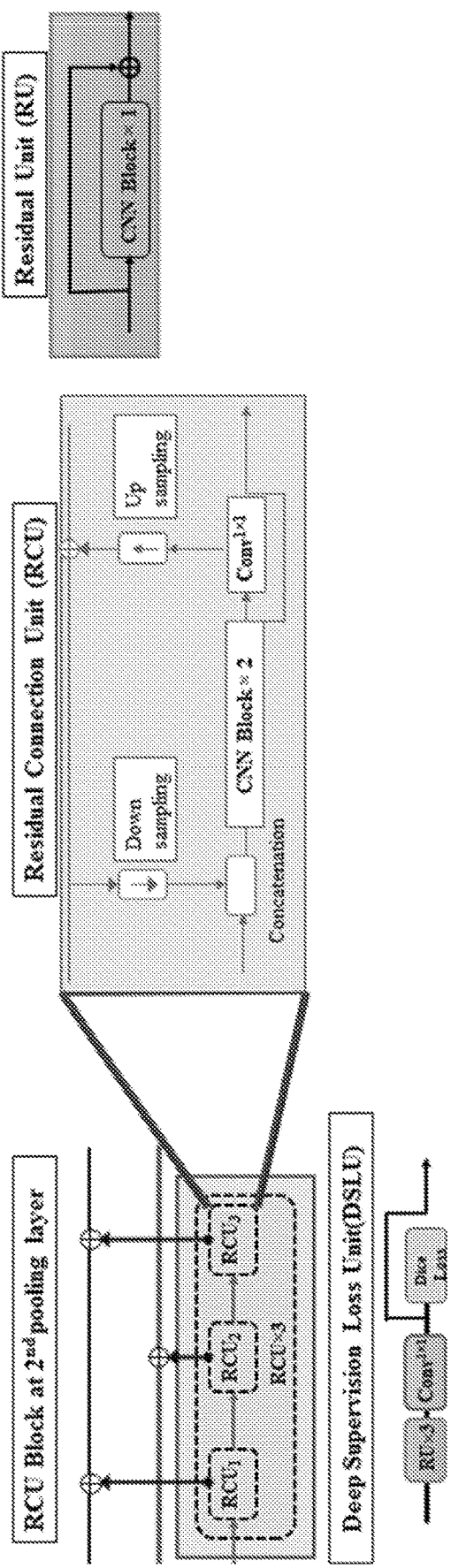
FIG. 1F is a block diagram depicting a network architecture for joint CT-MRI segmentation.
Figure 1G:
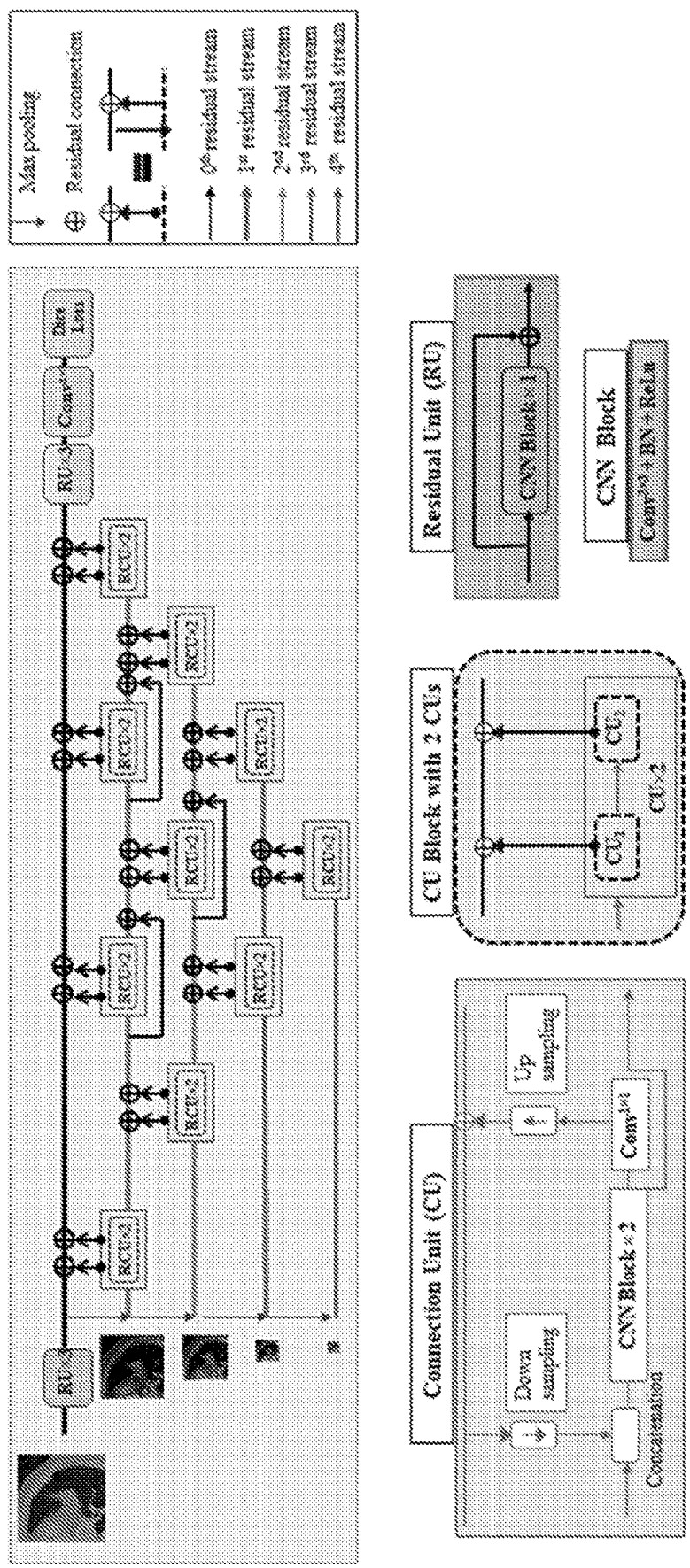
FIG. 1G is a block diagram depicting an architecture using dense residual connections for single modality.

FIG. 1F depicts a joint CT-MRI segmentation method that combines automatically extracted features from various feature levels and resolutions. The deep learning method learns the set of filters for computing the features and how information from the two modalities should be combined at various feature levels automatically for each problem. In other words, appropriate features and combination of features from the two modalities are learned for the different structures. Unlike methods that perform testing feature fusion at all possible layers by specifically tying feature blocks (in computer vision applications), this approach dynamically configures and learns how to fuse features from CT and MRI. This is the first approach to accomplish dynamically configured feature fusion facilitated through deep supervision. Deep supervision passes auxiliary losses to the individual feature layers across the network and regularizes learning which helps the approach to maximize learning capacity from the smaller number of examples. FIG. 1G shows an architecture using dense residual connections for single modality.

Figure 1H:
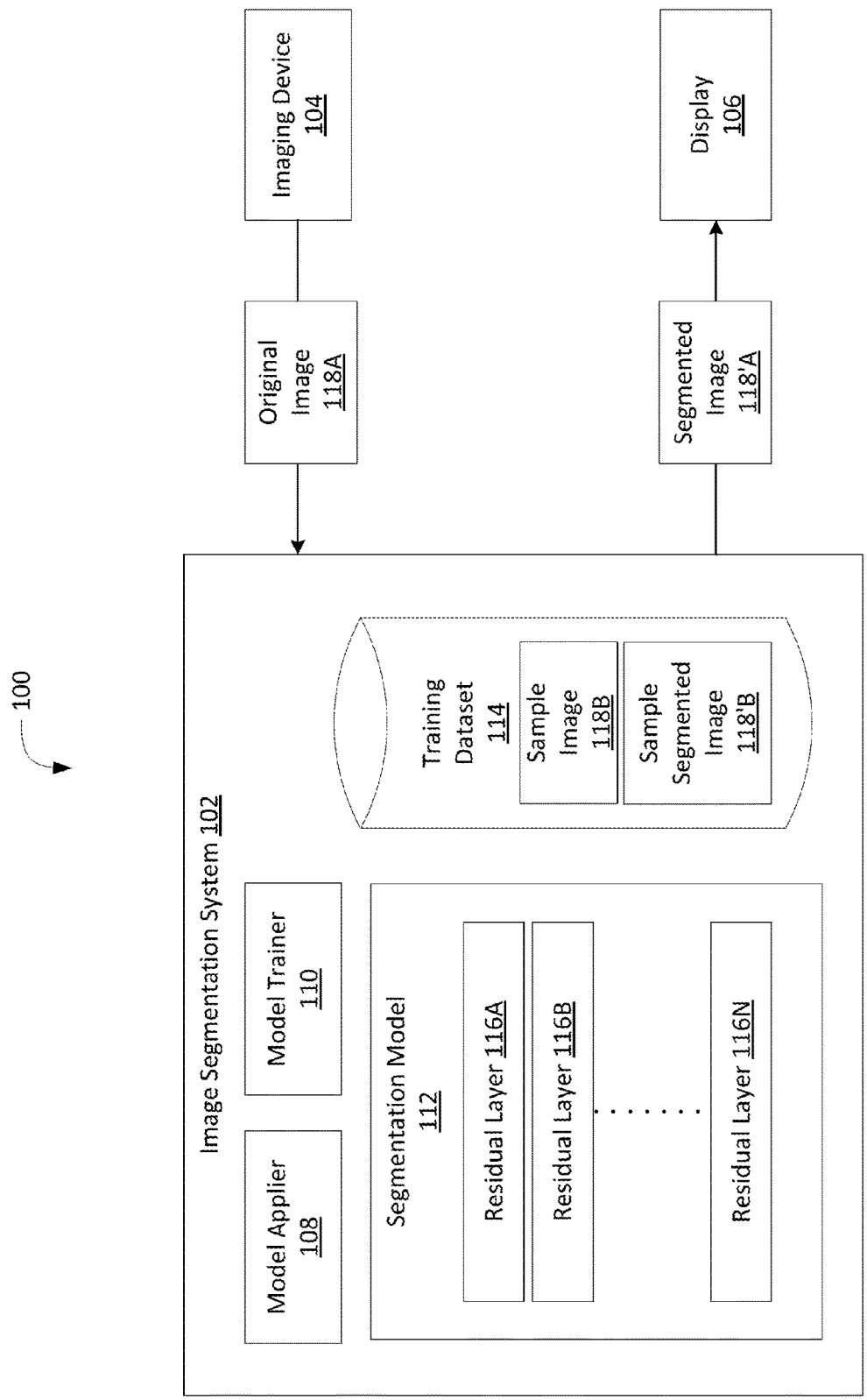
FIG. 1H is a block diagram of an example system for segmenting biomedical images using multi-resolution neural networks.

FIG. 1H depicted is a block diagram of a system 100 for segmenting biomedical images using multi-resolution residual neural networks (MRRNs). In overview, the system 100 may include an image segmentation system 102, at least one imaging device 104, and at least one display 106. The image segmentation system 102 may be communicatively coupled with the imaging device 104 and the display 106. The image segmentation system 102 may include a model applier 108, a model trainer 110, a segmentation model 112, and a training dataset 114, among others. The segmentation layer 112 may maintain or otherwise include a set of residual layers 116A-N (herein referred to generally as residual layers 116). Each of the components in the system 100 listed above may be implemented using hardware (e.g., one or more processors coupled with memory) or a combination of hardware and software as detailed herein in Section E. Each of the components in the system 100 may implement or execute the functionalities detailed herein in Section A, such as those described in conjunction with FIGS. 1A-G, and Section C.

The imaging device 104 may perform a biomedical imaging scan on a subject to acquire or generate at least one tomographic biomedical image 118A (hereinafter generally referred to as original image 118). The imaging device 104 may be in any modality of biomedical imaging. The imaging device 104 may include a PET-computed tomography (CT) scanner, an X-ray CT Scanner, a SPECT CT scanner, an MRI scanner, an ultrasound scanner, and a photoacoustic scanner, among others. To scan, the imaging device 104 may be pointed toward a designated area on an outer surface of the subject (e.g., human or animal). As the subject is scanned, the imaging device 104 may generate a projection dataset corresponding to the original image 118. The project dataset may correspond to a cross-sectional plane or a volume of the subject through the predesignated area. The projection dataset may be two-dimensional or three-dimensional visualized representation of the subject, including the inner anatomical and physiological structure of the subject.

The projection dataset may include one or more data counts. The projection dataset may include the one or more data counts in accordance with any data structure, such as an array, a binary tree, a matrix, a linked list, a heap, a hash table, a stack, or a queue, among others. Each data count may correspond to a coordinate of the scanned cross-sectional plane or the volume of the subject. When the cross-sectional plane of the subject is scanned, the projection dataset may be two-dimensional and the coordinates of the data counts may also be two-dimensional. When the volume of the subject is scanned, the projection dataset may be three-dimensional and the coordinates for the data counts may also be three-dimensional. The number of data counts in the projection dataset may depend on a sampling rate of the biomedical imaging scan performed by the imaging device 104.

The original image 118 may have or may be of a set image resolution (sometimes herein referred to as a full or original image resolution). The image resolution of the original image 118 may be set or defined by the imaging device 104. The image resolution may be two-dimensional (e.g., N×M), when the scan corresponds to a cross-sectional plane of the subject acquired by the imaging device 104. The image resolution may be three-dimensional (e.g., N×M×O), when the scan corresponds to a volume of the subject acquired by the imaging device 104. The image resolution for the original image 118 may be measured in a number of pixels per dimension. The image resolution may also be measured in the number of data counts per dimension of the original image 118.

The display 106 may present or render an image (e.g., a segmented tomographic biomedical image 118'B) output by the image segmentation system 102. In some embodiments, the display 106 may present or render the reconstructed image generated by the CED model 212 of the image segmentation system 102. The display 106 may include any monitor, such as a liquid crystal display (LCD), an organic light-emitting diode (OLED) monitor, and a cathode ray tube (CRT), among others. The display 106 may be communicatively coupled with the image segmentation system 102, and may render and output the image from the image segmentation system 102.

The model applier 108 may receive, obtain, or otherwise identify at least one original image 118 for segmentation. The model applier 108 may have a runtime mode and a training mode. In runtime mode, the model applier 108 may identify the original image 118 acquired by the imaging device 104. In training mode, the model applier 108 may identify from the training dataset 114. The retrieved training dataset 114 may include a sample original tomographic biomedical image 118B (referred herein also generally as the original image 118). The sample original image 118 of the training dataset 114 may be of the same resolution as the original image 118 from the imaging device 104.

In some embodiments, the model applier 108 may change, alter, or otherwise modify the image resolution of the original image 118. The model applier 108 may measure or identify the initial image resolution of the original image 118 acquired from the imaging device 104 or from the training dataset 114. The model applier 108 may compare the initial image resolution to a permitted image resolution for inputs to the segmentation model 112. The permitted image resolution may define the image resolution compatible as inputs to the segmentation model 112. Based on the comparison, the model applier 108 may resize the original image 118 to match the permitted image resolution for the segmentation mode 112. When the initial image resolution is determined to be greater than the permitted image resolution, the model applier 108 may reduce the image resolution of the original image 118 to match the permitted image resolution (e.g., using down-sampling). Conversely, when the initial image resolution is determined to be less than the permitted image resolution, the model applier 108 may increase the image resolution of the original image 118 to match the permitted resolution (e.g., using up-sampling).

In conjunction, the model applier 108 (or the model trainer 110 or both) may establish and maintain the segmentation model 112 and the one or more residual layers 116 of the segmentation model 112. The segmentation model 112 may have the original image 118 as an input. The segmentation model 112 may have a segmented tomographic biomedical image 118'A (hereinafter generally referred to as the segmented image 118') as the output. The details of the functionalities and structures of the segmentation model 112 are further provided herein in conjunction with FIGS. 1A-G and 1I-N.

Figure 1I:
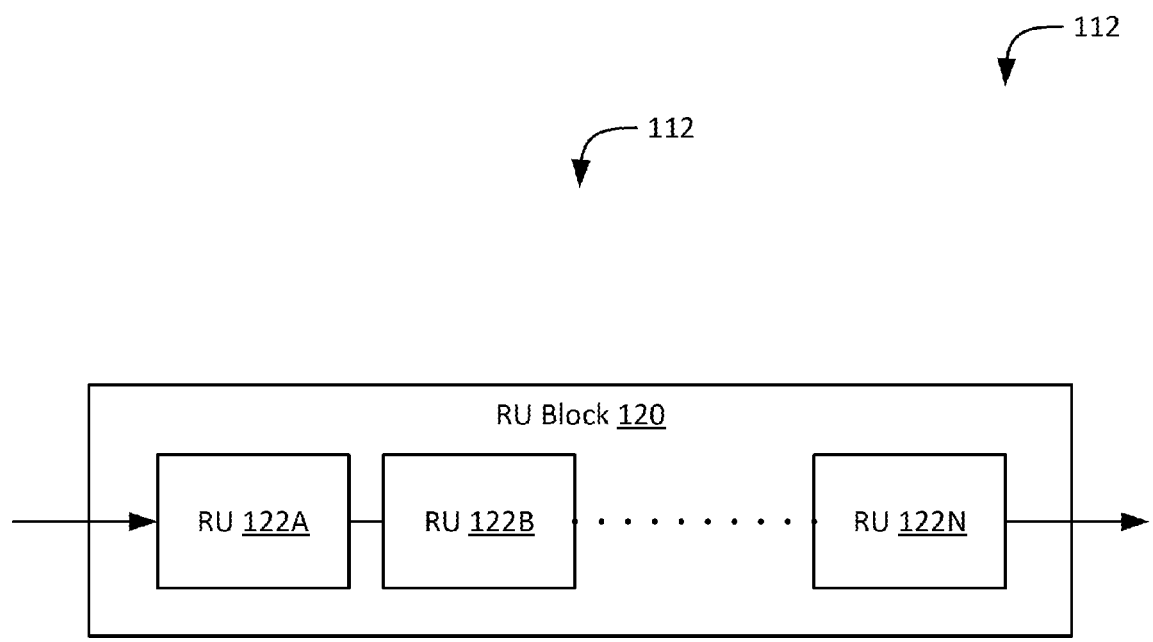
FIG. 1I is a block diagram of an example residual unit block of the system for segmenting biomedical images.

FIG. 1I depicts a block diagram of a residual unit (RU) block 120 of the segmentation model 112 in at least one of the residual layers 116. The RU block 120 can be included in at least the first residual layer 116A. The RU block 120 can have at least one input and at least one output. The input can include the original image 118 or a set of feature maps generated by processing the original image 118. The output can include a set of feature maps processed by the RU block 120. The RU block 120 can have a set of RUs 122A-N (hereinafter generally referred to as RUs 122). The set of RUs 122 can be arranged in series (e.g., as depicted) or parallel configuration, or in any combination. In a series configuration, the input of one RU 122 may include the output of the previous RU 122 (e.g., as depicted). In parallel configuration, the input of one RU 122 may include the input of the entire RU block 120. The RU block 120 can have one or more RUs 122. For example, the RU block 120 can have three to five RUs 120.

Figure 1J:
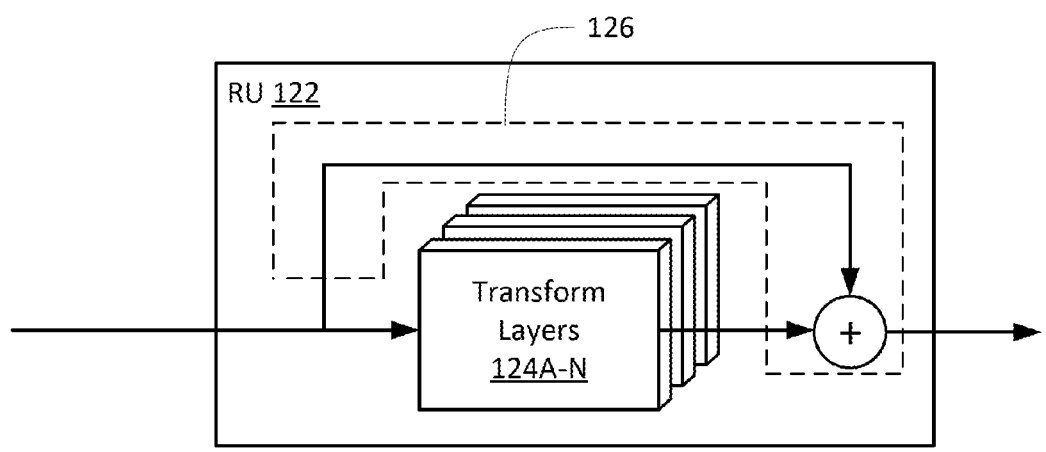
FIG. 1J is a block diagram of an example residual unit of the system for segmenting biomedical images.

FIG. 1J depicts a block diagram of a residual unit (RU) 122 of the residual unit (RU) block 120 in the segmentation model 112. Each RU 122 in the RU block 120 can have a set of transform layers 124A-N (hereinafter generally referred to as transform layers 124) and at least one skip aggregator operator 126. The set of transform layers 124 can include one or more parameters (e.g., weights) to modify or otherwise process the set of feature maps inputted into the RU 122 to produce or generate an output set of features. The set of transform layers 124 can be arranged in series, with an output of one transform layer 124 fed as an input to a succeeding transform layer 124. Each transform layer 124 may have a non-linear input-to-output characteristic. In some embodiments, the set of transform layers 124 may be a convolutional neural network (CNN), including a convolutional layer, a normalization layer, and an activation layer (e.g., a rectified linear unit (ReLU)), among others. The skip aggregator operator 126 can combine the output set of feature maps from the set of transform layers 124 and the original input set of feature maps to generate an output set of feature maps for the RU 122. The combination may include addition, concatenation, or a weighted summation, among others. In some embodiments, the skip aggregator 126 can concatenate the output from the set of transform layers 124 with the input into the RU 122 to generate the output set of feature maps.

Figure 1K:
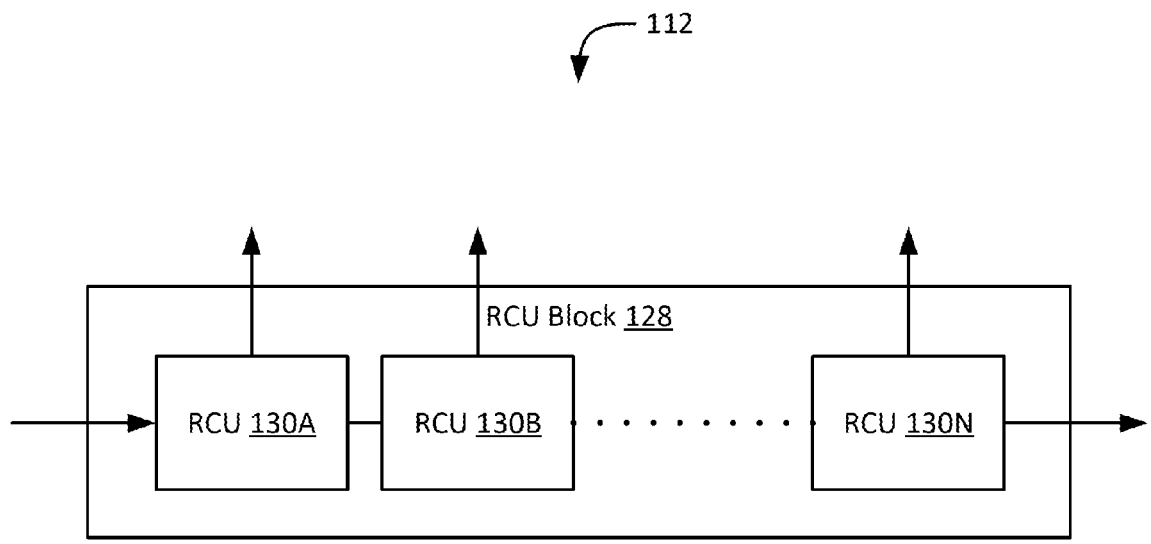
FIG. 1K is a block diagram of an example residual connection unit block of the system for segmenting biomedical images.

FIG. 1K depicts a block diagram of a residual connection unit (RCU) block 128 of the segmentation model 112 in at least one of the residual layers 116. The RCU block 128 can be included into the second residual layer 116B and the successive residual layer 116C-N. The RCU block 128 can have a set of RCUs 130A-N (hereinafter generally referred to as RCUs 130). The input can include a set of feature maps generated by processing the original image 118 from the same residual layer 116 as the RCU block 128 and feature maps from one of previous residual layers 116. For example, the input of the RCU block 128 on the third residual layer 116C can include feature maps from the first residual layer 116A or the second residual layer 116B. The output can include sets of feature maps, each processed and outputted by one of the RCUs 130, to be fed forward the same residual layer 116 and feature maps to one of the previous residual layer 116. For example, the output of the RCU block 128 on the second residual layer 116C can include feature maps forwarded on the same, second residual layer 116B and feature maps to be fed into the first residual layer 116A. The number of sets of feature maps outputted by the RCU block 128 can be at least the number of RCUs 130 in the RCU block 128. The set of RUs 132 can be arranged in series (e.g., as depicted) or parallel configuration, or in any combination. In a series configuration, the input of one RCU 130 may include the output of the previous RCU 130 (e.g., as depicted). In parallel configuration, the input of one RCU 130 may include the input of the entire RCU block 128. The RCU block 128 can have one or more RCUs 130. For example, the RCU block 128 can have three to five RUs 130.

Figure 1L:
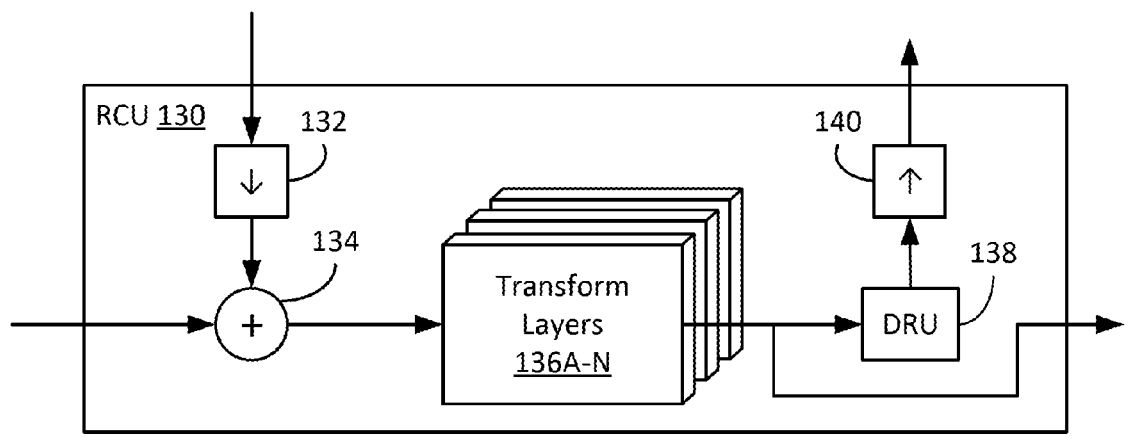
FIG. 1L is a block diagram of an example residual connection unit of the system for segmenting biomedical images.

FIG. 1L depicts a block diagram of a residual connection unit (RCU) 130 of the residual connection unit block 128. Each RCU 130 of the RCU block 128 may include one or more inputs and one or more outputs. One of the inputs of the RCU 130 can include feature maps from one of the previous residual layers 116. Another of the inputs of the RCU 130 can include feature maps from the same residual layer 116 as the RCU 130. Conversely, one of the outputs of the RCU 130 can include feature maps fed forward along the same residual layer 116 as the RCU 130. Another of the outputs of the RCU 130 can include feature maps to be fed to one of the previous residual layer 116. The previous residual layer 116 for the output may be the same as the previous residual layer 116 for the input of the RCU 130. Within the same RCU block 128, the inputs of the RCUs 130 may be from different residual layers 116 and the outputs of the RCUs 130 may be to different residual layers 116. For example, the first RCU 130A of the RCU block 128 in the third residual layer 116C may have an input from the second residual layer 116B and an output to the second residual layer 116B. In the same RCU block 128, the second RCU 130B may have an input from the first residual layer 116A (without any directly from the second residual layer 116B) and an output to the first residua layer 116A (without and directly to the second residual layer 116B).

Each RCU 130 may include at least one down-sampler 132, at least one input aggregation operator 134, a set of transform layers 136A-N (hereinafter generally referred to as transform layers 136), at least one dimension reduction unit 138 (also referred herein as a projection unit), and at least one up-sampler 140. In some embodiments, the RCU 130 can lack the down-sampler 132, the input aggregation operator 134, or the dimension reduction unit 138, or any combination thereof.

The down-sampler 132 can receive input from one of the previous residual layers 116. The input can include, as discussed above, feature maps processed by one of the previous residual layers 116 in the segmentation model 112. The down-sampler 132 can reduce the image resolution of the feature maps received from the previous residual layer 112 to an image resolution to fit the set of transform layers 136. In some implementations, the down-sampler 132 can apply a pooling operation to reduce the image resolution of the received feature maps. The pooling operation can include, for example, max-pooling to select the highest value within each set patch in the feature map or mean-pooling to determine an average value within the set patch in the feature map. In some embodiments, the down-sampler 132 can apply a down sampling operation to the feature maps. To down-sample, the down-sampler 132 may apply a filter (e.g., a low-band frequency filter) to the feature map and select values at preset coordinates in the processed feature map.

The input aggregation operator 134 can receive input from the same residual layer 116 as the RCU 130 and the feature maps processed by the down-sampler 132. The input from the same residual layer 116 can include, for example, feature maps. The feature maps of the same residual layer 116 can be of the image resolution already fitting the set of transform layers 136 in the RCU 130. With receipt of both inputs, the input aggregation operator 134 can combine the feature maps from the down-sampler 134 and feature maps from the same residual layer 116 to generate feature maps to input into the set of transform layers 136. The combination of the feature maps may include concatenation, weighted summation, and addition, among others.

The set of transform layers 136 in the RCU 130 may process the feature maps received from the input aggregation operator 134 or directly from the same residual layer 116 as the RCU 130. Each transform layer 136 can include one or more parameters (e.g., weights) to modify or otherwise process the input set of feature maps to produce or generate an output set of features. The set of transform layers 136 can be arranged in series, with an output of one transform layer 136 fed as an input to a succeeding transform layer 136. Each transform layer 136 may have a non-linear input-to-output characteristic. In some embodiments, the set of transform layers 136 may be a convolutional neural network (CNN), including a convolutional layer, a normalization layer, and an activation layer (e.g., a rectified linear unit (ReLU)), among others. The set of feature maps processed by the transform layer 136 can be provided to the dimension reduction unit 138 and to the same residual layer 116 as the RCU 130 for additional processing by the residual layer 116.

The dimension reduction unit (DRU) 138 may receive the set of feature maps processed by the set of transform layers 136. The set of feature maps processed by the transform layers 136 may have a size or dimension incompatible for processing by the previous residual layer 116. For example, the set of feature maps may have a depth beyond the compatible number for the previous residual layer 1116. Upon receipt, the DRU 138 may apply a dimension reduction operator to the set of feature maps from the set of transform layers 136. The dimension reduction operator may include a 1×1 convolution unit, a 3×3 convolution unit, linear dimension reduction, and non-linear dimension reduction, among others. Application of the dimension reduction operator by the DRU 138 may reduce the size or the reduction of the feature maps. Upon application, the output of the DRU 138 may be fed into the up-sampler 140.

The up-sampler 140 may increase the image resolution of the feature maps received from the set of transform layers 136 to an image resolution to fit the previous residual layer 116. The previous residual layer 116 may be the same residual layer 116 from which the input to the down-sampler 132 is taken form. In some implementations, the up-sampler 140 can apply an up-sampling operation to increase the image resolution of the received feature maps. The up-sampling operation may include, for example, expansion and an interpolation filter, among others. In performing the up-sampling operation, the up-sampler 140 may insert null (or default) values into the feature map to expand the image resolution of each feature map to an image resolution compatible for processing by the previous residual layer 116. The insertion or null values may separate the pre-existing values. The up-sampler 140 may apply a filter (e.g., a low-pass frequency filter or another smoothing operation) to the expanded feature map. With the application, the feature maps processed by the up-sampler 140 may have the image resolution same as one of the previous residual layer 116 that is to receive the output from the RCU 130. The feature maps processed by the up-sampler 140 may be fed into the previous residual layer 116 for additional processing.

Figure 1M:
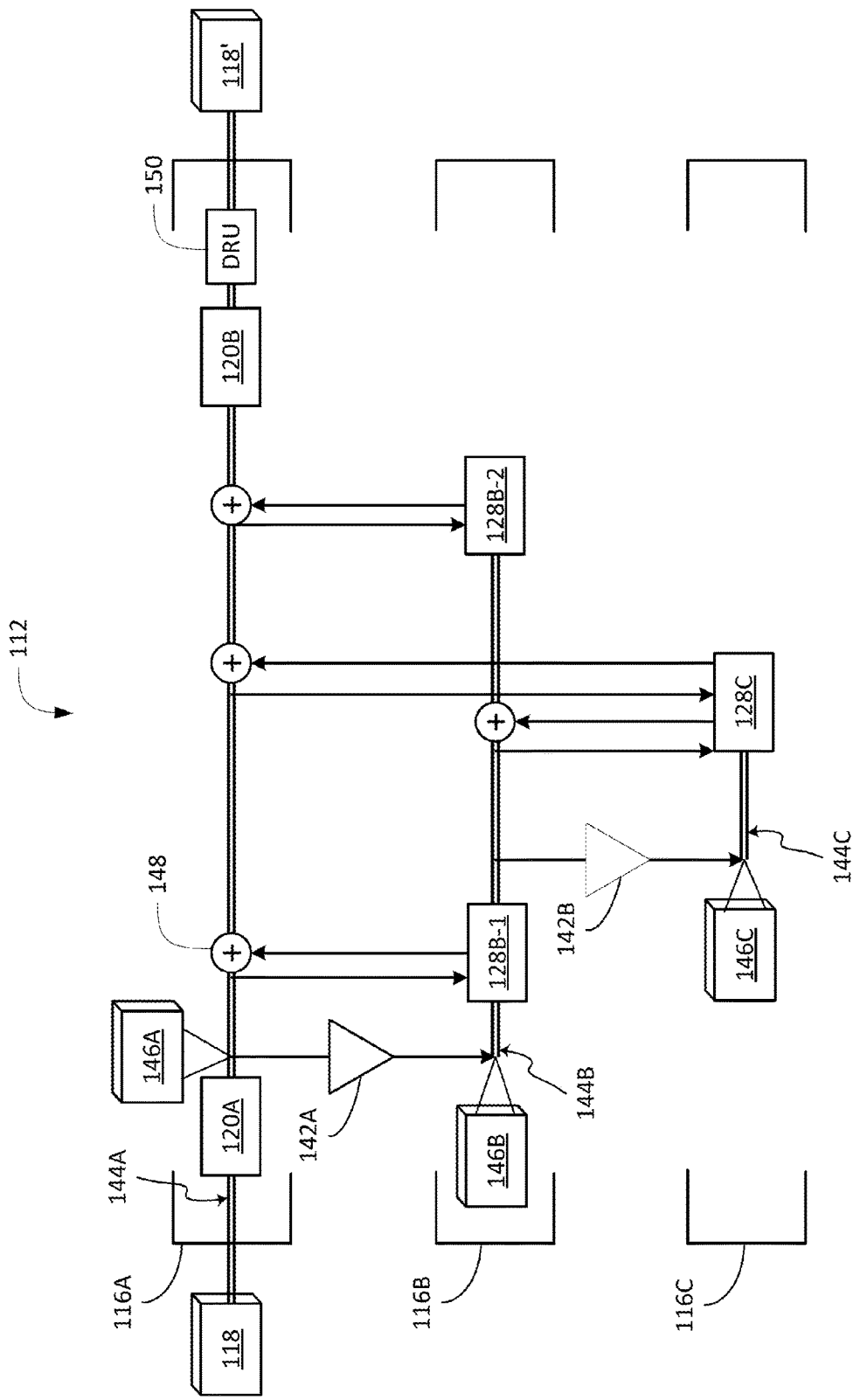
FIG. 1M is a block diagram of an example architecture for the segmentation model of the system for segmenting biomedical images.

FIG. 1M depicts a block diagram of an incremental multi-resolution residual network (MRRN) architecture of the segmentation model 112 of the system 100. The example of the segmentation model 112 has three residual layers 116A-C depicted, but the segmentation model 112 may have many more residual layers 116. The various components, such as the residual layers 116, the RU blocks, the RCU blocks 130, among others, may be connected with one another in the manner defined by the incremental MRRN architecture for the segmentation model 112 (e.g., as depicted in FIG. 1M and others).

The segmentation model 112 may have one or more pooling units 142A-N (hereinafter generally referred to as pooling units 142) spanning between or among the residual layers 116 to connect the residual layers 116. Each pooling unit 142 may retrieve, receive, or otherwise identify feature maps from one residual layer 116 to reduce in image resolution for processing by a succeeding residual layer 116. The pooling unit 142 may apply a pooling operation to the feature maps identified from the residual layer 116. The pooling operation can include, for example, max-pooling to select the highest value within each set patch in the feature map or mean-pooling to determine an average value within the set patch in the feature map. The feature maps processed by the pooling unit 142 may be of an image resolution less than the image resolution of the original feature maps identified from the residual layer 116. The pooling unit 142 may reduce the image resolution of the feature maps to the same as the down-sampler 132 in each RCU 130 of the same residual layer 116. For example, the image resolution of the feature maps outputted by the pooling unit 142 onto the second residual layer 116B may be the same of the down-sampler 132 in an RCU 130 also in the second residual layer 116B.

Each residual layer 116 of the segmentation model 112 may include at least one residual stream 144A-N (hereinafter generally referred to as the residual stream 144). Using the residual stream 144, the corresponding residual layer 116 may maintain and process a set of feature maps 146A-N (hereinafter generally referred to as the feature maps 146). The residual stream 144 of the residual layer 116 may carry the feature maps 146 from one component (e.g., RU block 120 or RCU block 130 and others) of the residual layer 116 to the next component (e.g., subsequent RC block 120 or RCU block 130) of the residual layer 116. From the processing by the pooling unit 142 spanning between residual layers 116 and the down-sampler 132 in each RCU 130, the image resolution of the feature maps 146 may decrease with successive residual layers 116. For example, the image resolution of the feature maps 146A in the first residual stream 144A of the first residual layer 116A may be four times larger than the feature maps 146A in the second residual stream 144B of the second residual layer 116B.

Each residual layer 116 of the segmentation model 121 may also include one or more aggregation units 148 along or within the residual stream 144. The aggregator unit 148 may receive input (e.g., the set of feature maps 148) from the residual stream 144 of the same residual layer 116 and the set of feature maps 148 from another residual layer 116. Upon receipt of both inputs, the aggregator unit 148 may combine feature maps 146 in the residual stream of the same residual layer 116 and the feature maps 146 from the other residual layer 116. The combination by the aggregator unit 148 may generate feature maps 146 for further processing along the residual stream 144. The combination of the feature maps 146 by the aggregation unit 148 may include concatenation, weighted summation, and addition, among others.

Each residual layer 116 of the segmentation model 112 may have one or more RU blocks 120 or one or more RCU blocks 128, among others. Among the residual layers 116 of the segmentation model 112, the types of components (e.g., RU block 120 or RCU blocks 130) and a number of components (e.g., number of RU blocks 120, RCU blocks 128, number of RUs 122 in the RU blocks 120, and the number of RCUs 130 in the RCU blocks 130). In some embodiments, the first residual layer 116A may have a set of RU blocks 120. For example, as depicted, the first residual layer 116A may have a first RU block 120A and a second RU block 120B as depicted. Each RU block 120A may have three RUs 122. In some embodiments, the second residual layer 116B and onward (e.g., residual layers 116C-N) may have a set of RCU blocks 128. The number of RCU blocks 128 may depend on the residual layer 116, and the number of RCU blocks 128 in one residual layer 116 may be one less than the number of RCU blocks 128 in the previous residual layer 116. For example, if the number of RCU blocks 128 in the second residual layer 116B is two, the number of RCU blocks 128 in the third residual layer 116C may be one. The number of RCUs 130 in each RCU block 128 may depend on which residual layers 116 the RCU block 128 is in within the segmentation model 112.

At least one of the residual layers 116 (e.g., the first residual layer 116 as depicted) of the segmentation model 112 may have at least one dimension reduction unit (DRU) 150 for the output of the residual layer 116. The DRU 150 may receive the set of feature maps 150 processed by the set of components (e.g., RU block 120 or RCU block 128) in the residual stream 144 of the residual layer 116. Upon receipt, the DRU 150 may apply a dimension reduction operator to the set of feature maps from the last component of the residual layer 116. The dimension reduction operator may include a 1×1 convolution unit, a 3×3 convolution unit, linear dimension reduction, and non-linear dimension reduction, among others. Application of the dimension reduction operator by the DRU 150 may reduce the size or the reduction of the feature maps. In some embodiments, the output for the DRU 150 may be used to generate the segmented image 118'.

The RU blocks 120, the RCU blocks 128, and the residual streams 144 of different residual layers 116 may be arranged or connected to one another across the different residual layers 116. In the incremental MRRN architecture for the segmentation model 112, the RCU blocks 128 of one residual layer 116 may receive, take, or otherwise have inputs from one or more of the previous residual layers 116. The RCU blocks 128 of the succeeding residual layers 116 may have feature maps from all previous residual layers 116 as inputs. For example, as depicted, the RCU blocks 128 of the second residual layer 116B may take the set of feature maps 146A as inputs from the first residual stream 144A of the first residual layer 116A. Furthermore, the RCU blocks 128 of the third residual layer 116C may take the set of feature maps 146A from the first residual stream 144A and the set of feature maps 146B from the second residual stream 144B.

Conversely, in the incremental MRRN architecture, the RCU blocks 128 of one residual layer 116 may produce, provide, or feed output to one or more of the previous residual layers 116. The RCU blocks 128 of the succeeding residual layers 116 may feed the output set of feature maps to all previous residual layers 116. For example, as depicted, the RCU blocks 128 of the second residual layer 116B may feed the set of feature maps as outputs to the first residual stream 144A of the first residual layer 116A. In addition, the RCU blocks 128 of the third residual layer 116C may feed the output set of feature maps to the first residual stream 144A and the output set of feature maps to the second residual stream 144B.

In the incremental MRRN architecture for the segmentation model 112, each pooling unit 142 may be arranged in an interspersed configuration between the residual layers 116. Each pooling unit 142 may be arranged after at least one component (e.g., RU block 120 or RCU block 128) in every residual layer 116 in the segmentation model 112. Each pooling unit 142 may connect an output of at least one component (e.g., RU block 120 or RCU block 128) of one residual layer 116 to feed to an input to at least one component (e.g., RCU block 128) of another residual layer 116. For example, as depicted, the output of the first RCU block 128B-1 of the second residual layer 116B may be fed via the pooling unit 142B to the RCU block 128C of the third residual layer 116C. In this manner, the feature maps 146 from one residual layer 116 may be processed at least once.

Figure 1N:
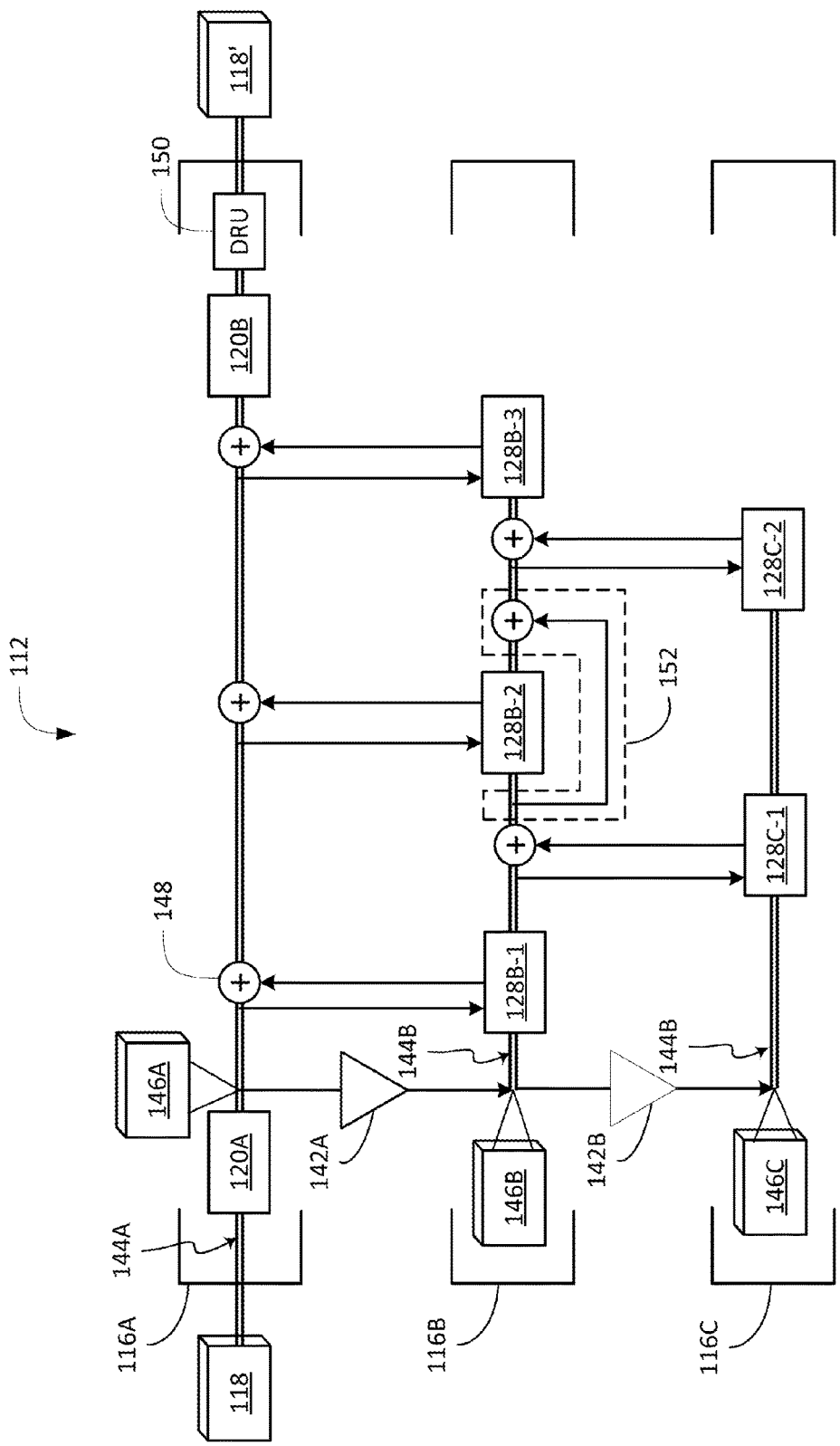
FIG. 1N is a block diagram of an example architecture for the segmentation of the system for segmenting biomedical images.

FIG. 1N depicts a block diagram of a dense multi-resolution residual network (MRRN) architecture of the segmentation model 112 of the system 100. The example of the segmentation model 112 has three residual layers 116A-C depicted, but the segmentation model 112 may have many more. The segmentation model 112 of the dense MRRN architecture may include the same or similar components as the segmentation model 112 of the incremental MRRN architecture as discussed in conjunction with FIG. 1M. For example, the first residual layer 116A of the segmentation model 112 with the dense MRRN architecture may have the same components as the first residual layer 116A of the segmentation model 112 with the incremental MRRN architecture.

The arrangement of the components in the dense MRRN architecture for the segmentation model 112 may differ from the arrangement of components in the incremental MRRN architecture for the segmentation model 112. Each pooling unit 142 may be arranged in a layered or a linear configuration beyond the first residual layer 116A. Under this configuration, all pooling units 142 can receive feature maps 146 from the previous residual layer 116 without any processing by any of the RCU blocks 128. In some embodiments, the first pooling unit 142A can receive feature maps 146 processed by the first RU block 120A of the first residual layer 116. Furthermore, each pooling units 142 can output processed feature maps 146 to the next residual layer 146 to provide as input to the first component in the residual layer 146. For example, as depicted, the first pooling unit 142A may be arranged to connect the output feature maps 146A of the first RU block 120A with the input of the first RCU block 120B-1 in the second residual layer 116B. Furthermore, the second pooling unit 142B may be arranged to connect the output feature map 146B processed by the first pooling unit 142A with the input of the first RCU block 128C-1 of the third residual layer 116C.

Moreover, the components in the dense MRRN architecture for the segmentation model 112 may differ in the layout of connections among the components in comparison to the layout in the incremental MRRN architecture for the segmentation model 112. Beyond the first residual layer 116A, the RCU blocks 128 of successive residual layers 116 may receive, take, or otherwise have inputs from the residual stream 144 of one of the previous residual layer 116. The RCU blocks 128 of the succeeding residual layers 116 may have feature maps from one of the previous residual layers 116 as inputs. For example, as depicted, the RCU blocks 128C-1 and 128C-2 of the third residual layer 116C may take the set of feature maps 148B from the second residual stream 144B of the second residual layer 116B. The RCU blocks 128 of successive residual layers 116 may lack inputs from the residual stream 144 of other previous residual layers 116. In the example depicted, the RCU blocks 128C-1 and 128C-2 of the third residual layer 116C may lack any direct input connections from the first residual stream 144A of the first residual layer 116A.

Conversely, in the dense MRRN architecture for the segmentation model 112, the RCU blocks 128 of one residual layer 116 may produce, provide, or feed output to one e of the previous residual layers 116. The RCU blocks 128 of the succeeding residual layers 116 may feed the output set of feature maps to one of previous residual layers 116. For example, as depicted, the RCU blocks 128C-1 and 128C-2 of the third residual layer 116C may feed the set of feature maps 146C as outputs to the second residual stream 144B of the second residual layer 116B. The RCU blocks 128 of successive residual layers 116 may lack outputs to feed to the residual stream 144 of other previous residual layers 116. In the example depicted, the RCU blocks 128C-1 and 128C-2 of the third residual layer 116C may lack any direct output connections to the first residual stream 144A of the first residual layer 116A.

In addition to the differences in arrangement and layout of connections, the segmentation model 112 of the dense MRRN architecture may also include a skip aggregator operator 152. At least one of the residual layers 116 may include at least one skip aggregator operator 152 along the residual stream 144. The skip aggregator 152 may be arranged in between at least a pair of RCU blocks 128 and may be arranged parallel to an interceding RCU block 128. The skip aggregator 152 may receive the set of feature maps 146 from the previous RCU block 128 (e.g., the first RCU block 128B-1) as inputs and the set of feature maps 146 from the interceding RCU block 128 (e.g., the second RCU block 128B-2) as inputs. The skip aggregator operator 126 can combine the input set of feature maps from the RCU blocks 128 (e.g., the RCU blocks 128B-1 and 128B-2) to generate an output set of feature maps for the succeeding RCU block 128 in the residual stream 144 (e.g., the RCU block 128B-3). The combination may include addition, concatenation, or a weighted summation, among others.

Referring to FIGS. 1H-N generally, with the identification of the original image 118, the model applier 108 may apply the segmentation model 112 to the original image 118 to produce or generate the segmented image 118'. The segmentation model 112 used to apply to the original image 118 may include the integral MRRN architecture or the dense MRRN architecture. The model applier 108 may feed or provide the original image 118 as input into the segmentation model 112. In some embodiments, the model applier 108 may feed the original image 118 as input into one or more of the residual layers 116 (e.g., the first residual layer 116A) of the segmentation model 112. In applying the original map 118, the model applier 108 may simultaneously or concurrently perform the functionalities of each residual layer 116 in the segmentation map 112 along with the individual components therein.

By applying the segmentation model 112, the model applier 108 may acquire or retrieve the segmented image 118' from outputs of the segmentation model 112. Compared to the original image 118, the segmented image 118' may be modified to more clearly indicate objects (e.g., tumorous growth). In some embodiments, the model applier 108 may use the output of the first residual layer 116A (e.g., feature maps 146 from the DRU 150) to generate the segmented image 118'. In some embodiments, upon generation of the segmented image 118', the model applier 108 may present or display the segmented image 118' on the display device 106.

In some embodiments, the model applier 108 may generate the segmented image 118' from outputs from multiple residual layers 116 of the segmentation models 112. In using the feature maps 146 from multiple residual layers 116, the model applier 108 may combine the feature maps 146 as a set of ensemble segmentations. In some embodiments, the model applier 108 may generate a confidence score for each value in the feature map 146 from the multiple residual layers 116. Based on the confidence scores for the values in the feature maps 146, the model applier 108 may use the value to combine to form the segmented image 118'. When the confidence score is greater than or equal to a threshold, the model applier 108 may select to include into the generation of the segmented image 118'. When the confidence score is less than the threshold, the model applier 108 may discard the value from the generation of the segmented image 118'.

In some embodiments, the model applier 108 may use the generated segmented image 118' to determine a health metric of the subject from which the original image 118 was acquired. The health metric may include those detailed herein in conjunction with Section C. The health metric may be used to predict response or early development of resistance to immunotherapy. The determination of the health metric may be based on objects recognized from the segmented image 118'. The object may be identified using computer vision techniques, such as feature detection, among others.

The model trainer 110 may train the segmented model 112 using the training dataset 114. The model trainer 110 may identify the segmented image 118'A generated using the segmentation model 118'A from the sample image 118B. The model trainer 110 may also identify the sample segmented image 118'B for the sample image 118B. With the identification of the images, the model trainer 110 may compare the generated segmented image 118'A with the sample segmented image 118'B. Based on the comparison, the model trainer 110 may calculate or otherwise determine at least one loss metric between the generated segmented image 118'A and the sample segmented image 118'B. The loss metric may indicate at least one difference between the two images 118'A and 118'B. The loss metric may be calculated using any of the formulae detailed herein. In some embodiments, the model trainer 110 may determine whether the segmentation model 112 has converted by comparing a difference between loss metrics from multiple iterations to a threshold margin. When the difference is greater than the threshold margin, the model trainer 110 may terminate training of the segmentation model 112. On the other hand, when the difference is less than the threshold margin, the model trainer 110 may continue to train.

Based on the loss metric, the model trainer 110 may modify one or more parameters of the segmentation model 112. In some embodiments, the model trainer 110 may modify individual components (e.g., RUs 122 in RU blocks 120 and RCUs 130 in RCU blocks 128) in the segmented model 112. The modification of individual components may be in accordance with deep supervision techniques (e.g., described herein in conjunction with FIG. 1E). The loss metric used to modify one or parameters may be specific to a sample feature map expected at each component within the segmentation model 112. In some embodiments, the training dataset 114 may include tomographic biomedical images of different modalities (e.g., CT and MRI). Using loss metrics calculated for each component using the images from different modalities, the model trainer 110 may modify the individual components of the segmentation model 112.

FIG. 1O depicts a flow diagram of a method 160 of segmenting biomedical images using multi-resolution residual neural networks (MRRNs). The functionalities of the method 160 may be implemented or performed using the architecture described in this section (e.g., the architectures detailed herein with FIGS. 1A-G and the system 100 as detailed in conjunction with FIGS. 1H-N) or the computing system 1500 described below in conjunction with FIG. 15A-D. A computing device may identify a biomedical image (162). The computing device may apply a segmentation model (164). The computing device may generate a segmented biomedical image (166).

FIG. 1P depicts a flow diagram of a method 170 of training models for segmenting biomedical images. The functionalities of the method 160 may be implemented or performed using the architecture described in this section (e.g., the system 100 as detailed in conjunction with FIGS. 1H-N) or the computing system 1500 described below in conjunction with FIG. 15A-D. A computing device may identify a biomedical image (172). The computing device may apply a segmentation model (174). The computing device may generate a segmented biomedical image (176). The computing device may determine a loss (178). The computing device may update the segmentation model (178). The functionalities performed at (174) may be similar to (162) in method 160, except that the functionalities may be with respect to the sampled biomedical image.

Figure 2A:
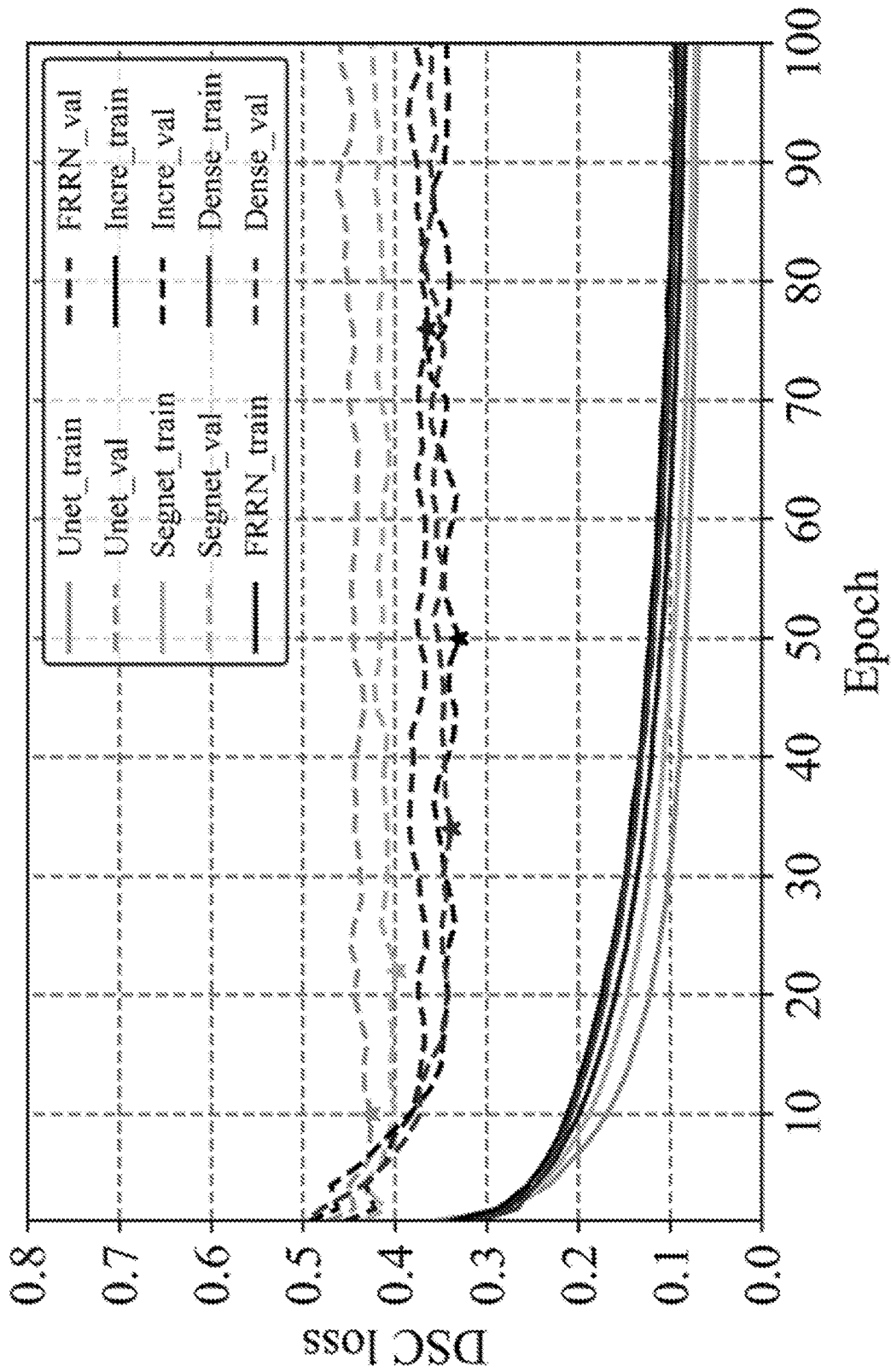
FIG. 2A is a graph showing changes in training and validation errors for the analyzed networks with training time.

FIG. 2A shows the changes in the error for the training (TCIA) and the validation (MSKCC) data using the various networks. As shown, both incremental and dense MRRN lead to the largest decrease in the DSC loss for the validation dataset. On the other hand, the Unet and the SegNet are among the methods achieving the largest validation error despite achieving the lowest training error earliest compared to the other networks. These results indicate that the same two methods potentially over fit compared to the proposed MRRN methods. The star (as seen in FIG. 2A) corresponds to the lowest validation error achieved during training. The models with lowest validation error of different methods were retained for testing on new datasets.

Figure 2B:
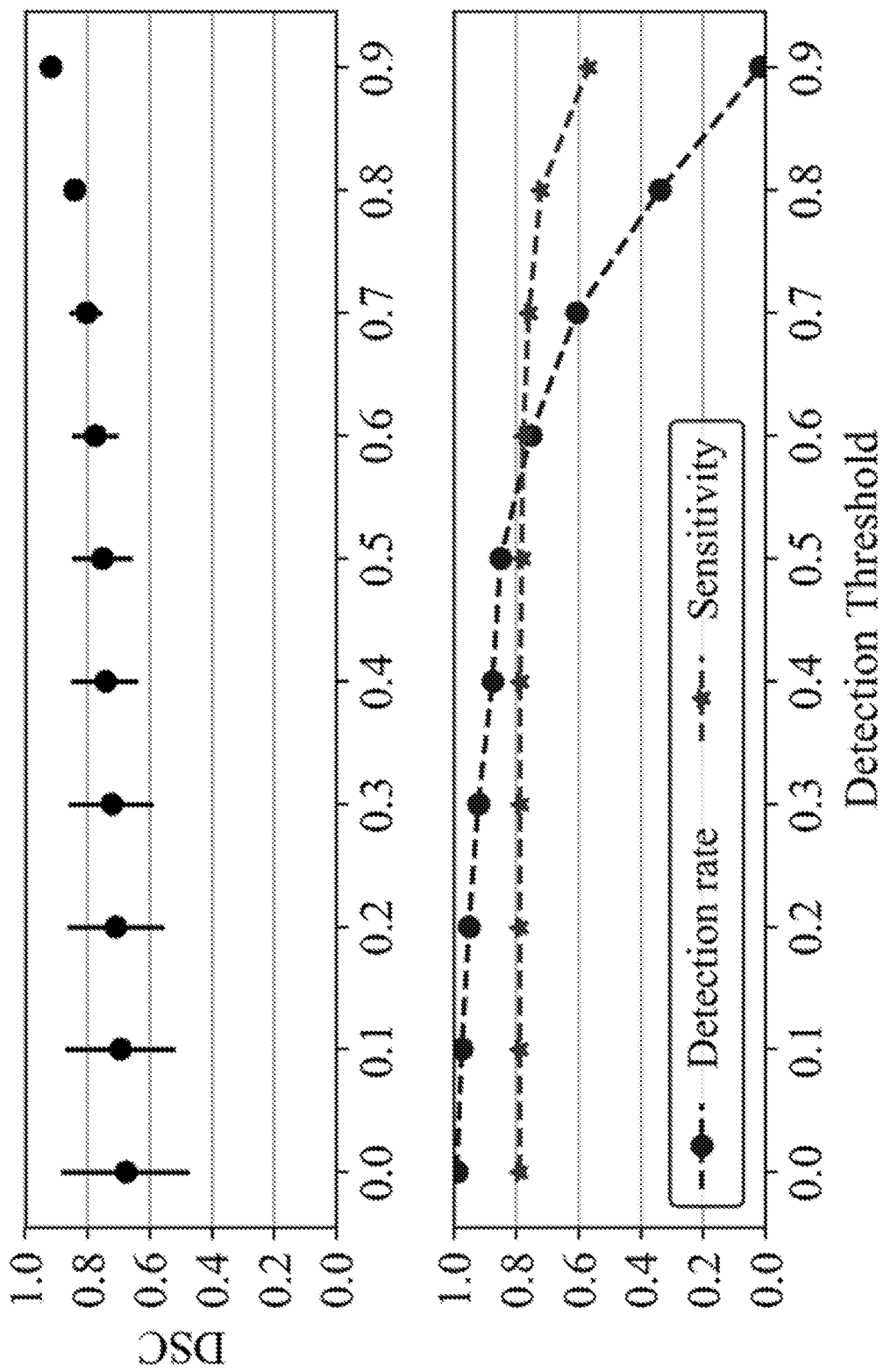
FIG. 2B are graphs showing tumor detection rates with varying detection thresholds for FRRN.

FIG. 2B shows the detection rate and sensitivity computed by varying the segmentation overlap thresholds ranging from T=0.1 to 0.9 with increment of 0.1 when using the FRRN method to benchmark performance. The average DSC increases, and the standard deviation decreases as the threshold for tumors to be considered detected increases. Correspondingly the number of detected tumors or the detection rate decreases. The detection threshold does not influence the false positive rate but only the detected number of tumors or the true positive rate. The threshold of 0.5 was chosen. Table III shows the detection rate for the analyzed datasets and methods using a detection threshold of 0.5. As shown, incremental MRRN achieved the highest detection rate while dense MRRN outperformed the previously proposed methods.

TABLE III

DETECTION RATE UNDER OVERLAP THRESHOLD OF 0.5
IN THREE DIFFERENT DATASETS
(TCIA, MSKCC AND LIDC))

|  | TCIA | MSKCC | LIDC |
| --- | --- | --- | --- |
| Unet | 0.80 | 0.78 | 0.61 |
| SegNet | 0.83 | 0.80 | 0.67 |

TABLE III-continued

DETECTION RATE UNDER OVERLAP THRESHOLD OF 0.5
IN THREE DIFFERENT DATASETS
(TCIA, MSKCC AND LIDC))

|  | TCIA | MSKCC | LIDC |
|---|---|---|---|
| FRRN | 0.84 | 0.86 | 0.64 |
| Incre MRRN | 0.89 | 0.91 | 0.72 |
| Dense MRRN | 0.88 | 0.93 | 0.71 |

Segmentation accuracies were calculated from tumors that were detected by at least one of the methods to assess clinical usability of the various methods. This resulted in 354, 299 and 455 tumors detected for TCIA, MSKCC and LIDC for segmentation analysis.

Figure 3A:
FIG. 3A is a screenshot showing example segmentation results of different methods from the three datasets withe blue contours corresponding to expert delineation and red to the algorithm generated segmentation.

FIG. 3A shows segmentation performance using the various methods for the TCIA, the MSKCC and the LIDC datasets for tumors attached to mediastinum in FIG. 3A (i,iii), to the chestwall in FIG. 3A (ii, iv, v) and for tumors enclosed within lung parenchyma in FIG. 3A (vi). The blue contour corresponds to expert delineation, while red contour corresponds to the algorithm segmentation results. The non-CNN based RF+CRF method yielded the least accurate segmentation in all three datasets across all analyzed performance metrics (see FIG. 3A, Table IV). As shown in FIG. 3A, Unet and SegNet produced worse segmentations including under and over-segmentation compared to the proposed methods. FRRN improved over both Unet and SegNet but still produced over-segmentation as shown in the case in FIG. 3A (ii, iii). On the other hand, both incremental MRRN and Dense MRRN produced close to expert segmentation in the presented cases.

Figure 3B:
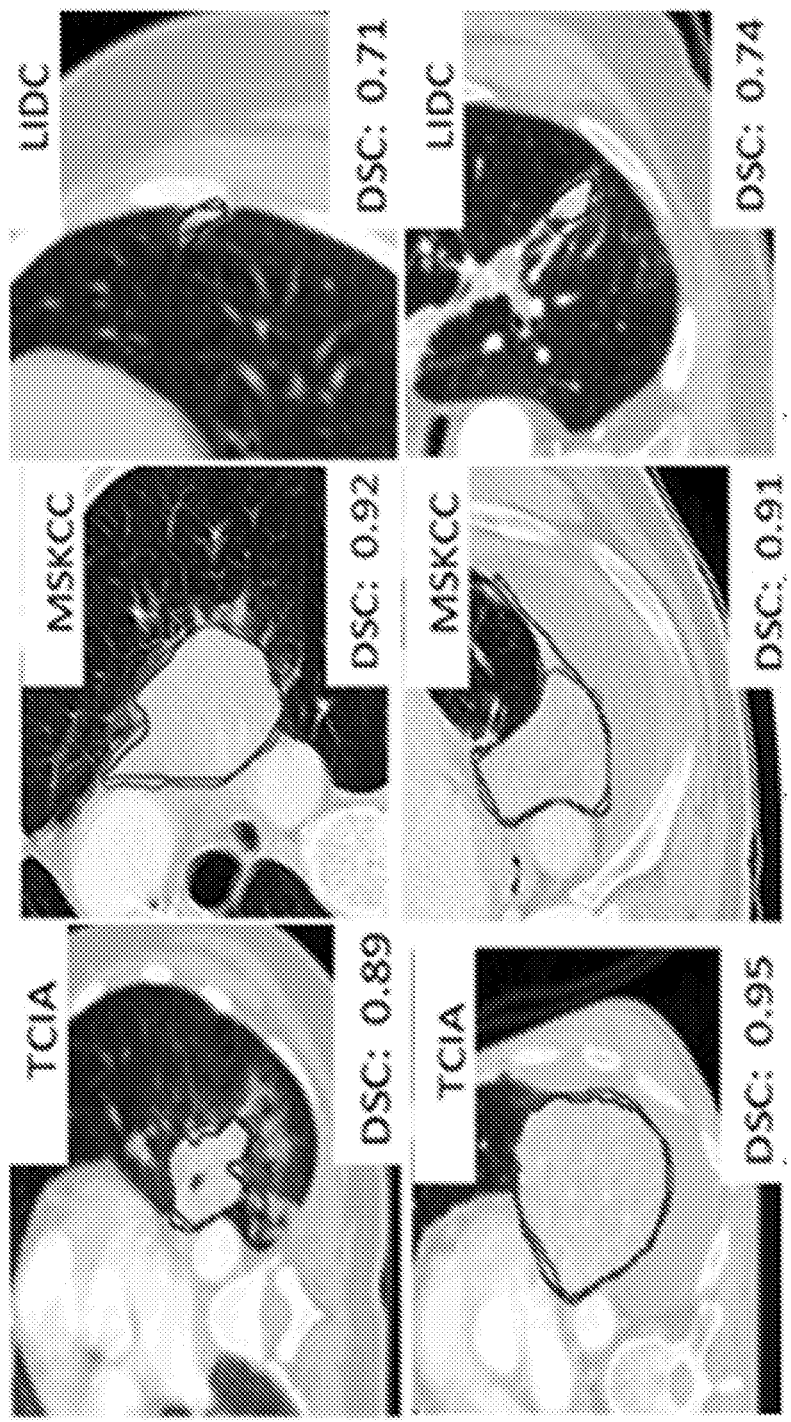
FIG. 3B is a screenshot showing example segmentation results for tumor segmentation and synthesis of MRI from CT images.
Figure 3C:
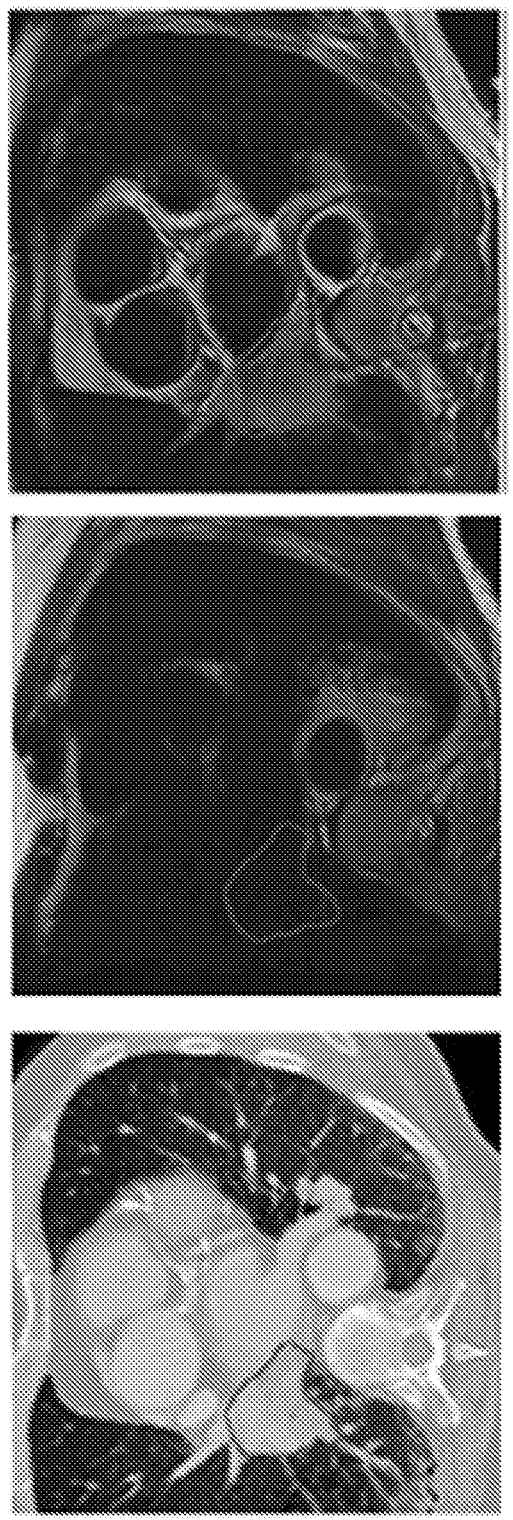
FIG. 3C is a screenshot showing example segmentation results for synthesis of MRI from CT images.
Figure 3D:
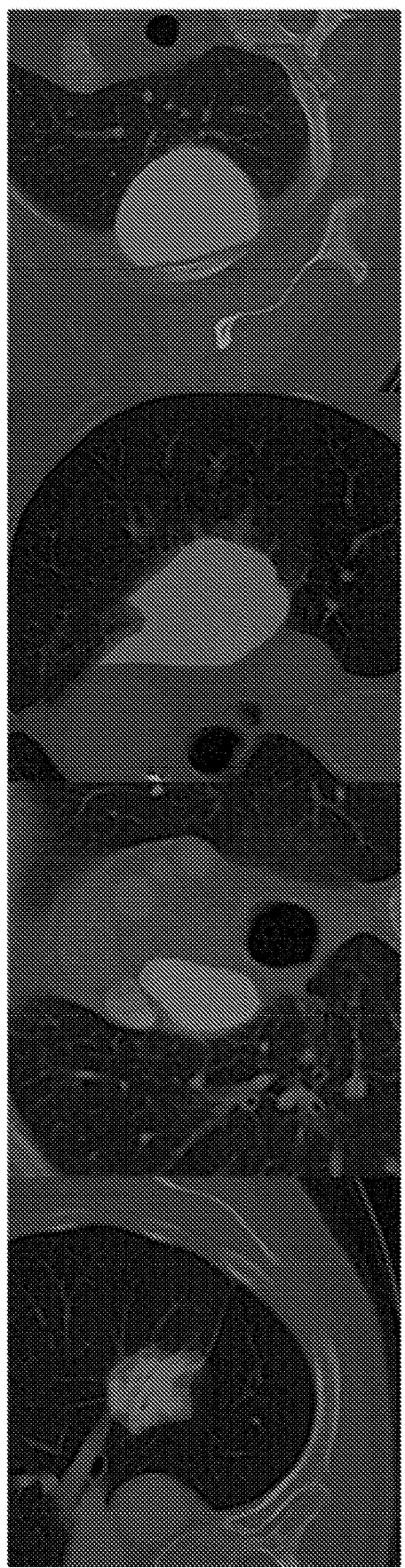
FIG. 3D is a screenshot showing results of automatic volumetric segmentation of lung tumors through deep learning using MRRN.

FIG. 3B shows segmented 1210 NSCLC tumors using synthesis of MRI from CT images from three datasets irrespective of tumor size, location, and malignancy with overall Dice overlap segmentation accuracy of 0.75±0.12. FIG. 3C shows synthesis of MRI from CT images by training with highly limited number of MRI (n=6) with unrelated CT scans (n=377). FIG. 3D depicts automatic volumetric segmentation of lung tumors through deep learning using multi-resolution residual networks.

Table IV shows the overall segmentation performance of all analyzed methods and the datasets using multiple metrics. Significant test results comparing the proposed MRRN methods with other methods are also shown. Both incremental and dense MRRNs achieved significantly higher DSC than the RF+CRF and Unet for all analyzed datasets, and significantly higher DSC compared to SegNet using internal and external validation datasets. Furthermore, both incremental and dense MRRNs achieved significantly lower Hausdorff distance (HD95) compared to all the compared methods in all datasets. The sensitivity and precision metrics using either incremental or dense MRRN were slightly improved than the compared methods.

TABLE IV

SEGMENTATION ACCURACIES OF ANALYZED METHODS USING MULTIPLE METRICS, DICE SCORE COEFFICIENT (DSC), HAUSDORFF DISTANCE (95%) (HD95), SENSITIVITY AND PRECISION, PRESENTED AS MEAN AND STANDARD DEVIATION (SD). THE SIGNIFICANT DIFFERENCES BETWEEN INCREMENTAL (INCRE), DENSE MRRN VS UNET, SEGNET, AND FRRN ARE SHOWN AS NS (P ≥ 0.05), Δ(P < 0.05), □(P < 0.01) AND *(P < 0.001). THE BEST PERFORMING METHOD IS INDICATED USING BOLD FONT. LIDC DATASET IS EVALUATED USING THE READER 1 DELINEATION.

| | | DSC | | | | | |
|---|---|---|---|---|---|---|---|
| Data | Analysis | RF + fCRF | Unet | Segnet | FRRN | Incre | Dense |
| NSCLC | Mean | 0.55 | 0.68 | 0.70 | 0.71 | 0.74\*,\*,\*,Δ | 0.73\*,\*,Δ,ns |
| (cross validation) | SD | 0.13 | 0.19 | 0.20 | 0.18 | 0.13 | 0.18 |
| MSKCC | Mean | 0.5 | 0.65 | 0.66 | 0.70 | 0.75\*,\*,\*,\* | 0.74\*,\*,\*,\* |
| (internal validation) | SD | 0.15 | 0.22 | 0.22 | 0.20 | 0.12 | 0.15 |
| LIDC | Mean | 0.49 | 0.58 | 0.57 | 0.60 | 0.68\*,\*,\*,\* | 0.67\*,\*,\*,\* |
| (external validation) | SD | 0.26 | 0.30 | 0.29 | 0.27 | 0.23 | 0.23 |

| | | Sensitivity | | | | | |
|---|---|---|---|---|---|---|---|
| Data | Analysis | RF + fCRF | unet | Segnet | FRRN | Incre | Dense |
| NSCLC | Mean | 0.42 | 0.73 | 0.73 | 0.75 | 0.80\*,\*,\*,\* | 0.79\*,\*,\*,\* |
| (cross validation) | SD | 0.15 | 0.19 | 0.18 | 0.19 | 0.16 | 0.16 |
| MSKCC | Mean | 0.44 | 0.75 | 0.72 | 0.69 | 0.82\*,\*,\*,\* | 0.80\*,\*,\*,\* |
| (internal validation) | SD | 0.16 | 0.24 | 0.27 | 0.26 | 0.18 | 0.20 |
| LIDC | Mean | 0.66 | 0.80 | 0.77 | 0.76 | 0.85\*,\*,\*,\* | 0.82\*,ns,\*,ns |
| (external validation) | SD | 0.23 | 0.15 | 0.20 | 0.23 | 0.13 | 0.15 |

| | | HD95 | | | | | |
|---|---|---|---|---|---|---|---|
| Data | Analysis | RF + fCRF | unet | Segnet | FRRN | Incre | Dense |
| NSCLC | Mean | 16.30 | 15.51 | 15.24 | 12.66 | 7.94\*,\*,\*,\* | 8.10\*,\*,\*,\* |
| (cross validation) | SD | 10.29 | 11.74 | 14.03 | 12.23 | 4.96 | 5.06 |
| MSKCC | Mean | 9.24 | 7.87 | 7.92 | 7.72 | 5.85\*,\*,\*,\* | 5.94\*,\*,\*,\* |
| (internal validation) | SD | 4.53 | 7.92 | 4.60 | 6.21 | 4.40 | 3.99 |
| LIDC | Mean | 6.93 | 4.95 | 4.48 | 2.91 | 2.60\*,\*,\*,\* | 2.72\*,\*,\*,ns |
| (external validation) | SD | 3.40 | 3.10 | 2.36 | 1.75 | 1.71 | 1.87 |

TABLE IV-continued

SEGMENTATION ACCURACIES OF ANALYZED METHODS USING MULTIPLE METRICS, DICE SCORE COEFFICIENT (DSC), HAUSDORFF DISTANCE (95%) (HD95), SENSITIVITY AND PRECISION, PRESENTED AS MEAN AND STANDARD DEVIATION (SD). THE SIGNIFICANT DIFFERENCES BETWEEN INCREMENTAL (INCRE), DENSE MRRN VS UNET, SEGNET, AND FRRN ARE SHOWN AS NS (P ≥ 0.05), Δ(P < 0.05), □(P < 0.01) AND *(P < 0.001). THE BEST PERFORMING METHOD IS INDICATED USING BOLD FONT. LIDC DATASET IS EVALUATED USING THE READER 1 DELINEATION.

|  |  | Precision | | | | | |
|---|---|---|---|---|---|---|---|
| Data | Analysis | RF + fCRF | unet | Segnet | FRRN | Incre | Dense |
| NSCLC | Mean | 0.59 | 0.71 | 0.72 | 0.73 | 0.73$*,ns,\Delta,ns$ | $0.73*,ns,ns,ns$ |
| (cross validation) | SD | 0.23 | 0.21 | 0.21 | 0.19 | 0.19 | 2.20 |
| MSKCC | Mean | 0.59 | 0.66 | 0.69 | 0.71 | 0.72$ns,ns,\Delta,*$ | $0.72*,ns,\Delta,*$ |
| (internal validation) | SD | 0.27 | 0.18 | 0.18 | 0.19 | 0.14 | 0.15 |
| LIDC | Mean | 0.66 | 0.64 | 0.60 | 0.64 | $0.67^{ns,ns,*,ns}$ | 0.70$ns,*,*,\Delta$ |
| (external validation) | SD | 0.25 | 0.26 | 0.26 | 0.27 | 0.22 | 0.21 |

Tumor Size: the effect of tumor size as shown in FIG. 4A and the location of the tumor as shown on FIG. 4B on the performance were evaluated using the various methods using DSC and HD95 metrics. The MRRN methods achieved lower HD95 values independent of the tumor size in all the datasets. Both incremental and dense MRRNs outperformed Unet and SegNet independent of the tumor size using DSC and HD95 metrics. The incremental MRRN produced slightly higher DSC compared with the FRRN in the TCIA and MSKCC datasets independent of tumor size and a markedly higher DSC for very small tumors in the LIDC dataset. Nevertheless, very small tumors are challenging to segment for all methods. The highest DSC accuracy for very small tumors on average for the incremental MRRN was (TCIA: 0.70±0.06, MSKCC: 0.74±0.11, LIDC: 0.68±0.23) compared with the lowest accuracy achieved by the RF+fCRF (TCIA: 0.29±0.20, MSKCC: 0.40±0.22, LIDC: 0.35±0.27).

Tumor location: As shown in FIG. 4B, the incremental and dense MRRNs and the original FRRN outperformed RF+CRF, Unet and Segnet on all three datasets using both DSC and HD95 metrics independent of tumor location. The overall DSC accuracy achieved by the best incremental MRRN for most difficult tumors, namely, those attached to the mediastinum was (MSKCC: 0.72±0.15, TCIA: 0.72±0.17, LIDC: 0.79±0.10) when compared with the Unet (TCIA: 0.59±0.15, MSKCC: 0.43±0.20, 0.58±0.17) method.

All methods produced consistent segmentation independent of radiologists as shown in FIG. 4C. The segmentation concordance using the various performance metrics across the four radiologists as the reference was: DSC 0.76±0.12 and HD95: 1.75±1.37 mm. Example segmentations produced by incremental MRRN from 8 randomly chosen cases together with the radiologists' segmentations are shown in FIG. 5A. Two cases in (b) and (d) are missing delineation from radiologist R2.

The best segmentation method, namely, incremental MRRN was used in the analysis which resulted in highly similar volumes changes (incremental MRRN 0.13±0.12 and expert 0.09±0.08) (FIG. 5B). There was no significant difference trend in tumor volume changes between expert and algorithmic segmentations (p=0.7). The average trend difference between the incremental MRRN and the expert delineation was 0.05±0.05.

FIG. 5B(a) shows two example patients, one with acquired resistance to treatment (no longer responding to immunotherapy) shown in red and the second with durable response (showing long term benefit from treatment) in blue. Solid lines correspond to the incremental MRRN segmentations whereas the dashed lines correspond to the expert delineation. Although the algorithm and the expert segmentation are not in perfect agreement (e.g. the algorithm results in over-segmentation since the tumor is difficult to differentiate from adjacent mediastinal pleura at the later time points in the patient with acquired resistance), the trends in volumetric changes agree. The images and the segmentations are visualized for the same two patients in FIG. 5B(b) for acquired resistance and in FIG. 5B(c) for durable response for segmentations computed from baseline and the first and second on-treatment scans separated by 9 weeks each.

Using a weight sparsity threshold of T=0.01, incremental MRRN shows a consistently decreasing feature sparsity as network depth increases in FIG. 5C. FRRN on the other hand shows no such trend with all layers getting more or less similar sparsity across network depth.

Discussion

Two different multiple resolution residual deep neural network that simultaneously combine features at different resolutions for segmenting lung tumors were developed, implemented and tested. This approach was evaluated on segmenting the largest number of lung tumors from three different datasets consisting of an internal, and two external datasets from multiple institutions. The approach showed significantly better performance compared with some of the existing deep neural network formulations typically used for medical image analysis and segmentation. The performance of the CNN-based methods was benchmarked with a shallow learning-based RF+CRF method. These results confirm prior studies that showed the improved performance of deep CNN methods over shallow learning methods. These methods also achieved the best segmentation performance independent of tumor size and location. Furthermore, the best performing network, namely, the incremental-MRRN showed good concordance with expert delineation in longitudinally tracking tumor volumes in patients with advanced stage cancers and treated with immunotherapy. It is notable that tumors treated with immunotherapy undergo changes both in volume and appearance on CT images. This approach shows that detection and tracking of such tumors is feasible. This is the first study that has employed deep learning-based auto-segmentation for analyzing continuously changing tumors treated with immunotherapy.

The results confirm the previous perspective that combining features from all levels is useful for segmentation. Specifically, the method significantly outperformed traditional approaches like Unet that incrementally concatenate features of different resolution as the images and features are passed from layer to layer. Earlier works that employed multi-resolution features include hypercolumn approach, RefineNet, and FRRN. The approach improves on the FRRN method and is somewhat similar to the RefineNet method where features from multiple resolutions are merged through a smooth incremental update such as in the incremental MRRN. However, both incremental and dense MRRNs add connections that enable passing features from all resolutions. The approach does not add more computational effort as in the hypercolumn method and can be applied to generate segmentations from reasonably sized images; hypercolumn method was restricted to 50×50 images. 160×160 images were used throughout the analysis. However, even larger sized images can be used.

Although the approaches demonstrated improved performance compared to existing methods, there is still room for improvement including for difficult to detect tumors such as those attached to the mediastinum. Another limitation is that slice-wise segmentation was used instead of 3D convolutions and employed a ROI-based training framework wherein, multiple ROIs containing different extent of tumor were generated from the same image to increase the training size. Nevertheless, this is one of the first studies that have developed and tested a deep learning network on large number of lung cancers using multi-institutional datasets and applied the method for longitudinal segmentation and tracking of tumors that change in size and appearance due to treatment with immunotherapy. In summary, a multiple resolution residual network-based deep convolutional neural network approach for generating automatic segmentation of lung tumors was presented.

Conclusion

In this paper, two neural networks to segment lung tumors from CT images by adding multiple residual streams of varying resolutions were proposed. The results clearly demonstrate the improvement in segmentation accuracy across multiple datasets. The approach is applicable to longitudinal tracking of tumor volumes for cancers subjected to treatment with immunotherapy, which alters both the size and appearance of tumors on CT. Given the success for lung tumors, the method is promising for other sites as well. Both proposed MRRN outperform existing methods.

B. Systems and Methods for Automated Segmentation from Small Datasets Through Structure Preserving Synthetic Magnetic Resonance Imaging (MRI) Generation from Computed Tomography (CT)

An adversarial domain adaptation based deep learning approach for automatic tumor segmentation from T2-weighted MRI is presented. The approach is composed of two steps: (i) a tumor-aware unsupervised cross-domain adaptation (CT to MRI), followed by (ii) semi-supervised tumor segmentation using Unet trained with synthesized and limited number of original MRIs. The present disclosure presents a novel target specific loss, called tumor-aware loss, for unsupervised cross-domain adaptation that helps to preserve tumors on synthesized MRIs produced from CT images. In comparison, state-of-the art adversarial networks trained without the tumor-aware loss produced MRIs with ill-preserved or missing tumors. All networks were trained using labeled CT images from 377 patients with non-small cell lung cancer obtained from the Cancer Imaging Archive and unlabeled T2w MRIs from a completely unrelated cohort of 6 patients with pre-treatment and 36 on-treatment scans. Next, 6 labeled pre-treatment MRI scans were combined with the synthesized MRIs to boost tumor segmentation accuracy through semi-supervised learning. Semi-supervised training of cycle-GAN produced a segmentation accuracy of 0.66 computed using Dice Score Coefficient (DSC). The method trained with only synthesized MRIs produced an accuracy of 0.74 while the same method trained in semi-supervised setting produced the best accuracy of 0.80 on test. The results show that tumor-aware adversarial domain adaptation helps to achieve reasonably accurate cancer segmentation from limited MRI data by leveraging large CT datasets.

Introduction

MRI-guided radiotherapy is an emerging technology for improving treatment accuracy over conventional CT-based radiotherapy due to better soft-tissue contrast in MR compared to CT images. Real-time and accurate tumor segmentation on MRI can help to deliver high dose to tumors while reducing normal tissue dose. However, as MRI-guided radiotherapy is not used in standard-of-care, only very few MRIs are available for training. Therefore, an adversarial domain adaptation is performed from large CT datasets for tumor segmentation on MRI.

Although deep neural networks excel in learning from large amounts of (labeled) data, their accuracy is reduced when applied to novel datasets or domains. Differences between source and target domain distribution is called domain shift. Typically used fine-tuning methods require prohibitively large labeled data in the target domain. As an alternative, domain adaptation methods attempt to minimize domain shift either by feature sharing or by learning to reconstruct the target from source domain. In essence, domain adaptation methods learn the marginal distributions to transform source to target domain.

The problems of domain shift are exacerbated in medical images, where imaging modalities capture physical properties of the underlying anatomy differently (e.g., CT vs. MRI). For example, whereas bones appear hyper-dense on CT and dark on MRI, tumors appear with similar contrast as normal soft-tissue on CT but have a distinct appearance on MRI (as depicted in (a) and (b) of FIG. 6A). Consequently, learning the marginal distributions of the domains alone may not be sufficient. Cross-domain adaptation of highly different modalities has been applied in medical image analysis for image synthesis using paired images and unpaired images, as well as for segmentation. However, all aforementioned approaches aim to only synthesize images that match the marginal but not the structure-specific conditional distribution such as tumors. Matching the overall distribution using the standard generational adversarial network methods, leads to a problem called mode collapse or mode-limited synthesis wherein, the synthesized images do not capture the multi-modal intensity statistics of the target imaging modality. Therefore, segmentation and classification using such synthetic images will lead to lower accuracy.

Therefore, a novel target specific loss, called tumor-aware loss, is introduced for unsupervised cross-domain adaptation that helps to preserve tumors on synthesized MRIs produced from CT images (as seen in (d) of FIG. 6A), which cannot be captured with just the cycle-loss (as seen in (c) of FIG. 6A).

Method

Our objective is to solve the problem of learning to segment tumors from MR images through domain adaptation from CT to MRI, where there is access to a reasonably sized labeled data in the source domain ($X_{CT}$, $y_{CT}$) but are provided with very limited number of target samples $X_{MRI} \ll X_{CT}$ and fewer labels $y_{MR}$. This solution first employs tumor-aware unsupervised cross-domain adaptation to synthesize a reasonably large number of MRI from CT through adversarial training. Second, the synthesized MRI is combined with a fraction of real MRI with corresponding labels and train a Unet for generating tumor segmentation as outlined in FIG. 6B. $X_{CT}$ and $X_{MRI}$ are the real CT and MRI; $X_{CT}^{MRI}$ and $X_{MRI}^{CT}$ are the synthesized MR and CT images; $y_{CT}$ is the CT image label; $G_{CT} \rightarrow$MRI and $G_{MRI} \rightarrow$CT are the CT and MRI transfer networks; $\tilde{X}_{MRI}$ and $\tilde{y}_{MRI}$ are a small sample set from the real MRI, used to train semi-supervised segmentation.

The first step is to learn a mapping $G_{CT} \rightarrow$MRI that synthesizes MRI from the CT images to fool a discriminator $D_{MRI}$ using adversarial training. Additionally, an adversarial loss $L_{adv}^{CT}$ is calculated for synthesizing CT from MRI by simultaneously training a network that learns a mapping $G_{MRI} \rightarrow$CT. The adversarial loss, $L_{adv}^{MRI}$, for synthesizing MRI from CT, and $L_{adv}^{CT}$, for synthesizing CT from MRI, are computed as:

$$L_a^{dvMRI}(G_{CT} \rightarrow MRI, D_{MRI}, X_{MRI}, X_{CT}) = \mathbb{E}_{x_m \sim X_{MRI}}[\log (D_{MRI}(x_m))] + \mathbb{E}_{x_c \sim X_{CT}}[\log(1 - (D_{MRI}(G_{CT} \rightarrow MRI(x_c)))] L_{adv}^{CT}(G_{MRI} \rightarrow CT, D_{CT}, X_{CT}, X_{MRI}) = \mathbb{E}_{x_c \sim X_{CT}} [\log(D_{CT}(x_c))] + \mathbb{E}_{x_m \sim X_{MRI}}[\log(1 - (D_{CT}(G_{MRI} \rightarrow CT(x_m))]$$ (1)

where $x_c$ and $x_m$ are real images sampled from the CT ($X_{CT}$) and MRI ($X_{MRI}$) domains, respectively. The total adversarial loss is then computed as the summation of the two losses as $L_{adv} = L_{adv}^{MRI} + L_{adv}^{CT}$. A cycle consistency loss is computed to regularize the images synthesized through independent training of the two networks. By letting the synthesized images be $x_m' = G_{CT} \rightarrow MRI(x_c)$ and $x_c' = G_{MRI} \rightarrow CT(x_m)$, the cycle consistency loss $L_{cyc}$ is calculated as:

$$L_{cyc}(G_{CT} \rightarrow MRI, G_{MRI} \rightarrow CT, X_{CT}, X_{MRI}) = \mathbb{E}_{x_c \sim X_{CT}}[\| G_{MRI} \rightarrow CT((x_m')) - x_c\|_1] + \mathbb{E}_{x_m \sim X_{MRI}}[\| G_{CT} \rightarrow MRI(x_c') - x_m \|_1].$$ (2)

The cycle consistency and adversarial loss only constrain the model to learn a global mapping that matches the marginal distribution but not the conditional distribution pertaining to individual structures such as the tumors. Therefore, a model trained using these losses does not need to preserve tumors, which can lead to either deterioration or total loss of tumors in the synthesized MRIs (as seen on (c) of FIG. 6A). Therefore, a tumor-aware loss is introduced that forces the network to preserve the tumors. To be specific, the tumor-aware loss is composed of a tumor loss and a feature loss. The tumor loss is computed by training two parallel tumor detection networks using simplified models of the Unet for CT ($U_{CT}$) and the synthesized MRI ($U_{MRI}$). The tumor loss constrains the CT and synthetic MRI-based Unets to produce similar tumor segmentations, thereby, preserving the tumors and is computed as:

$$L_{tumor} = \mathbb{E}_{x_c \sim X_{CT}, y_c \sim y_{CT}}[\log P(y_c | G_{CT} \rightarrow MRI(x_c))] + \mathbb{E}_{x_c \sim X_{CT}, y_c \sim y_{CT}}[\log P(y_c | X_{CT})].$$ (3)

On the other hand, the tumor feature loss $L_{feat}$ forces the high-level features of $X_{CT}$ and $X_{CT}^{MRI}$ to be shared by using a constraint as:

$$L_{feat}(x_c \sim X_{CT}) = \frac{1}{C \times H \times W} \| \phi_{CT}(x_c) - \phi_{MRI}(G_{CT} \rightarrow MRI(x_c)) \|^2.$$ (4)

where $\phi_{CT}$ and $\phi_{MRI}$ are the high-level features extracted from the $U_{CT}$ and $U_{MRI}$, respectively; C, H and W indicate the size of the feature. The total loss is then expressed as:

$$L_{total} = L_{adv} + \Delta_{cyc} L_{cyc} + \Delta_{tumor} L_{tumor} + \Delta_{feat} L_{feat}.$$ (5)

where $\lambda_{cyc}$, $\lambda_{tumor}$ and $\lambda_{feat}$ are the weighting coefficients for each loss. During training, the domain transfer or generator network G, the discriminator D, and the tumor constraint network U are alternatively updated with the following gradients, $-\Delta_{\theta_G}(L_{adv} + \lambda_{cyc} L_{cyc} + \Delta_{tumor} L_{tumor} + \lambda_{feat} L_{feat})$, $-\Delta_{\theta_D}(L_{adv})$ and $-\Delta_{\theta_U}(L_{tumor} + \lambda_{feat} L_{feat})$.

The synthesized MRI from the first step were combined with a small set of real MRIs with labels ($\tilde{X}_{MRI}$ and $\tilde{y}_{MRI}$ in FIG. 6B) to train a U-net using Dice similarity coefficient (DSC) loss to generate tumor segmentation. Adversarial network optimization for MRI synthesis was frozen prior to semi-supervised tumor segmentation training to prevent leakage of MRI label information.

Figure 6C:
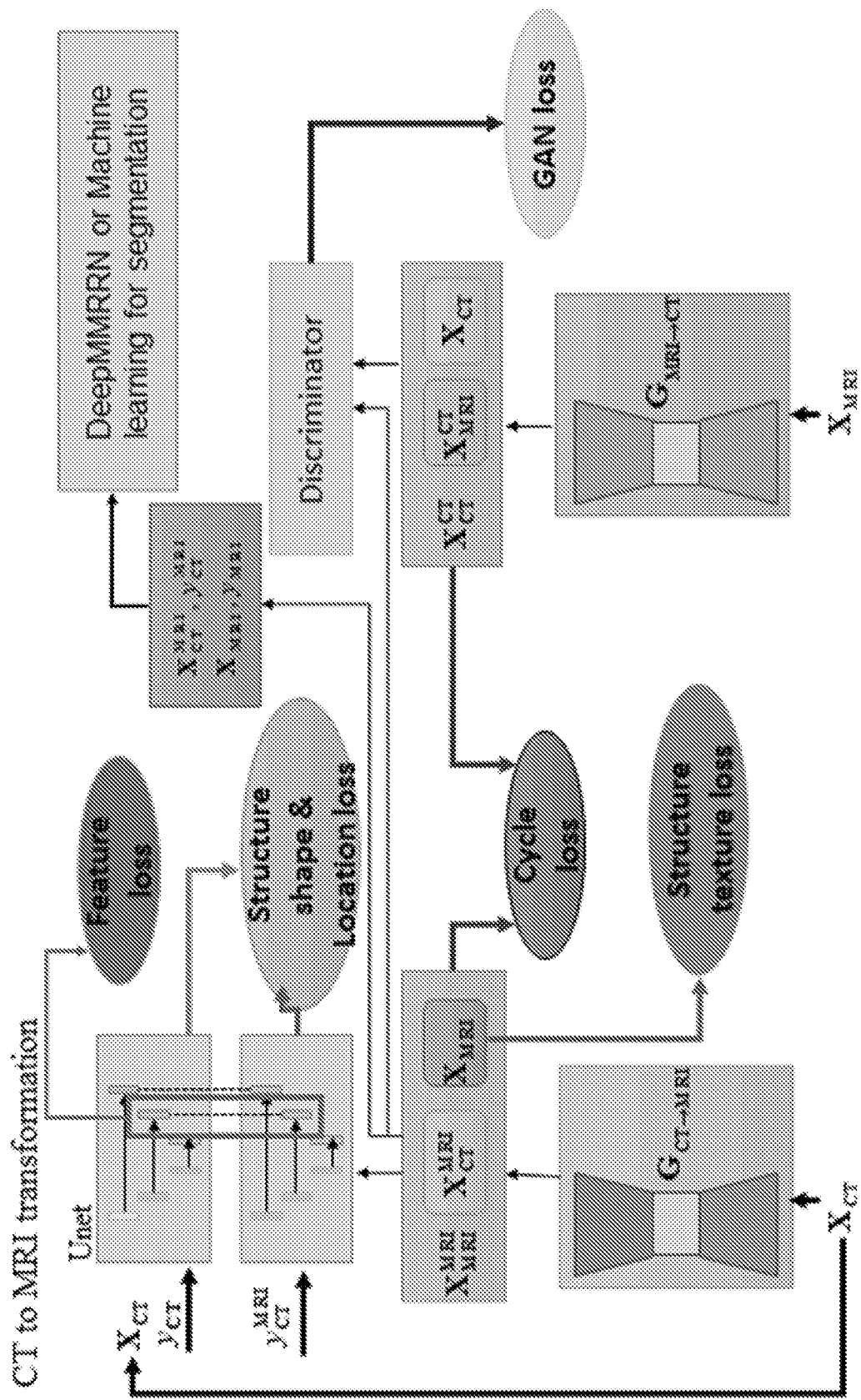
Figure 6D:
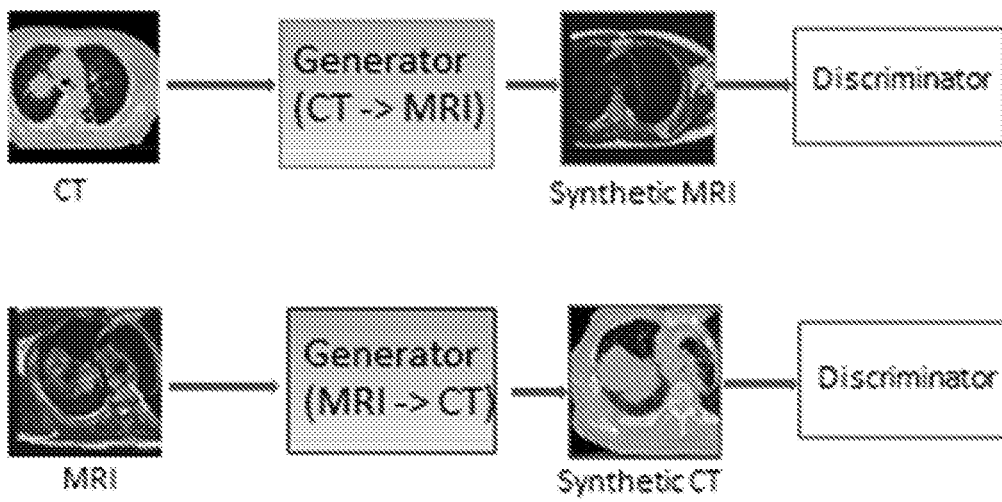
Figure 6E:
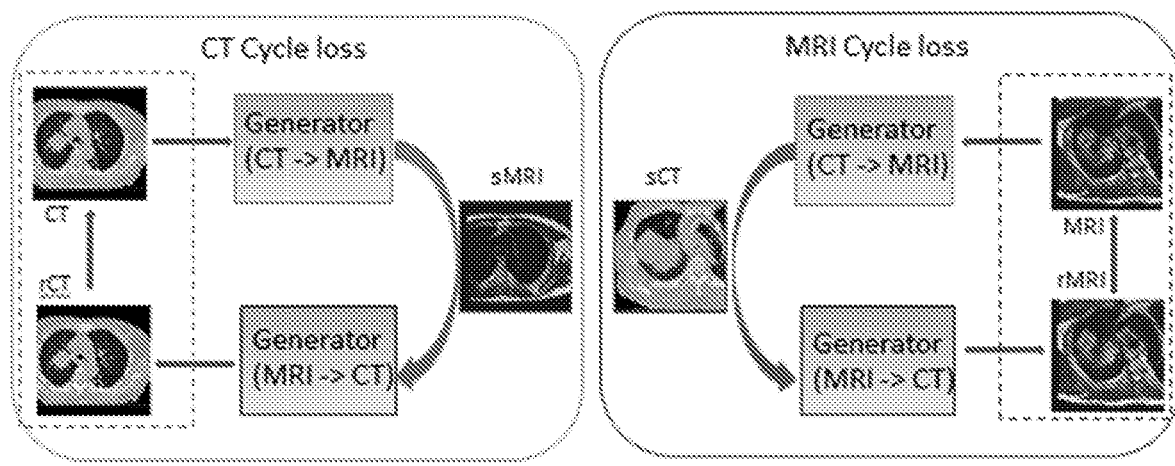
Figure 6F:
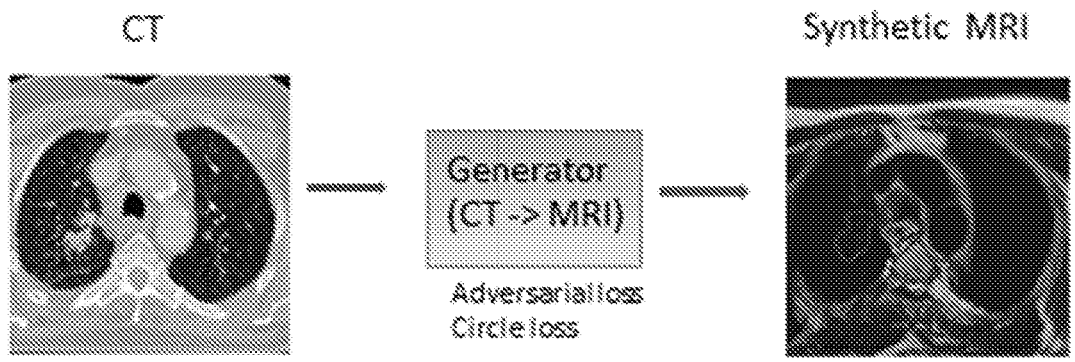
Figure 6G:
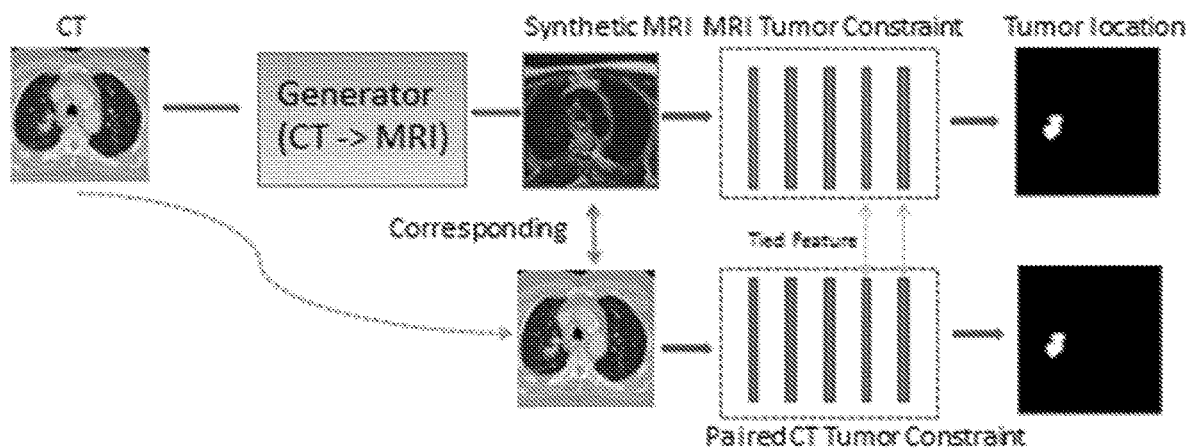
Figure 6H:
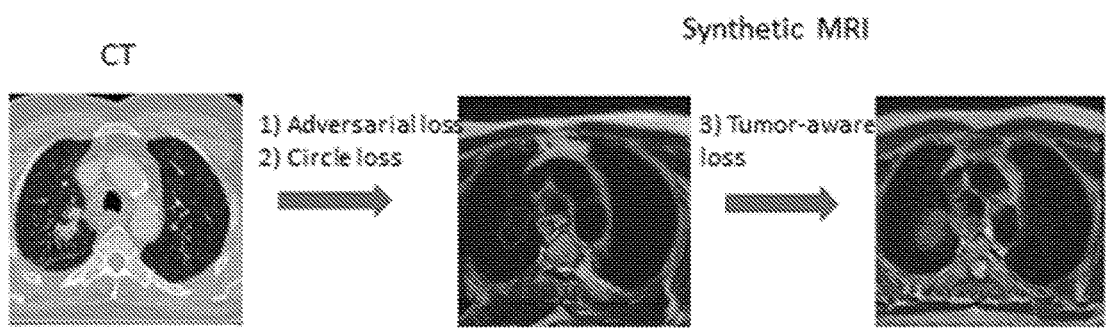
Figure 61:
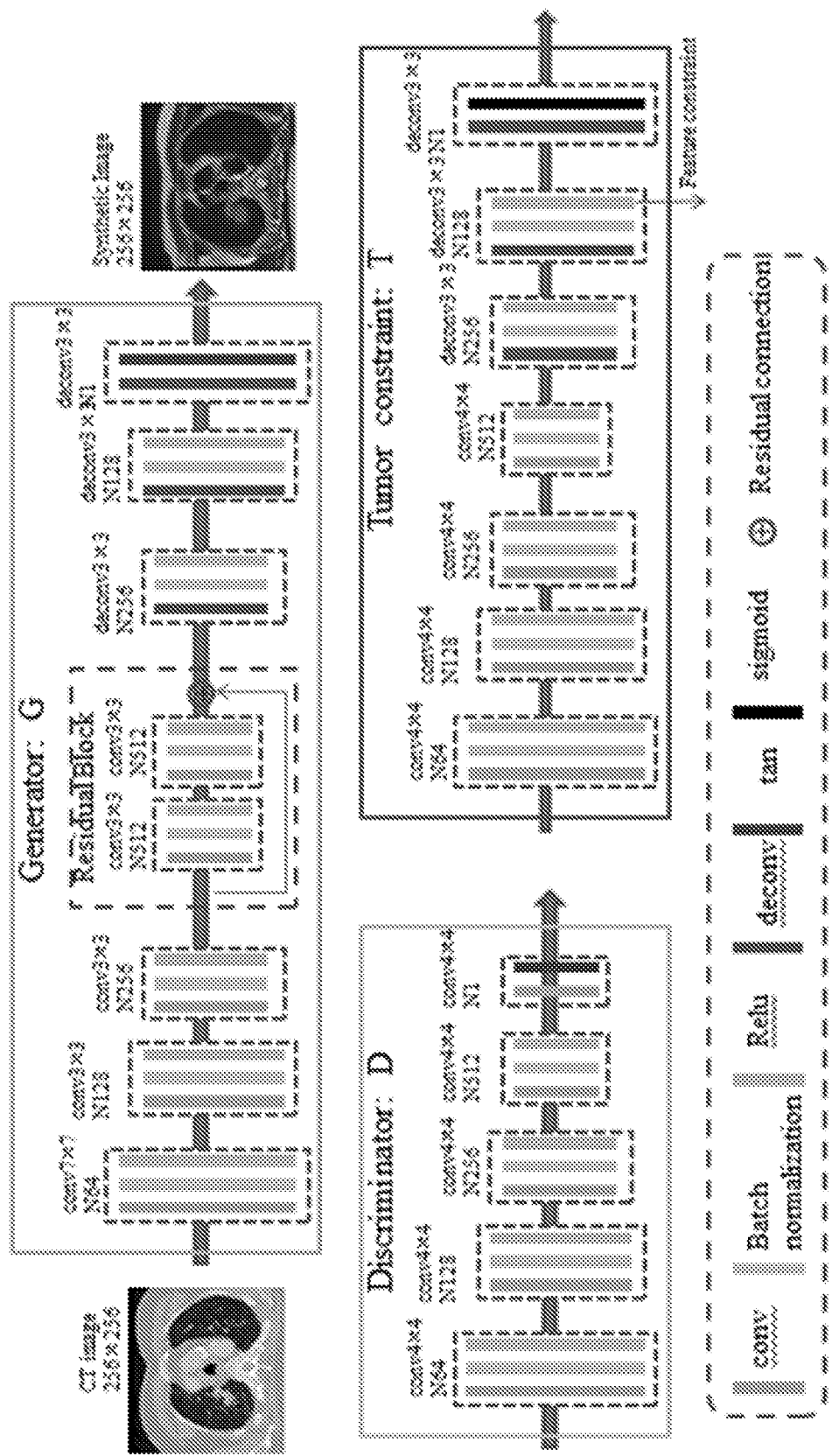

FIG. 6C shows an architecture for machine learning automated segmentation from small datasets through structure preserving synthetic MRI generation from CT. The MRI and CT image synthesis from different modalities are learned jointly through a dual generative adversarial network. This approach includes a number of different losses, notably, the GAN loss (or the adversarial loss), the cycle consistency loss (or the cycle loss), the feature loss, the structure texture loss, and the structure shape and location loss. T2w MRI was tested but the same technique is applicable to contrast MRI such as T1pre or T1pos—contrast MRI and other anatomic MRI sequences. GAN loss: This loss enforces the networks to produce as realistic synthetic images as possible by minimizing the difference between synthetic and real MRI or synthetic and real CT. Note that synthetic MRI are produced from CT and synthetic CT are produced from the MR images. Cycle loss: This loss enforces the two generator networks to produce realistic synthetic images but relaxes the constraint that the images from the two modalities arise from the same patient or have their anatomy aligned.

Briefly, the synthesized CT (or MRI) from one network is used as input to the second generator to produce synthetic MRI (or CT) which is compared to the original MRI (or original CT). This forces the two networks to be able to reproduce the original input images. Feature loss introduced forces the real CT and synthetic MRI (synthesized from the real CT) to produce the same feature activations for a specific structure (say tumor or any normal structure). This means that the features responsible for producing segmentation match between the synthesized and real target modality (e.g. MRI), that in turn enforces the structure preservation constraint. The last two decoding layers of an additional deep network (such as Unet) shown in the figure are tied between the additional networks processing real CT and synthetic MRI to force those networks to capture the structure's high-level features. Tying or matching features from other layers enables to enforce different types of constraint on the activation. Structure shape and location loss introduced forces the additional networks to produce identical segmentation of a structure using real CT and synthesized MRI (produced from real CT) by comparing the overlap between the structure to preserve the structure's shape and location in the image. Structure texture loss introduced forces the networks to preserve the textural appearance in the real and synthesized MRI. Computed together with the cycle consistency loss, this loss tries to minimize the discrepancy in the textural features such as in the case of tumors with necrotic components to preserve the same appearance.

As shown in FIGS. 6D-6I, the system first part of the system involves two GAN, one transfer CT to MRI while the other transfer MRI to CT. For example, the generator transfer from CT to MRI, the input is a CT image and the output is a transferred MRI image. The generator MRI to CT is same. At this stage, the two generator is independent. The cycle loss will connect them together. The third loss is the tumor-aware loss. Using generative loss and the circle loss will make the tumor disappear. Since tumor has the same intensity with heart or other healthy tissue in CT. When it turns those intensity into black in the transferred MRI, the tumor disappears. Thus, a constraint is applied on the CT to MRI generator. A tumor-aware loss is proposed to include a tumor loss and a feature loss. The tumor loss helps to preserve the tumor location once a CT tumor label is given in the CT images. As shown, a tumor in the location is generated where has a tumor in the CT. The second part of the loss is feature loss, the same discriminative feature distribution is kept among the MRI tumor constraint network and its corresponding CT network.

Experiments and Results

Ablation Tests

The impact of adding tumor-aware loss to the cycle loss (proposed vs. cycle-GAN versus masked-cycle-GAN) was tested. Images synthesized using aforementioned networks were trained to segment using semi-supervised learning by combining with a limited number of real MRI. Adversarial synthesis combines tumor labels as an additional channel with the original images as masked-cycle-GAN. The effect of adding a limited number of original MRI to the synthesized MRI on segmentation accuracy (tumor-aware with semi-supervised versus tumor-aware with unsupervised training) was evaluated. The lowest achievable segmentation accuracy was benchmarked by training a network with only the pre-treatment (or week one) MRI.

Datasets

The image synthesis networks were trained using contrast-enhanced CT images with expert delineated tumors from 377 patients with non-small cell lung cancer (NSCLC) available from The Cancer Imaging Archive (TCIA), and an unrelated cohort of 6 patients scanned with T2w MRI at the clinic before and during treatment every week (n=7) with radiation therapy. Masked cycle-GANs used both tumor labels and the images as additional channels even for image synthesis training. Image regions enclosing the tumors were extracted and rescaled to 256×256 to produce 32000 CT image slices and 9696 T2w MR image slices. Only 1536 MR images from pre-treatment MRI were used for semi-supervised segmentation training of all networks. Segmentation validation was performed on the subsequent on-treatment MRIs (n=36) from the same 6 patients. Test was performed using 28 MRIs consisting of longitudinal scans (7,7,6) from 3 patients and pre-treatment scans from 8 patients not used in training. Tumor segmentation accuracy was evaluated by comparing to expert delineations using the Dice Score Coefficient (DSC), and the Hausdorff Distance 95% (HD95).

MRI Synthesis Results

FIG. 7A shows the representative qualitative results of synthesized MRI produced using only the cycle-GAN ((b) of FIG. 7A), masked cycle-GAN ((c) of FIG. 7A) and using this method ((d) of FIG. 7A). As seen, this method best preserves the anatomical details between CT and MRI. Quantitative evaluation using the Kullback-Leibler (KL) divergence computed from tumor regions between synthesized and original MRI, used for training, confirmed that this method resulted in the best match of tumor distribution with the lowest KL divergence of 0.069 compared with those obtained using the cycle-GAN (1.69) and masked cycle-GAN (0.32).

Segmentation Results

FIGS. 7B and 7C each show the segmentations generated using the various methods (yellow contours) for three representative cases from the test and validation sets, together with the expert delineations (red contours). As shown in Table 1, this approach outperformed cycle GAN irrespective of training without (unsupervised) or with (semi-supervised) labeled target data. Semi-supervised segmentation outperformed all methods in both test and validation datasets.

TABLE 1

| | Segmentation accuracy | | | |
|---|---|---|---|---|
| | Validation | | Test | |
| Method | DSC | HD95 mm | DSC | HD95 mm |
| Week one only | 0.63 ± 0.27 | 7.22 ± 7.19 | 0.55 ± 0.25 | 13.23 ± 0.75 |
| cycle-GAN | 0.57 ± 0.24 | 11.41 ± 5.57 | 0.66 ± 0.16 | 11.91 ± 4.44 |
| masked cycle-GAN | 0.67 ± 0.21 | 7.78 ± 4.40 | 0.63 ± 0.24 | 11.65 ± 6.53 |
| Tumor aware unsupervised | 0.62 ± 0.26 | 7.47 ± 4.66 | 0.74 ± 0.15 | 8.88 ± 4.83 |
| Tumor aware semi-supervised | 0.70 ± 0.19 | 5.88 ± 2.88 | 0.80 ± 0.08 | 7.16 ± 4.52 |

Discussion

In this work, a novel target-specific loss is introduced, namely tumor-aware loss for synthesizing MR images from unpaired CT datasets using unsupervised cross-domain adaptation. The tumor-aware loss forces the network to retain tumors that are typically lost when using only the cycle-loss and leads to accurate tumor segmentation. Although applied to lung tumors, this method is applicable to other structures and organs. Segmentation accuracy of this approach trained with only synthesized MRIs exceeded other methods trained in a semi-supervised manner. Adding small set of labeled target domain data further boosts accuracy. The validation set produced lower but not significantly different (p=0.1) DSC accuracy than the test set due to significantly smaller (p=0.0004) tumor volumes in validation (mean 37.66 cc) when compared with the test set (mean 68.2 cc). These results showed that masked-cycle-GAN produced lower test performance compared to basic cycle-GAN, possibly due to poor modeling from highly unbalanced CT and MR datasets. As a limitation, this approach only forces the synthesized MRIs to preserve tumors but not the MR intensity distribution within tumors. Such modeling would require learning the mapping for individual scan manufacturers, magnet strengths and coil placements which was outside the scope of this work. Additionally, synthesized images irrespective of the chosen method do not produce a one-to-one pixel mapping from CT to MRI. There is also room for improving the segmentation accuracy by exploring more advanced segmentation models, e.g. boundary-aware fully convolutional networks (FCN).

Conclusion

In this disclosure, a tumor-aware, adversarial domain adaptation method using unpaired CT and MR images was introduced for generating segmentations from MRI. This approach preserved tumors on synthesized MRI and generated the best segmentation performance compared with state-of-the-art adversarial cross-domain adaptation. The results suggest feasibility for lung tumor segmentation from MRI trained using MRI synthesized from CT.

C. Systems and Methods for Deep Learning-Based Segmentation Enables Predicting Treatment Outcomes and Longitudinal Treatment Monitoring Despite the adoption of checkpoint blockade immunotherapy in a variety of cancers, only a minority of patients benefit from the therapy. The entropy radiomics feature extracted from baseline and early on-treatment computed tomography images were identified to be early predictor of immunotherapy response and development of acquired resistance. Fifty-nine patients were analyzed. Elastic net regression classifiers were trained using the texture measures extracted from baseline and on-treatment scans from 48 patients to predict durable clinical benefit (DCB). The feature most relevant to predict DCB was used to predict acquired resistance in a subset of 22 patients (11 not used for predicting DCB) with long-term benefit from immunotherapy lasting >1 year. Entropy, that emphasizes image heterogeneity, was identified as most relevant feature to predict DCB. High entropy at the first on-treatment scan was significantly associated with DCB (P=0.020) and with overall survival after adjusting for lines of therapy, age, gender, smoking status, and tumor site (hazard ratio 0.99, 95% CI 0.98-1.00, P=0.016). Elastic net regression incorporating textures achieved the highest and comparable nested leave one-out cross-validation accuracy (AUROC 0.82 [95% CI 0.68-0.92]) as a full model that integrated textures with PD-L1 expression and volume. Low baseline entropy (P=0.020) and increase in entropy early in therapy (P=0.030) was associated with later development of acquired resistance. These results indicate that entropy is likely associated with immunotherapy response, but analyses of larger cohorts will be required to optimize radiomics signatures to predict and monitor immunotherapy response.

Introduction

Lung cancer is the leading cause of cancer deaths worldwide. Immunotherapy with programmed cell death-1 (PD-1) checkpoint-blockade has demonstrated impressive survival advantage for patients with lung cancers, and many other cancers. Anti-programmed cell death-1 (PD-1) inhibitors like the pembrolizumab are now approved in the United States for treatment of patients with PD-L1 expressing NSCLC, melanoma, head and neck cancer, and mismatch repair deficient tumors among many others.

Despite the success of immunotherapy in lung cancers, only a minority patient benefit with immunotherapy. Multiple studies have shown that PD-L1 expression is associated with enriched response. Other biomarkers such as total non-synonymous mutational burden are associated with response. However, these assays have incomplete prediction, require invasive biopsies that represent only a moment in time and are affected by heterogeneity in sampling. A critical next step is identifying biomarkers that precisely predict outcome and differentiate responders from non-responders early in treatment these in order to enable application of immunotherapies with greater precision.

Radiomics is a new method of advanced image analysis of standard-of-care medical images that has been applied to multiple cancers to identify non-invasive predictors of tumor aggressiveness, to identify sub-regions with differing tumor biology, and to predict outcomes to therapy in multiple cancers. Concretely, radiomics analysis quantifies the spatial variations in the radiographic signal intensity within individual tumors through features that describe edges, tumor shape and tumor texture.

It is hypothesized that higher imaging heterogeneity within tumors captured by radiomics could be used to predict or monitor immunotherapy response. In particular, the feasibility of employing computed tomography (CT) image-based texture features was examined for predicting and monitoring response in lung cancer patients treated with anti-PD-1 monotherapy (pembrolizumab). The study is complementary to a parallel study that employed radiomics analysis from baseline CT images to predict lung cancer patients likely to develop hyper-progressive disease when treated with checkpoint-blockade immunotherapy.

To avoid overfitting with a limited dataset, the radiomics measures were limited to a set of four texture features relevant to heterogeneity. Additionally, using the most relevant texture that associated with response to pembrolizumab, it was explored whether the same texture feature distinguished those patients who eventually developed late acquired resistance to treatment compared to those with ongoing, durable benefit lasting >1 year.

Results

Clinical Characteristics

Fifty patients with NSCLC treated with pembrolizumab (Group I) were evaluated to identify texture features associated with primary outcome, namely, durable clinical benefit. 48 (96%) out of 50 had tumors in whom texture features could be examined from pre- and on-treatment scans as seen in Table 1. Two patients had no measurable tumors following treatment and were thus excluded from the study. The median follow-up of the patients was 7.67 mos (IQR 2.14-16.64). Quantitative PD-L1 expression was available for 46 of 48 (96%) patients, and as expected, associated with improved PFS and OS when considered categorically (positive versus negative) and when considered as a continuous variable as depicted in FIG. 8B. Twenty two of 48 (46%) had durable clinical benefit and 54% had no durable clinical benefit (NDB).

TABLE 1

Clinical Characteristics

| Feature | Group I | | Group II* |
|---|---|---|---|
| | DCB (n = 22) | NDB (n = 26) | DCB (n = 11) |
| Age median (range) | 62 (57-66) | 62 (54-70) | 64 (60-74) |
| Number of metastatic sites, baseline median (range) | 2 (1-4) | 3 (2-3) | 3 (2-4) |
| Total tumor volume, baseline median(range) cc | 27 (14-93) | 38 (18-63) | 58 (13-108) |

TABLE 1-continued

Clinical Characteristics

|  | Group I | | Group II* |
| --- | --- | --- | --- |
| Feature | DCB (n = 22) | NDB (n = 26) | DCB (n = 11) |
| Qualitative Tumor PD-L1 | | | |
| Positive (>/=1%) | 21 | 21 | 0 |
| Negative (<1%) | 1 | 4 | 0 |
| Unknown | 0 | 1 | 11 |
| Quantified PD-L1 expression available | 20 | 26 | 0 |
| Female sex | 14 | 15 | 4 |
| Tobacco use | | | |
| Never | 2 | 8 | 2 |
| Current | 6 | 4 | 5 |
| Former | 14 | 14 | 4 |

*All patients had long-term benefit with immunotherapy, were not treated with pembrolizumab and were only used to test feasibility to distinguish patients with durable on-going benefit from those with acquired resistance using the most relevant texture identified to be associated with response to pembrolizumab.

Baseline Radiomic Features and Outcomes

As seen in Table 1 and FIG. 8A, none of the baseline CT image-based textures significantly associated with DCB. With the exception of continuous measures of baseline entropy (FIG. 8A), none of the texture features were associated with overall or progression-free survival (Table 2). Elastic net regression model trained using only the baseline textures predicted DCB with nested leave-one-out cross validation with area under receiver operating curve (AU-ROC) of 0.53 (95% CI 0.36-0.70), which is not significantly different from a random classifier (AUROC=0.5). Inclusion of quantitative tumor-PD-L1 expression to the model increased the leave-one-out classifier accuracy to an AUROC of 0.68 (95% CI 0.52-0.82).

First On-Treatment and Delta Texture Radiomics and Outcomes

The association between DCB and radiomic textures from the first on-treatment scan, as well the association with delta textures computed between the first scan and baseline as depicted in FIG. 8A was examined. As seen on Table 1, of all the CT image-based texture features at the first scan, only higher entropy was significantly associated with DCB (DCB median 129 vs, NDB median 98, P=0.028). Higher homogeneity from first on-treatment and increasing entropy (ΔEntropy) were only significantly different between DCB vs. NDB before adjusting for multiple comparisons as seen on FIG. 8A. In addition, as expected, decreasing tumor volume (positive ΔVolume) was also significantly associated with DCB (DCB median 7.3 cc, IQR 3.3 cc to 31.4 cc, NDB median −10.6 cc, IQR −29.9 cc to 2.9 cc, P=0.002).

Texture Entropy Following First On-Treatment Scan Predicted Overall Survival

After adjusting for age, gender, lines of therapy, smoking status, and tumor site, entropy from first on-treatment scan was associated with OS (hazard ratio 0.99, 95% CI 0.98 to 1.00, P=0.016), whereas delta tumor volume was not associated with OS (hazard ratio 1.00, 95% CI 0.38 to 3.30, P=0.15) as seen in Table 2. Dichotomized using median entropy, tumors with greater than median entropy had improved OS when compared to those with entropy less than or equal to the median as seen on FIG. 8B.

TABLE 2

Classification accuracy for differentiating between patients determined to have DCB vs. NDB. Tests for significance were performed between the textures only and all other methods by comparing the ROCs of the individual methods. Elastic net regression model using CT textures alone predicted DCB with comparable accuracy as an integrated model that combined textures, PD-L1 expression and volume

| Features | TPR | TNR | FPR | FNR | AUROC 95% CI | P value |
| --- | --- | --- | --- | --- | --- | --- |
| Textures only | 0.79 | 0.68 | 0.21 | 0.32 | 0.82 (0.68-0.92) | |
| Textures, PD-L1 | 0.75 | 0.63 | 0.25 | 0.37 | 0.80 (0.65-0.92) | 0.3 |
| Textures, volume, PD-L1 | 0.83 | 0.74 | 0.17 | 0.26 | 0.82 (0.68-0.94) | 1.0 |
| Volume, PD-L1 | 0.79 | 0.55 | 0.21 | 0.45 | 0.79 (0.66-0.91) | 0.7 |
| PD-L1 | 0.76 | 0.35 | 0.24 | 0.75 | 0.57 (0.40-0.74) | 0.02 |

Given the previously established association between PD-L1 expression and immunotherapy benefit, the feasibility of a classifier trained was examined using quantitative PD-L1 expression to predict immunotherapy response. Logistic regression performed only using quantitative tumor PD-L1 expression had a modest accuracy as seen in Table 3 possibly due to the use of single predictor in the model. On the other hand, a classifier computed using textures measures from first on-treatment and delta textures that measure the changes in textures from baseline to first on-treatment, achieved the best accuracy of AUROC=0.82, 95% CI (0.68-0.92), TPR=0.79, TNR=0.68. A model that combined textures with quantitative tumor PD-L1 expression produced a slightly lower accuracy of AUROC=0.80, 95% CI (0.65-0.92), TPR=0.75, TNR=0.63. The texture measures were ranked higher than quantitative PD-L1 expression for predicting DCB as seen in FIG. 8C. In comparison, a model that used only the volume and quantitative tumor PD-L1 expression achieved a lower accuracy of AUROC=0.79, 95% CI (0.66-0.91), TPR=0.79, TNR=0.55. A combined model using PD-L1 expression, volume, and textures produced a comparable accuracy as the textures only model of AUROC=0.82, 95% CI (0.68-0.94), TPR=0.83, TNR=0.74 as seen in Table 3. There was no significant difference in the accuracies between the texture (first on-treatment and delta measures) and the combined model (P=1.0). Although larger volume after first treatment showed a significant association to positive PD-L1 expression as seen on FIG. 8C, neither entropy nor volume was associated with qualitative PD-L1 expression after adjustment for multiple comparisons. Additionally, contrast texture and volume (and decrease in volume) from first on-treatment, showed a mild positive and negative correlation, respectively, with quantitative tumor PD-L1 expression as seen on Table 3.

TABLE 3

Adjusted Cox analysis for predicting PFS and OS using continuous measures of entropy and Δ Volume. The CT texture and volume measures were adjusted for age, gender, lines of therapy, smoking status and tumor site.

| Features Continuous | Progression Free Survival | | | Overall Survival | | |
|---|---|---|---|---|---|---|
| | Hazard Ratio | 95% CI | p-Value | Hazard Ratio | 95% CI | p-Value |
| Entropy | 0.99 | 0.98-1.00 | 0.13 | 0.99 | 0.98-1.00 | 0.016* |
| ΔVolume (cc) | 3.90 | 1.45-10.5 | 0.007* | 1.46 | 0.48-4.40 | 0.50 |
| Smoking Former | 1.29 | 0.54-3.10 | 0.57 | 1.29 | 0.45-3.70 | 0.63 |
| Smoking Never | 4.76 | 1.51-15.0 | 0.008 | 2.82 | 0.70-11.3 | 0.14 |
| Line Rx | 0.94 | 0.75-1.20 | 0.59 | 0.92 | 0.71-1.20 | 0.51 |
| Age | 1.00 | 0.96-1.00 | 0.92 | 1.04 | 1.00-1.10 | 0.07 |
| Gender Male | 2.37 | 1.11-5.10 | 0.025 | 4.58 | 1.80-11.7 | 0.001 |
| Site not Lung | 0.75 | 0.32-1.8 | 0.52 | 0.99 | 0.34-2.90 | 0.98 |

Increasing Entropy Among Long-Term Responders Differentiates Acquired Resistance from Durable Ongoing Benefit with Immunotherapy Next, an exploratory analysis was examined with 22 patients by combining 11 patients from the first group of patients treated with pembrolizumab with a second group of 11 (Group 2) as seen on Table 1 patients all of whom showed long term benefit from immunotherapy, to see if serial changes in entropy might be associated with those who eventually develop acquired resistance (AR) rather than ongoing durable response (DR). Among the 22 patients, 11 eventually developed acquired resistance compared to 11 with durable response remaining progression-free. In this group of long term responders, high baseline entropy was significantly associated with DR (p=0.02) as depicted in (a) of FIG. 8D. Within this group, AR patients but not DR patients showed increasing entropy (see FIG. 8D) on each on-treatment scan (first, second and third, see FIG. 4). Furthermore, the cumulative delta entropy was significantly higher in patients with AR following the first (p=0.03), and second (p=0.02) treatment scans. The trend of decreasing entropy in patients with DR is not steady, and reverses following the third on-treatment CT scan as seen in (b) of FIG. 8D.

Discussion

Non-invasive approaches to predict response or detect early development of resistance to immunotherapy could substantially inform clinical management, avoiding futile treatments and focusing on likely responders. As immunotherapy approaches change, imaging biomarkers could play a key role in quantitative monitoring of response. Quantification of disease heterogeneity, captured with radiomics features, has been shown to be more useful for predicting treatment response compared to using size-based measures alone. In this study, the feasibility of using radiomics texture-based features extracted from CT images was examined for predicting outcomes to immunotherapy. Among the candidate measures, higher entropy computed at baseline and first on-treatment was found to be an independent predictor of benefit to pembrolizumab. Also, it was shown that texture measures alone could be used to build a predictive model that is comparable in accuracy to a combined model that integrated textures with quantitative tumor PD-L1 expression and volume. Finally, baseline entropy and changes in entropy computed from the baseline, first, and second follow-up CT scans in patients with long-term response appear to differentiate those who developed acquired resistance compared to durable, ongoing response.

It is important to note that none of the baseline textures predicted durable clinical benefit, although the high baseline and increase in entropy following first treatment did predict OS. It is possible that extracting many textures may help determine baseline predictors to immunotherapy, as hinted at by the finding that, among responders, durable response beyond one year was associated with higher baseline entropy compared to patients who eventually acquired late resistance. However, to avoid overfitting in this initial dataset, limited set of texture features were focused on.

The utility of delta textures was examined to predict outcomes, including survival, following chemoradiotherapy as suggested by previous results. Overall, higher entropy was found at baseline and immediately following the first treatment was associated with a better outcome in patients treated with PD-(L)1 monotherapy. Although patients who developed acquired resistance were also significantly associated with increasing entropy following treatment, it is important to note that these group of patients initially responded to treatment (or demonstrated DCB) and had long-term response (PFS lasting >1 year), unlike patients who did not benefit from immunotherapy (or NDB). The results are different than results of previous studies for radiochemotherapy that showed that high-pretreatment or an increase in entropy following treatment was associated with worse outcomes. Relation between radiomics measures computed from baseline CT scans and immunotherapy outcomes including survival in melanoma and lung cancers have been examined. It is perhaps particularly intriguing that increasing entropy, even very early in treatment, may be associated with late acquired resistance compared to those with ongoing, durable benefit. A larger cohort study combined with histopathological or immune markers is essential to understand the association between the overall tumor heterogeneity and the underlying tumor biology.

CT image acquisition, and area within which texture entropy computed from Laplacian of Gaussian edges are all correlated to entropy. It was recommended a minimum area of 200 pixels for entropy calculation, as well as adjustment for tumor site and acquisition protocol. All texture features were computed from volumes instead of region of interests from a single slice, hence all texture measures were extracted from a reasonable number of pixels. Although the texture parameters in the study were calculated differently, namely, using the gray level co-occurrence matrix instead of from the Laplacian-of-Gaussian edges.

No strong relationship was found between texture features and tumor PD-L1 expression. Interestingly, combining textures with volume and tumor PD-L1 expression produced similar accuracy as a model that was built exclusively using textures to detect patients with durable clinical response with pembrolizumab. This may be due to the limited size of the dataset. The modest accuracy of quantitative PD-L1 expression only classifier model may be the result of using a single feature whereas all other classifier models integrated multiple features which would lead to better accuracy.

Finally, the largest tumor for analysis was used to predict treatment response, as opposed to combining the information from all metastatic tumor sites. Although it is intriguing to study how the heterogeneity between all the metastatic tumor sites evolves during these of immunotherapy and ultimately affects response to immunotherapy, this approach was not pursued due to the fact that majority of the patients had at most two tumor sites.

The study is limited by the modest sample size of 48 patients used for identifying the relevant texture measure associated to immunotherapy outcomes. To keep the study population homogeneous, only patients treated with PD-(L)1 monotherapy was used. This data limitation had several ramifications: a large scale radiomics analysis was not used and only the preselected radiomics features were focused on. In addition, the dataset was too small to break into a training plus validation set, although this limitation was partially ameliorated by employing nested, leave one-out cross-validation for all predictive metrics. A second cohort not used in the primary analysis was included to study the difference between patients with acquired resistance and durable response. Clearly, a larger multi-institutional study is needed to build an optimal radiomics-based predictor of immunotherapy response, as well as establishing the best follow-up times to compute delta texture measures changes to monitor and predict long term treatment response, including acquired resistance. Study of the evolution of radiomics features in relation to emerging combinations of immunotherapy treatments, including immunotherapy and radiation therapy, is another area of needed investigation. Despite these limitations, this is among the first reports to the knowledge to study the association between radiomics textures and changes in those measures as a result of treatment and response to immunotherapy.

Material and Methods

Patient Characteristics

The primary analysis to examine radiomic features associated with outcomes focused on cohort of 50 patients (48 were ultimately evaluable) with advanced NSCLC treated with pembrolizumab at MSKCC as part of a previously reported Phase 1 study (KEYNOTE-001) (Group I). Per protocol, patients were treated with pembrolizumab 2 or 10 mg/kg every two or three weeks, and contrast-enhanced CT scans were performed every 9 weeks. All patients had pre-treatment and on-treatment CT scans acquired every 9 weeks. A second cohort of patients with NSCLC long-term benefit with PD-(L)1 therapy, defined as >1-year progression-free survival was used to examine whether the most relevant texture feature associated with response to pembrolizumab was also able to discriminate between patients who ultimately developed acquired resistance (AR) (progression defined by RECIST) from those with ongoing, long-term benefit or durable response (DR). This cohort (Group II) included 11 patients from Group I and an additional 11 patients treated at MSKCC with anti-PD-(L)1 monotherapy (nivolumab n=8, durvalumab n=3, atezolizumab n=1). Of note, patients in Group II who were not treated with pembrolizumab were not used in the identification of relevant radiomics texture feature for predicting the primary efficacy of immunotherapy outcome.

Clinical Outcomes

CT scans were performed at baseline and every 9 weeks thereafter and were evaluated for objective response using RECIST v1.1. For the purposes of this analysis, the primary efficacy outcome was durable clinical benefit (DCB, defined as partial or stable response lasting >6 mo; vs no durable benefit (NDB)). Overall survival (OS) and progression-free survival (PFS) were also examined. OS was defined as the time from diagnosis to the time of death or censoring and PFS was defined as the time from initial treatment with pembrolizumab to date of progression or censor.

PD-L1 Expression Testing

PD-L1 was performed and expression was scored centrally as part of the clinical trial (clone 22C3, Merck). Expression was defined as the percent of tumor cells with present membranous PD-L1 expression. PD-L1 positive was defined as >/=1% expression; PD-L1 negative was defined as <1% expression. PD-L1 expression testing was performed only on Group I patients and quantitative PD-L1 expression was available for 46 out of 50 patients.

Computed Tomography Acquisition and Segmentation

Diagnostic contrast enhanced CT images were acquired using standard clinical scanning protocols at the institution with a GE "LightSpeed" CT scanner (GE Medical System™, Milwaukee, QI, USA). The most common pixel spacing was [0.7 mm×0.7 mm×5.0 mm]. An experienced thoracic radiologist identified all measurable tumors at baseline using the GE PACS software. The identified tumors were then used to segment all tumors at baseline and all available on-treatment scans using the grow-cut method in 3DSlicer as well as deep learning segmentation using MRRN. Tumor contours were manually adjusted where necessary.

In patients with more than one target lesion, the segmented tumor with the largest volume on the baseline CT scan was automatically selected for analysis and the corresponding tumors at on-treatment scans were identified. In the cases wherein the largest tumor at baseline disappeared after the first treatment, the method selected the next largest tumor at baseline that had a follow up measurement in the subsequent on-treatment scans. Tumor volume constituted the CT-based size measurement extracted using the grow-cut segmentation algorithm.

Radiomics Features Extraction

The voxel-wise Haralick textures known as energy, entropy, contrast, and homogeneity were extracted from tumor volumes by first scaling the CT images to 0-256, followed by texture extraction using the in-house software implemented in C++ using a wrapper implementation of the Insight Toolkit (ITK) with 32 histogram bins and a 5×5×1 radius around each voxel. Textures for each tumor were computed as the mean of voxel-wise texture values within that tumor. The texture features were computed from preand on-treatment CT scans using the largest at-baseline tumors. In the case of patients whose largest tumors disappeared following treatment, the next largest at-baseline tumor was used for analysis. The employed texture features, whose formulas are given in, capture different aspects of the tumor appearance as follows:

Energy captures the uniformity in the distribution of signal intensities within the tumor. Hence, tumors with a homogeneous appearance will have high energy values.

Entropy emphasizes the heterogeneous appearance or differences in pixel intensities within tumors by characterize the variability in the distribution of signal intensities within individual tumors. Therefore, tumors with highly variable distributions of signal intensities will have in high values of entropy.

Contrast measures the variability in intensity distributions between local pixels by emphasizing large intensity differences between adjacent pixels. As an example, tumors with many edges will have higher contrast values.

Homogeneity measures the extent of similarity in intensity distributions between adjacent pixels by emphasizing local intensity similarities, and is the opposite of contrast. For example, tumors with identical intensities everywhere in the image or tumors with distinct sub-regions with uniform intensities within those regions will have a higher homogeneity.

In addition to single time-point assessment of these textures, texture changes were calculated by differencing the texture features computed from baseline and the first on-treatment scan, thereby producing delta texture features:

$$\Delta_f = \frac{(f^{t1} - f^{pre})}{(f^{pre} + f^{t})}, \quad (1)$$

$f$ = {energy, entropy, homogeneity, contrast}

Finally, for patients with ongoing benefit lasting >1-year, cumulative delta textures were calculated to examine differences in acquired resistance versus ongoing durable response:

$$\overline{\Delta}_f^T = \sum_{t=1}^{T} \frac{(f^t - f^{pre})}{(f^{pre} + f^t)} + \overline{\Delta}_f^{t-1} \begin{cases} \overline{\Delta}_f^{t-1} = 0, & \text{if } t = 1 \\ \overline{\Delta}_f^{t-1}, & \text{otherwise} \end{cases}, \quad (2)$$

$f$ = {energy, entropy, homogeneity, contrast} where T is the time point up to which the delta textural change is summed and can range from the first on-treatment CT scan measurement till the last available CT scan measure. As shown in the formula, the cumulative delta texture captures the normalized changes in the texture starting from changes in the first on-treatment scan till T scans and the cumulative delta entropy following first on-treatment is same as the delta entropy measure in Equation (1).

Statistical and Data Analysis

All statistical analysis was performed in R (v.3.3.1). Textures were computed using the ITK toolbox, version 4.2, as noted. Patient characteristics and texture features were summarized using standard descriptive statistics using median and interquartile range (IQR). Cox regression was employed to assess associations between OS and PFS and the texture measures after adjusting for tumor site, age, gender, lines of therapy, and smoking status. Hazard ratio, confidence intervals (CI) at 95% were calculated. Schoenfeld residuals were computed to test the proportionality assumptions. Kaplan-Meier curves were used to estimate OS and PFS using dichotomized values of the texture features. Median values of the individual textures were used to split the patients into two groups. Libraries used for the analysis included survminer, survcomp, pROC, ggplot, gpubr, and caret packages in R.

Predictive Modeling

Elastic net regression modeling was used to rank textures (first on-treatment or delta) and PD-L1 by importance for predicting DCB. To avoid over-fitting and reduce bias, nested leave one-out cross validation was performed to optimize the hyper-parameter, namely, the regularization parameter (k) used in the elastic net regression. Only the most relevant texture was selected, given the size of the dataset, for assessing association to outcomes including survival (PFS and OS) and to predict long-term response (acquired resistance vs. durable response). Separate models were computed using textures alone, combination of textures and quantitative PD-L1 expression, and combination of textures, volume and quantitative PD-L1 expression. A graphical overview of the approach is given in FIG. 8A.

Conclusion

Whether CT-based texture measures are feasible to predict outcomes to mono-immunotherapy in patients with NSCLC was evaluated. The results show that non-invasively measured texture features are likely to be associated with outcomes to immunotherapy and furthermore may provide an early prediction of late acquired resistance among responders. The optimization of radiomic signatures to predict and monitor immunotherapy response will require a much larger multi-institutional cohort.

D. Systems and Methods for Cross Modality Prior-Augmented Deep Learning for Robust Lung Segmentations from Small Datasets Accurate tumor segmentation is a requirement for magnetic resonance (MR)-based radiotherapy. Lack of large expert annotated MR datasets makes training deep learning models difficult. Therefore, a cross-modality (MR-CT) deep learning segmentation approach that augments training data using pseudo MR images produced by transforming expert-segmented CT images was developed.

Eighty one T2-weighted MRI scans from 28 patients with non-small cell lung cancers (9 with pre-treatment and weekly MRI and the remainder with pre-treatment MRI scans) were analyzed. Cross-modality prior encoding the transformation of CT to pseudo MR images resembling T2w MRI was learned as a generative adversarial deep learning model. This model augmented training data arising from 6 expert-segmented T2w MR patient scans with 377 pseudo MRI from non-small cell lung cancer CT patient scans with obtained from the Cancer Imaging Archive. This method was benchmarked against shallow learning using random forest, standard data augmentation and three state-of-the art adversarial learning-based cross-modality data (pseudo MR) augmentation methods. Segmentation accuracy was computed using Dice similarity coefficient (DSC), Hausdorff distance metrics, and volume ratio.

The proposed approach produced the lowest statistical variability in the intensity distribution between pseudo and T2w MR images measured as Kullback-Leibler divergence of 0.69. This method produced the highest segmentation accuracy with a DSC of (0.75±0.12) and the lowest Hausdorff distance of (9.36 mm+6.00 mm) on the test dataset using a U-Net structure. This approach produced highly similar estimations of tumor growth as an expert (P=0.37).

A novel deep learning MR segmentation was developed that overcomes the limitation of learning robust models from small datasets by leveraging learned cross-modality information using a model that explicitly incorporates knowledge of tumors in modality translation to augment segmentation training. The results show the feasibility of the approach and the corresponding improvement over the state-of-the-art methods Introduction High-dose radiation therapy that is delivered over a few fractions is now a standard of care for lung tumors. The ability to accurately target tumors will enable clinicians to escalate the dose delivered to tumors while minimizing the dose delivered to normal structures. Tumor delineation remains the weakest link in achieving highly accurate precision radiation treatments using computed tomography (CT) as a treatment planning modality. The superior soft tissue contrast of magnetic resonance (MR) images facilitates better visualization of tumor and adjacent normal tissues, especially for those cancers located close to the mediastinum. Such improved visualization makes MR an attractive modality for radiation therapy. Therefore, fast and accurate tumor segmentation on magnetic resonance imaging (MRI) could help to deliver high-dose radiation while reducing treatment complications to normal structures Deep convolutional network-based learning methods are the best-known techniques for segmentation and have been expected to achieve human expert-level performance in image analysis applications in radiation oncology. However, such methods require a tremendous amount of data to train models that are composed of a very large number of parameters. Because MRI is not the standard of care for thoracic imaging, it is difficult to obtain enough MR image sets with expert delineations to train a deep learning method. Deep learning with a large number of MRI for segmenting lung tumors is difficult due to (i) lack of sufficient number of training data as MRI is not standard of care for lung imaging, and (ii) lack of sufficient number of expert delineated contours required for training.

The goal of this work is to compute a robust deep learning model for segmenting tumors from MRI despite lacking sufficiently large expert-segmented MRIs (N>100 cases) for training. This work addresses the challenge of learning from small expert-segmented MR datasets by developing and testing a novel cross-modality deep domain adaptation approach for data augmentation. The approach employs a cross-modality adaptation model encoding the transformation of CT into an image resembling MRI (called pseudo MR) to augment training a deep learning segmentation network with few expert-segmented T2w MR datasets. This cross-modality adaptation model is learned as a deep generative adversarial network (GAN) and transforms expert-segmented CT into pseudo MR images with expert segmentations. The pseudo MR images resemble real MR by mimicking the statistical intensity variations. To overcome the issues of the existing methods, which cannot accurately model the anatomical characteristics of atypical structures, including tumors, a tumor-attention loss that regularizes the GAN model and produces pseudo MR with well-preserved tumor structures is introduced.

FIG. 9 shows example pseudo MR images generated from a CT image using the most recent cross-modality adaptation method called the UNsupervised Image-to-Image Translation (UNIT), the CycleGAN, and the proposed approach. The corresponding T2w MRI for the CT image acquired within a week is also shown alongside for comparison The approach described in this Section include, (a) application of the proposed approach on two additional segmentation networks, the residual fully convolutional networks (Residual-FCN) and dense fully convolutional networks (Dense-FCN), (b) comparison to the more recent image translation approach, called, the unsupervised image to image translation (UNIT), (c) evaluation of longitudinal tumor response monitoring on a subset of patients who had serial weekly imaging during treatment, and finally, (d) benchmarking experiment against a shallow random forest classifier with fully connected random field based tumor segmentation on MRI for assessing performance when learning from a small dataset.

Materials & Materials

Patient and Image Characteristics

A total of 81 T2-weighted (T2 W) MRIs from 28 patients enrolled in a prospective IRB-approved study with non-small lung cancer (NSCLC) scanned on a 3T Philips Ingenia scanner (Medical Systems, Best, Netherlands) before and every week during conventional fractionated external beam radiotherapy of 60 Gy were analyzed. Nine out of the 28 patients underwent weekly MRI scans during treatment for up to seven MRI scans. The tumor sizes ranged from 0.28 cc to 264.37 cc with average of 50.87±55.89 cc. Respiratory triggered two-dimensional (WD) axial T2 W turbo spin-echo sequence MRIs were acquired using a 16-element phased array anterior coil and a 44-element posterior coil and the following scan parameters: TR/TE=3000-6000/120 ms, slice thickness=2.5 mm and in-plane resolution of 1.1×0.97 mm2 flip angle=90°, number of slices=43, number of signal averages=2, and field of view=300×222×150 mm3. Radiation oncologist delineated tumor contours served as ground truth. In addition, CT images with expert delineated contours from an unrelated cohort of 377 patients with NSCLC available from The Cancer Imaging Archive (TCIA) were used for training.

Overview of Approach

The notations used in this work are described in Table 1:

| Notation | Description |
|---|---|
| $\{X_{CT}, y_{CT}\}$ | CT images and expert segmentations |
| $\{X_{MR}, y_{MR}\}$ | MR images and expert segmentations |
| pMR | pseudo MR image |
| pCT | pseudo CT image |
| $G_{CT \to MR}$ | Generator for producing pMR images |
| $G_{MR \to CT}$ | Generator for producing pCT images |
| $D_{CT \to MR}$ | Discriminator to distinguish pMR from real T2w MR images |
| $D_{MR \to CT}$ | Discriminator to distinguish pCT from real CT images |
| $\{L_{adv}, L_{adv}^{MR}, L_{adv}^{CT}\}$ | Total adversarial loss, adversarial loss for pMRI and for pCT |
| $\{L_{cyc}, L_{cyc}^{MR}, L_{cyc}^{CT}\}$ | Total cycle loss, cycle loss for pMR and pCT images |
| $L_{tumor}^{shape}$ | Tumor shape loss |
| $L_{tumor}^{loc}$ | Tumor location loss |

A two-step approach, as shown in FIG. 10A, including: (a) Step 1: CT to pseudo MR expert-segmented dataset transformation, and (b) Step 2: MR segmentation combining expert-segmented T2 W MRI with pseudo MRI produced from Step 1 was employed. Pseudo MR image synthesis from CT was accomplished through cross-modality domain adaption (FIG. 10A(a)) using expert-segmented CTs with unrelated T2w MR images without any expert annotation. Pseudo MR generation is constrained by using two simultaneously trained GANs (transforming CT into MR, and MR into CT). The MR segmentation network in Step 2 uses the translated pseudo MRI with few real T2w MRI for training. FIG. 10A(c)-(e) depicts the losses used for pseudo MR synthesis whereas FIG. 10A(f) corresponds to the segmentation loss.

Cross-Modality Augmented Deep Learning Segmentation:

Image pre-processing: Prior to analysis using the deep networks, all T2 W MR images were standardized to remove patient-dependent signal intensity variations. The CT IHU and MRI intensity values were clipped to (−1000, 500) and (0,667), respectively to force the networks to model the intensity range encompassing thoracic anatomy. The resulting clipped images were normalized to the range [−1,1] to ensure numerical stability in the deep networks that employ tanh functions.

Step 1: Unsupervised Cross-Modality Prior (MR-CT) for Image Translation Learning and Pseudo MR Generation:

The first step in the approach is to learn a cross-modality prior to produce pseudo MR from CT scans in unsupervised way. Unsupervised here refers to learning from CT and MR scans that were acquired from unrelated set of patients, where corresponding images from the two modalities are unavailable. The cross-modality prior is learned as a generational adversarial network (GAN) model, which extracts a model of the anatomical characteristics of tissues in MR and CT using unlabeled MRI and expert-segmented CT scans.

Two GAN networks are trained simultaneously to generate pseudo MRI and pseudo CT from CT and MRI, respectively. Each GAN is composed of a generator and a discriminator that work together in a minmax fashion, whereby the generator learns to produce images that confound the discriminator's classification. The discriminator trains to correctly distinguish between real and synthesized images. This loss is called the adversarial loss $L_{adv}$ (FIG. 10A(c)) and is computed as a sum of losses for generating pseudo MRI and pseudo CT as: $L_{adv}=L_{adv}^{MR}+L_{adv}^{CT}$ shown in eq (1) and (2).

$$L_{adv}^{MR}=E_{x_m \sim x_{MRI}}[\log(D_{MRI}(x_m))]+E_{x_c \sim x_{CT}}[\log(1-D_{MRI}(G_{CT \to MRI}(x_c))]  \quad (1)$$

$$L_{adv}^{CT}=E_{x_c \sim x_{CT}}[\log(D_{CT}(x_c))]+E_{x_{mri} \sim x_{MRI}}[\log(1-D_{CT}(G_{MRI \to CT}(x_m))]  \quad (2)$$

Cycle loss, $L_{cyc}$ as used to soften the requirement for corresponding (e.g. patients) and perfectly aligned source (e.g. CT) and target (e.g. MRI) modalities for training, thereby, allowing unsupervised cross-modality adaptation learning. The cycle consistency loss also prevents the mode collapse endemic to generational adversarial networks. $L_{cyc}$ forces the networks to preserve spatial correspondences between the pseudo and original modalities (see FIG. 10A (d)) and is computed as, $L_{cyc}=L_{cyc}^{MR}+L_{cyc}^{CT}$ for synthesizing pseudo MR and pseudo CT images, as shown in Eq (3):

$$L_{cyc}=E_{x_c \sim x_{CT}}[|(G_{CT \to MRI}(x'_m))-x_c|]+E_{x_m \sim x_{MRI}}[|(G_{MRI \to CT}(x'c))-x_m|]  \quad (3)$$

Where $x'_c$ and $x'_m$ are the generated pseudo CT and pseudo MRI from generator $G_{MRI \to CT}$ and $G_{CT \to MRI}$, respectively. Note that pseudo CTs are simply a by-product of generating the pseudo MR and are generated to add additional regularization in synthesizing pseudo MR images. The network used for implementing the adversarial and the cycle loss uses a standard CycleGAN architecture and consists of a pair of networks with encoders (implemented as a series of stride-2 convolutions for sub-sampling) and decoders (two fractionally strided convolutions) followed by tanh activation for synthesizing the images (see FIG. 10B).

Generator Structure

The generator architectures were adopted from DCGAN, which has been proven to result in stable and faster training of the GANs and avoids issues of mode collapse. Specifically, the generators consist of two stride-2 convolutions, 9 residual blocks and two fractionally strided convolutions with half strides. As done in DCGAN, Rectified Linear Units (ReLU) were used to stabilize the generator network training. Also following the CycleGAN, instance normalization was used in all except the last layer, which has a tanh activation for image generation. The instance normalization was used to yield stable training performance and faster convergence as shown in the CycleGAN method. Details of the structure is shown in FIG. 10B.

Discriminator Structure

The discriminator was implemented using the 70×70 patchGAN, as proposed in pix2pix method. PatchGAN has the benefit that several overlapping 70×70 image patches can be analyzed to compute the synthesis error instead of using a single image. This in turn improves training performance by allowing to back propagate larger errors than is possible when computed by averaging over an entire image. Leaky ReLU was used instead of ReLU as proposed in DCGAN, and batch normalization in all except the first and last layer to stabilize discriminator network training. Details of the structure is shown in FIG. 10B.

Tumor Attention Loss & Network

Adversarial and cycle consistency losses enable a network to only learn transformation of global characteristics as a result of which structures with lots of inter-patient variations such as tumors are lost upon transformation from CT to pseudo MR images. This problem is addressed by introducing a structure-specific, tumor attention loss, $L_{tumor}$.

The tumor attention loss was implemented using a pair of 2D U-Nets that were composed of 4 convolutional and 4 deconvolutional layers with skip connections. Batch normalization was added after each convolution to speed up convergence. The two U-Nets were trained to produce a coarse tumor segmentation using the pseudo MR and the corresponding real CT images. The features from the two networks were aligned (or matched) in the last two layers (indicated by the dotted-red arrow in FIG. 10B(C)). The features from the last two layers were chosen as they contain the most information related to the segmentation of the tumor, such that those features that are most predictive of the tumor will be activated in these layers. Feature alignment is used to force the networks to produce highly similar segmentations. Hence, this loss is called the shape loss (FIG. 10B(C)). Feature alignment then induces an indirect loss in to the cross-modality network when the tumors differ in location and shape in the pseudo MR from the original CT images. The details of this network structure and the feature alignment is shown in FIG. 10B(c).

The tumor attention loss is composed of tumor shape loss, $L_{tumor}^{shape}$ (eq (4)) and tumor location loss, $L_{tumor}^{loc}$ (eq (5)). The tumor shape loss minimizes the differences in the feature map activations (through Euclidean distances) from the penultimate network layer whereas the tumor location loss forces the two networks to produce identical tumor segmentations (through DSC).

$$L_{tumor}^{shape} = \frac{1}{C \times W \times H} \| \phi_{CT}(x_c) - \phi_{CT}(G_{CT \to MRI}(x_c)) \|^2 \quad (4)$$

$$L_{tumor}^{loc} = E_{x_c \sim x_{CT}}[y_c | G_{CT \to MRI}(x_c)] + E_{x_c \sim x_{CT}}[y_c | x_c] \quad (5)$$

where C, W and H are the feature channel, width and height of the feature.

The total loss is computed as:

$$L_{total}=L_{adv}+\lambda_{cyc}L_{cyc}+\lambda_{shape}L_{tumor}^{shape}+\lambda_{loc}L_{tumor}^{loc} \qquad (6)$$

where $\lambda_{cyc}$, $\Delta_{shape}$ and $\Delta_{loc}$ are the weighting coefficients for each loss. The computed losses are back-propagated to update the weights of the networks to produce a pseudo MRI and pseudo CT from the two networks. The algorithm for pseudo MR generation is shown in Algorithm 1.

---
Algorithm 1: CT to pseudo MRI generation
---
Input: CT modality: Xc and label yc, T2w MR modality: $X_m$
Output: pMRI image $X'_m$ and label $X'_m = y$
1  $\theta_G, \theta_D, \theta_T \leftarrow$ initialize
2  for Iters ≤ Max Iter do
3      $X_c, X_m \leftarrow$ images sampled minibatch from CT and MRI
4      Calculate $L_{adv}, L_{cyc}, L_{tumor}^{shape}, L_{tumor}^{loc}$ by equation (1)–(2), (3), (4), (5)
5      $\theta_G \xleftarrow{+} -\Delta_{\theta_G}(L_{adv} + \lambda_{cyc}L_{cyc} + \lambda_{shape}L_{tumor}^{shape} + \lambda_{loc}L_{tumor}^{loc})$
6      Calculate $L_{adv}$ by equation (1) and (2)
7      $\theta_D \xleftarrow{+} -\Delta_{\theta_D}L_{adv}$
8      Calculate $L_{tumor}^{shape}, L_{tumor}^{loc}$ by equation (4) and (5)
9      $\theta_T \xleftarrow{+} -\Delta_{\theta_T}(\lambda_{shape}L_{tumor}^{shape} + \lambda_{loc}L_{tumor}^{loc})$
10 end
---

Step 2: MRI Tumor Segmentation

The pseudo MRI dataset, produced from Step 1, is combined with the few available expert-segmented T2 W MRI scans (N=6) to train a MRI tumor segmentation network. The data augmentation strategy was evaluated for training three different segmentation networks, Residual-FCN, Dense-FCN and U-Net to assess whether the proposed data augmentation method improves performance across multiple networks (FIG. 11). The networks are described below.

Residual-FCN

Our implementation of Residual-FCN, differs from the original implementation in that used the ResNet-50 as a backbone structure instead of the FCN-8s structure for faster training. A schematic of the network structure is shown in FIG. 11(a). The input image was first processed by 7×7 and then 3×3 convolution filters. The resulting number of features are reduced through subsampling through max pooling. These features are then processed by conv2_3 conv3_4, conv4_6 and conv5_3 convolutional layers with residual blocks. The features from the second (conv3_4), third (conv4_6), and fourth (conv5_3) blocks are up-sampled by a scale fact of 8, 16 and 32, similar to the FCN-8s implementation. Those features are summed and passed on to the final output layer that uses sigmoid activation. All convolutional layers are followed by batch normalization. This network has 23.5M parameters.

Dense-FCN

The Dense-FCN is composed of Dense Blocks (DB), which successively concatenates feature maps computed from previous layers, thereby increasing the size of the feature maps. A dense block is produced by iterative concatenation of previous layer feature maps within that block, where a layer is composed of a Batch Normalization, ReLU and 3×3 convolution operation, shown in FIG. 11(b). Such a connection also enables the network to implement an implicit dense supervision to better train the features required for the analysis. Transition Down (TD) and Transition UP (TU) are used for down-sampling and up-sampling the feature size, respectively, where TD is composed of Batch Normalization, ReLU, 1×1 convolution, 2×2 max-pooling while TU is composed of 3×3 transposed convolution. The Dense103 layer structure was used that uses dense blocks with 4, 5, 7, 10 and 12 layers for feature concatenation and 5 TD for feature down-sampling and 5 TU for feature up-sampling, as shown in FIG. 11(b), and resulting in 9.3M parameters. The last layer feature with a size of 256 is converted to the size of 1 by a convolution 1×1 followed by a sigmoid function.

U-Net

The U-Net is composed of series of convolutional blocks, with each block consisting of convolution, batch normalization and ReLU activation. Skip connections are implemented to concatenate high-level and lower level features. Max-pooling layers and up-pooling layers are used to down-sample and up-sample feature resolution size. Four max-pooling and 4 up-pooling were used in the implemented U-Net structure, as shown in FIG. 11(c), which results in 17.2M parameters. The last layer of U-Net contains 64 channels and is converted to 1 channel for prediction by convolution kernel size of 1×1.

Implementation and Training

All networks were trained using 2D image patches of size 256×256 pixels computed from image regions enclosing the tumors. Cross-modality synthesis networks, including the CycleGAN, masked CycleGAN, the UNIT networks, and tumor-aware CycleGAN (our proposed method) were all trained using 32000 CT image patches from 377 patients (scans), and 9696 unlabeled T2 W MR image patches from 42 longitudinal scans of 6 patients, obtained by standard data augmentation techniques, including rotation, stretching, and using different regions of interests containing tumors and normal structures. Segmentation training was performed using 1536 MR images obtained from pre-treatment MRI from 6 consecutive patients and 32000 synthesized MR images from the CT images. The best segmentation model was selected from a validation set consisting of image slices from 36 weekly MRI scans not used for model training. Additional testing was performed on a total of 39 MRI scans obtained from 22 patients who were not used in training or validation. Three of those patients contained longitudinal MRI scans (7,7,6). Table II contains details of the numbers of analyzed scans, patients and ROIs (256×256) used in training and testing.

The Adam optimizer with a batch size of 1 and a learning rate of 0.0001 as used to train the modality translation for all the methods. The learning rate was kept constant for the first 50 epochs and then linearly decayed to zero during the next 50 training epochs. The generator and discriminator is updated during each iteration as similar as in CycleGAN.

In addition to the network structure implementation as described previously, the GAN training was stabilized as proposed in the CycleGAN method. First, least-square loss was used in place of the typically used negative log likelihood. Next, model oscillation was reduced by updating the discriminator using a history of generated images (N=50) as in CycleGAN. All compared translation networks used these same implementation optimizations and were trained with same number of training epochs and training conditions including the datasets for equitable comparison.

TABLE II data for MRI lung image translation and tumor segmentation training

| Unsupervised Image Translation | | | Data Number |
|---|---|---|---|
| CT | Scans | Label | 377 |
| | Patients | | 377 |
| | Images | | 32000 |
| Real MRI | Scans | No | 42 |
| | Patients | Label | 6 |
| | Images | | 9696 |
| Segmentation | | | |
| Training | Translated MRI Scans | Label | 377 |
| | Patients | | 377 |
| | Images | | 32000 |
| | Real MRI Scans | Label | 6 |
| | Patients | | 6 |
| | Images | | 1536 |
| Validation | Real MRI Scans | — | 36 |
| | Patients | | 6 |
| Test | Real MRI Scans | — | 39 |
| | Patients | | 22 |

For segmentation training, the U-Net was trained with batch size of 10, Residual-FCN was trained with batch size of 10 and Dense-FCN was trained with batch size of 6 and initial learning rate of 0.0001. Early stopping were employed with a maximum epoch number of 100 to prevent overfitting. Dice loss was used for the segmentation loss, which shows the ability to reduce the impact of data imbalance. All the networks were trained on Nvidia GTX 1080Ti of 11 GB memory. The ADAM algorithm was used during training with preset parameters $\lambda_{cyc}=10$, $\lambda_{shape}=5$ and $\lambda_{loc}=1$.

Benchmarking Segmentation Performance

The method's performance was benchmarked against a random forest with fully connected random field for segmentation when learning from small dataset, evaluated the segmentation networks (U-Net, Residual-FCN, Dense-FCN) training when augmented with pseudo MRI produced using three different cross-modality synthesis networks including (a) the CycleGAN, (b) masked CycleGAN, and (c) UNsupervised Image-to-image Translation Networks (UNIT) methods.

Random forest classifier baseline: a random forest (RF) segmentation with fully connected conditional random field approach was implemented for the MRI lung tumor segmentation. The feature set was chosen based on the features that have shown to be useful for MRI segmentation applied to brain tumor segmentation. These features included mean intensity, local maximum MRI intensity, local minimum MRI intensity, local mean minimum MRI intensity, mean gradient, std gradient, entropy, context sensitivity features with local patches of size (5×5, 11×11, 17×17, 23×23). Also used were Gabor edge features computed at angles (θ=0, π/4, π/2, 3π/4) and at bandwidth of (γ=0.1, 0.2, 0.3, 0.4) to further improve the accuracy. The RF classifier was trained using 50 trees and maximum depth of 50. Then the voxel-wise RF classifications were further refined by the fully connected conditional random field.

CycleGAN: CycleGAN implementation consisted of the standard CycleGAN method as described before, forming an unsupervised image translation.

Masked CycleGAN: The main difference between masked CycleGAN and CycleGAN is that it uses expert-segmentations on both CT and MRI modalities as an additional input channel to specifically focus training on the regions containing tumors. This method requires expert segmented datasets from both imaging modalities for image translation.

UNIT: Similar to CycleGAN and proposed method, UNIT performs unsupervised image translation, wherein corresponding source and target images or expert segmentation on both modalities are not required. The primary difference of this approach is in its encoder structure in the generator that uses a variational autoencoder (VAE) with cycle consistency loss. The encoder models the modality transformation as a latent code that is then used to generate images through a generator. The default implementation was used as described in UNIT, where the last layer of the encoder and first layer of the generator for both CT to MRI translation and MRI to CT translation networks are shared. The discriminator uses six convolutional layers as used in the original implementation.

Evaluation Metrics

The similarity of pseudo MRI to the T2w MRI was evaluated using Kullback-Leibler divergence (K-L divergence), that quantifies the average statistical differences in the intensity distributions. The K-L divergence was computed using the intensity values within the tumor regions by comparing the intensity histogram for all the generated pseudo MR images and the intensity histogram computed from the training T2w MR images. The KL divergence measure quantifies the similarity in the overall intensity variations between the pseudo MR and the real MR images within the structure of interest, namely, tumors. The K-L divergence is calculated by eq. 7:

$$D_{KL}(P_{sMRI} \| Q_{rMRI}) = \sum P_{sMRI} \ln \frac{P_{sMRI}}{Q_{rMRI}} \qquad (7)$$

where $P_{sMRI}$ and $Q_{rMRI}$ indicate the tumor distribution in pseudo MR and T2w MR images and the summation is computed over a fixed number of discretized intensity levels (N=1000).

The segmentation accuracy was computed using DSC and Hausdorff distance. The DSC is calculated between the algorithm and expert segmentation as:

$$DSC = \frac{2TP}{FP + 2TP + FN} \qquad (8)$$

where, TP is the number of true positives, FP is the number of false positives, and FN is the number of false negatives.

The Hausdorff distance is defined as:

$$Haus(P, T) = \max\{\sup_{p \in S_P} \inf_{t \in S_T} d(p, t), \sup_{t \in S_T} \inf_{p \in S_P} d(t, p)\} \qquad (9)$$

where, P and T are expert and segmented volumes, and p and t are points on P and T, respectively. $S_p$ and $S_t$ correspond to the surface of P and T, respectively. To remove the influence of noise during evaluation, Hausdorff Distance (95%) was used. Also calculated is the relative volume ratio, computed as $$VR = \frac{|V_{as} - V_{gs}|}{V_{gs}},$$

where $V_{as}$ is the volume calculated by algorithm while $V_{gs}$ is the volume calculated by manually segmentation.

Finally, for those patients who had longitudinal follow ups, the tumor growth trends were computed using the Theil-Sen estimator, which measures the median of slope (or tumor growth) computed from consecutive time points as $$l(\delta_v) = \underset{l_i < l_k}{\text{median}\lim}\left(\frac{l(v_k) - l(v_i)}{t_k - t_i}\right) \quad (10)$$

where $v_k$, $v_i$ are the tumor volumes at times k and i for a lesion l. The difference in growth rate between algorithm and the expert delineation was computed using the Student's T-test.

FIG. 10C is a block diagram of a system 1000 for training models for segmenting biomedical images based on cross-domain adaptations. In overview, the system 1000 may include an image segmentation system 1002, at least one imaging device 1004, and at least one display 1006. The image segmentation system 1002 may be communicatively coupled with the imaging device 1004 and the display 1006. The image segmentation system 1002 may include a model applier 1008, a model trainer 1010, a set of synthesis models 1012A-N (hereinafter generally referred to synthesis models 1012), a set of segmentation models 1014A-N (hereinafter generally referred to as segmentation models 1014), and a training dataset 1016, among others. Each synthesis model 1012 may be for a different modality of biomedical imaging (e.g., CT, MRI, or various sequences for MRI). Each synthesis model 1012 may have at least one generator network 1020 and at least one discriminator unit 1022. Each segmentation model 1014 may be for a different modality of biomedical imaging. The training dataset 1016 may include a set of sample tomographic biomedical images 1018A-N (hereinafter generally referred to as sample images 1018). Each of the components in the system 1000 listed above may be implemented using hardware (e.g., one or more processors coupled with memory) or a combination of hardware and software as detailed herein in Section E. Each of the components in the system 1000 may implement or execute the functionalities detailed herein in Section B (e.g., those described in conjunction with FIGS. 6B-I), C, and D (e.g., those described in conjunction with FIGS. 10A and 10B).

The imaging device 1004 may perform a biomedical imaging scan on a subject to acquire or generate at least one tomographic biomedical image. The tomographic biomedical image may be used as a sample tomographic biomedical image for the training dataset 1016. The imaging device 1004 may be in any modality of biomedical imaging. The imaging device 1004 may include a PET-computed tomography (CT) scanner, an X-ray CT Scanner, a SPECT CT scanner, an MRI scanner, an ultrasound scanner, and a photoacoustic scanner, among others. To scan, the imaging device 1004 may be pointed toward a designated area on an outer surface of the subject (e.g., human or animal). As the subject is scanned, the imaging device 1004 may generate a projection dataset corresponding to the tomographic biomedical image. The project dataset may correspond to a cross-sectional plane or a volume of the subject through the predesignated area. The projection dataset may be two-dimensional or three-dimensional visualized representation of the subject, including the inner anatomical and physiological structure of the subject.

The projection dataset may include one or more data counts. The projection dataset may include the one or more data counts in accordance with any data structure, such as an array, a binary tree, a matrix, a linked list, a heap, a hash table, a stack, or a queue, among others. Each data count may correspond to a coordinate of the scanned cross-sectional plane or the volume of the subject. When the cross-sectional plane of the subject is scanned, the projection dataset may be two-dimensional and the coordinates of the data counts may also be two-dimensional. When the volume of the subject is scanned, the projection dataset may be three-dimensional and the coordinates for the data counts may also be three-dimensional. The number of data counts in the projection dataset may depend on a sampling rate of the biomedical imaging scan performed by the imaging device 1004.

The display 1006 may present or render an image (e.g., a segmented version of the tomographic biomedical image identified from the imaging device 1004) output by the image segmentation system 1002. In some embodiments, the display 1006 may present or render the reconstructed image generated by the CED model 212 of the image segmentation system 1002. The display 1006 may include any monitor, such as a liquid crystal display (LCD), an organic light-emitting diode (OLED) monitor, and a cathode ray tube (CRT), among others. The display 1006 may be communicatively coupled with the image segmentation system 1002, and may render and output the image from the image segmentation system 1002.

The model applier 1008 (or the model trainer 1010) may establish and maintain the set of synthesis models 1012, including the generator unit 1020 and the synthesis unit 1022 in each synthesis model 1012. In addition, the model applier 1008 (or the model trainer 1010) may establish and maintain the set of segmentation model 1014. The synthesis models 1012 and the segmentation models 1014 may be instances of the models detailed herein in conjunction with FIGS. 6B-6I, 10A, and 10B. The details of the functionalities and structures are further provided herein below.

Each synthesis model 1012 may transform, translate, or otherwise convert tomographic biomedical image from an initial imaging modality (e.g., CT, MRI, or any sequence of MRI) to a target imaging modality (e.g., CT, MRI, or any sequence of MRI). Each synthesis model 1012 may be configured or dedicated to converting images from one imaging modality to another imaging modality. For example, the first synthesis model 1012A may convert images from MRI to CT and the second synthesis model 1012B may convert images from CT to MRI. The synthesis model 1012 may be any model to convert the images from one modality to another modality, such as a generative adversarial network (GAN) (e.g., architectures as described above). The tomographic biomedical images provided to the synthesis model 1012 may be acquired from different subjects and thus may be independent of one another or lack correspondences. Furthermore, the resultant output of one synthesis model 1012 for one imaging modality may be used to train another synthesis model 1012 of another imaging modality. In this manner, the synthesis model 1012 may generate additional tomographic biomedical images with which to train itself and the segmentation models 1014.

The synthesis model 1012 may retrieve, receive, or otherwise identify a tomographic biomedical image of one imaging modality as an input. The synthesis model 1012 may apply the image to the generator unit 1020 and the discriminator unit 1022 to generate another tomographic biomedical image of another imaging modality as an output. In the synthesis model 1012, the generator unit 1020 and the discriminator unit 1022 may be arranged in series. The input for the synthesis model 1012 may be connected to the input of the generator unit 1020. The output of the generator unit 1020 may be connected to the input of the discriminator unit 1022. The output of the discriminator model 1022 may be connected to the output of the synthesis model 1012.

The generator unit 1020 of the synthesis model 1012 may include a set of transform layers to generate the tomographic biomedical images of one imaging modality using the tomographic biomedical images of another imaging modality. In some embodiments, the generator unit 1020 may be in accordance with any number of generative networks, such as a deconvolution neural network, a Gaussian network, an auto-encoder, a Boltzmann machine, and a hidden Markov model, among others. The set of transform layers in the generator unit 1020 can include one or more parameters (e.g., weights) to modify or otherwise process the set of feature maps inputted into the generator unit 1020 to produce or generate an output set of feature maps for generating the image of the different modality. The set of transform layers in the generator unit 1020 can be arranged in series, with an output of one transform layer fed as an input to a succeeding transform layer. Each transform layer may have a non-linear input-to-output characteristic. In some embodiments, at least some of the transform layers in the generator unit 1020 may be a deconvolutional neural network, and may include an upsampler, a deconvolutional layer, a normalization layer, and an activation layer (e.g., a rectified linear unit (ReLU)), among units. In some embodiments, at least some of the transform layers in the generator unit 1020 may be a convolutional neural network, and may include a convolutional layer, a normalization layer, and an activation layer (e.g., a rectified linear unit (ReLU)), among units. In some embodiments, the generator unit 1020 may also include at least one residual block parallel to a subset of the transform layers. The residual block may combine (e.g., concatenate or weighted sum) the output from one transform layer with the output from a previous transform layer. Subsets of consecutive transform layers can be grouped as a network within the generator unit 1020.

The discriminator unit 1022 of the synthesis model 1012 may include a set of transform layers to evaluate the tomographic biomedical images generated by the generator unit 1020 by determining loss or error metrics. In some embodiments, the discriminative unit 1022 may be in accordance with any number of discriminative networks, such as a convolutional neural network, a linear regression model, a logistic regression model, and random forests, among others. The set of transform layers in the discriminator unit 1022 can include one or more parameters (e.g., weights) to modify or otherwise process the set of feature maps to evaluate the generator unit 1020. The set of transform layers in the discriminator unit 1022 can be arranged in series, with an output of one transform layer fed as an input to a succeeding transform layer. Each transform layer may have a non-linear input-to-output characteristic. In some embodiments, the transform layers in the discriminator unit 1022 may be a convolutional neural network, and may include a convolutional layer, a normalization layer, and an activation layer (e.g., a rectified linear unit (ReLU)), among units. Subsets of consecutive transform layers can be grouped as a network within the discriminator unit 1022.

Each segmentation model 1014 may generate segmented tomographic biomedical image from an original tomographic biomedical image provided to the segmentation model 1014. The segmentation model 1014 may retrieve, receive, or identify a tomographic biomedical image generated by one of the synthesis models 1012. In some embodiments, the segmentation model 1014 may be any model to generate segmented tomographic biomedical images, such as a U-net (e.g., as detailed herein in Sections B and D), convolutional neural network (CNN), a pulse-coupled neural network (PCNN), long-term short memory (LSTM), and a self-organizing feature map (SOFM), among others. The segmentation model 1014 may include a set of transform layers to generate the segmented tomographic biomedical images using the images generated by the synthesis model 1012. The set of transform layers in the segmentation model 1014 can include one or more parameters (e.g., weights) to modify or otherwise process the set of feature maps used to generate the segmented images. The set of transform layers in the segmentation model 1014 can be arranged in series, with an output of one transform layer fed as an input to a succeeding transform layer. Each transform layer may have a non-linear input-to-output characteristic. In some embodiments, the transform layers in the segmentation model 1014 may include a convolutional layer, a normalization layer, and an activation layer (e.g., a rectified linear unit (ReLU) and sigmoid function), among units. Subsets of consecutive transform layers can be grouped as a network within the segmentation model 1014.

With the establishment of the models 1012 and 1014, the model applier 1008 may retrieve, receive, or otherwise identify sample images 1018 to train the synthesis models 1012 and the segmentation models 1014. The sample images 1018 of the training dataset 1016 may be tomographic biomedical images and may be of different biomedical imaging modalities. For example, the first sample image 1018A may be of a first imaging modality and the second sample image 1018B may be of a second imaging modality different from the first imaging modality. The imaging modalities may include, for example, CT, MRI, PET, X-ray CT, PET-CT, and PET-MRI, among others. In some embodiments, for the same type of imaging, images using different parameters may be considered as different modalities. For example, MRI using spin echo, gradient echo, inversion, weighting, and different sequences may be considered different modalities from one another. In addition, the sample images 1018 may be independent of each other. For example, the sample images 1018 may be acquired from different subjects via one or more imaging devices 1004. In some embodiments, the sample images 1018 may have different coordinates and alignment from each other.

The model applier 1008 may apply the synthesis models 1012 to the sample images 1018. At least two sample images 1018 may be applied to train the synthesis model 1012. In some embodiments, the model applier 1008 may identify the imaging modality for each sample image 1018. In some embodiments, the model applier 1008 may identify an initial imaging modality and target imaging modality to which to convert to for each synthesis model 1012. The model applier 1008 may compare the imaging modalities of the synthesis models 1012 with the imaging modalities for the sample images 1018. Based on the comparison, the model applier 1008 may identify the synthesis model 1012 having the same initial imaging modality as the imaging modality of the sample image 1018 and the same target imaging modality as the imaging modality of another sample image 1018. With the identification, the model applier 1008 may provide or feed the sample image 1018 into the corresponding synthesis model 1012.

In applying the synthesis models 1012, the model applier 1008 may simultaneously or concurrently perform the functionalities of the generator unit 1020 and the discriminator unit 1022 of the synthesis model 1012. The model applier 1008 may retrieve, receive, or identify outputs from the synthesis model 1012. The output may be synthesized tomographic biomedical images of an imaging modality different from the initial imaging modality of the input sample image 1018. For example, the model applier 1008 may retrieve the first sample image 1018A converted from the first imaging modality to the second imaging modality from the first synthesis model 1012A. Conversely, the model applier 1008 may retrieve the second sample image 1018B converted from the second imaging modality to the first imaging modality from the second synthesis model 1012B.

Using the outputs from the synthesis models 1012, the model trainer 1010 may determine one or more synthesis losses for each synthesis model 1012. In some embodiments, the model trainer 1010 may determine the one or more synthesis losses from the discriminator unit 1022 in each synthesis model 1012. The synthesis loss may indicate at least one difference among the images 1018 translated from one imaging modality to another imaging modality. In general, the synthesis loss may identify inaccuracies in the generation of structures of interest (e.g., objects within the image 1018) in the conversion from one imaging modality to another imaging modality. The synthesis loss may include the adversarial loss, the cycle loss, the structure loss, the texture loss, shape loss, as detailed herein in conjunction with FIGS. 6B-6I, 10A, and 10B, among others. In some embodiments, the synthesis loss may indicate a loss in textural characteristics in the conversion. The textual loss may indicate differences in image texture of objects (e.g., regions of interest such as tumors or lesions) and internal structure in the image 1018 due to the conversion. In some embodiments, the synthesis loss may indicate a loss in shape from the conversion. The shape loss may indicate differences in shapes of objects (e.g., regions of interest such as tumors or lesions) and global characteristics from performing the transformation from one imaging modality to another imaging modality.

To determine the synthesis losses, the model trainer 1010 may compare among the original sample images 1018 and converted, output images 1018 from the synthesis model 1012. For example, the model trainer 1010 may compare the first sample image 1018A converted by the first synthesis model 1012A from the first imaging modality to the second imaging modality with the original second sample image 1018B to calculate the synthesis loss for the first synthesis model 1012A. Furthermore, the model trainer 1010 may compare the second sample image 1018B translated by the second synthesis model 1012B from the second imaging modality to the first imaging modality with the original first sample image 1018A to calculate the synthesis loss for the second synthesis model 1012B.

In conjunction with the calculation of the synthesis losses for the synthesis models 1012 calculated, the model applier 1010 may apply the segmentation models 1014 to the resultant images 1018 from the synthesis models 1012. At least two resultant sample images 1018 from the synthesis models 1012 may be applied to train the segmentation models 1014. In some embodiments, the model applier 1008 may identify the imaging modality for each resultant sample image 1018. In some embodiments, the model applier 1008 may identify an imaging modality for each segmentation model 1014. The model applier 1008 may compare the imaging modalities of the segmentation model 1014 with the imaging modalities for the resultant sample images 1018. Based on the comparison, the model applier 1008 may identify the segmentation model 1014 having the same initial imaging modality as the imaging modality of the sample image 1018 outputted from one of the synthesis models 1012.

With the identification, the model applier 1008 may provide or feed the resultant image 1018 into the corresponding segmentation model 1014. For example, the first resultant image 1018A from the first synthesis model 1012A may be of the second imaging modality and the second resultant image 1018B from the second synthesis model 1012B may of the first imaging modality. Furthermore, the first segmentation model 1014A may be for the first imaging modality and the second segmentation model 1014B may be for the second imaging modality. In this example, based on the identifications the model applier 1008 may apply the first segmentation model 1014A to the second resultant image 1018B of the first imaging modality. In addition, the model applier 1008 may apply the second segmentation model 1014B to the first resultant image 1018A of the second imaging modality. In applying the segmentation models 1014, the model applier 1008 may simultaneously or concurrently perform the transform layers of the segmentation model 1014. The model applier 1008 may retrieve, receive, or identify outputs from the segmentation model 1014. The output may be segmented tomographic biomedical images from one of the sample images 1018.

Using the outputs from the segmentation model 1014, the model trainer 1010 may calculate or determine object attention losses. In general, object attention loss may indicate a discrepancy in feature alignment for objects in the image 1018 and in the transform layers among segmentation models 1014. In some embodiments, the objection attention loss determined by the model trainer 1010 may include the object shape loss and the object location loss, as detailed herein in conjunction with FIGS. 6B-6I, 10A, and 10B, among others. In some embodiments, the object attention loss may indicate difference for individual transform layers between the segmentation models 1014.

To determine the object attention loss, the model trainer 1010 may identify one or more transform layers from each segmentation model 1014. The one or more transform layers to be identified by the model trainer 1010 may be predefined. For example, the model trainer 1010 may identify the last transform layer in the penultimate network in each segmentation model 1014. In some embodiments, the model trainer 1010 may identify the different transform layers for different types of object attention losses (e.g., object shape loss and object location loss). With the identification of the one or more transform layers, the model trainer 1010 may compare between corresponding transform layers across the segmentation models 1014 of different imaging modalities. Based on the comparison, the model trainer 1010 may calculate the object attention loss for each segmentation model 1014. In some embodiments, the calculation of the object attention loss may be in accordance with a Manhattan distance, a Euclidean distance, or any other p-norm, among others.

In some embodiments, the model trainer 1010 may determine a segmentation loss between the resultant image 1018 from the segmentation model 1014 and an annotated image from the training dataset 1016. The annotated image may correspond to the original sample image 1018 used by the synthesis model 1012 and the segmentation model 1014 to generate the resultant image 1018. The segmentation loss may indicate one or more differences between the resultant image 1018 and the corresponding annotated image. In some embodiments, the model trainer 1010 may use any defined function to calculate the segmentation loss, such as a Manhattan distance, a Euclidean distance, or any otherp-norm, among others.

Based on the determined losses, the model trainer 1010 may change, alter, or otherwise modify one or more of the parameters in the set of synthesis models 1012 and the set of segmentation models 1014. In some embodiments, the model trainer 1010 may apply backpropagation of the determined losses to the synthesis model 1012 and the segmentation model 1014 to update the parameters, as discussed herein. In some embodiments, the model trainer 1010 may use the synthesis losses and the object attention losses to modify the parameters of the corresponding synthesis model 1012. In some embodiments, the model trainer 1010 may use the synthesis losses, the object attention losses, the segmentation losses to modify the parameters of the corresponding segmentation model 1014. The training of the synthesis models 1012 and the segmentation models 1014 may continue until convergence of the parameters in the models 1012 and 1014 (e.g., margin less than a convergence threshold). In this manner, the training of the synthesis model 1012 and the segmentation models 1014 may be performed without supervision, thus eliminating the involvement of expert annotated examples of biomedical images. The system 1000 may thus scale new imaging modalities to treatment and other applications in which there may not be a large number of expert annotated training datasets.

With the training of the models 1012 and 1014, the model applier 1008 may retrieve, receive, or otherwise identify a tomographic biomedical image acquired from the imaging device 1004 for runtime operations. The acquired image may be of the image modality of the imaging device 1004. The model applier 1008 may apply the acquired image to the segmentation model 1014 for the imaging modality. In some embodiments, the model applier 1008 may identify the imaging modality of the acquired image. Using the identified modality, the model applier 1008 may find the segmentation model 1014 corresponding to the image modality of the acquired image. Upon identification, the model applier 1008 may apply the segmentation model 1014 to the acquired image to generate a segmented image. In some embodiments, the model applier 1008 may present or display the segmented image generated from the segmentation model 1014 on the display device 1006.

In some embodiments, the model applier 1008 may use the generated segmented image to determine a health metric of the subject from which the original image was acquired via the imaging device. The health metric may include those detailed herein in conjunction with Sections C and D. The health metric may be used to predict response or early development of resistance to immunotherapy. The determination of the health metric may be based on objects recognized from the segmented image. The object may be identified using computer vision techniques, such as feature detection, among others.

FIG. 10D is a flow diagram of an example method 1050 of training models for segmenting biomedical images based on cross-domain adaptations. The functionalities of the method 1050 may be implemented or performed using the architecture described in this section (e.g., the architecture described herein in conjunction with FIGS. 6B-I and 10A-C) or the computing system 1500 described below in conjunction with FIG. 15A-D. A computing device may identify biomedical image of different modalities (1052). The computing device may apply synthesis models (1054). The computing device may generate synthesized images (1056). The computing device may determine losses from synthesis (1058). The computing device may apply segmentation models (1060). The computing device may generate segmented images (1062). The computing device may determine object attention losses (1064). The computing device may modify models using the determined losses (1066).

Results

Impact of the Proposed Tumor-Attention Loss in CT to MRI Transformation

FIGS. 12A and 12B show MRI produced using the proposed schema, CycleGAN, masked CycleGAN and UNIT for three representative examples. The expert-segmented tumor contour placed on the CT is shown at the corresponding locations on the pseudo MRI. As shown, this method produced the best preservation of tumors on the pseudo MR images.

As shown, the proposed method most closely approximated the distribution of MR single intensities as the T2w MRI. The algorithm generated tumor distribution was computed within the tumors of the 377 pseudo MRI produced from CT, while the T2w MR distribution was obtained from tumor regions from expert-segmented T2w MR used in validation (N=36). This was confirmed on quantitative evaluation wherein, the present method resulted in the lowest KL divergence of 0.069 between the pseudo MRI and T2w MRI compared with the CycleGAN (1.69), the masked CycleGAN (0.32) and UNIT (0.28) with 1000 bins to obtain a sufficiently large discretized distribution of intensities, as shown in FIG. 12B.

Impact of Data Augmentation Using Transformed MRI on Training U-Net-Based MRI Tumor Segmentation FIG. 13 shows segmentation results from five randomly chosen patients computed using random forest classifier (RF+fCRF) (FIG. 13a) and with a U-Net trained with only few T2w MRI (FIG. 13b), and U-Nets trained T2w MRI and augmented data or pseudo MRI, corresponding to semi-supervised training and produced through cross-modality augmentation produced using cycle-GAN (FIG. 13c), masked CycleGAN (FIG. 13d), UNIT (FIG. 13e) and the proposed approach (FIG. 13g). FIG. 13f shows the results of training with only pseudo MRI produced using proposed method in order to assess this method's performance when using only augmented pseudo MR data. This mode setting corresponds to unsupervised domain adaptation. As shown, the both the semi-supervised and unsupervised modes of the proposed method's generated contours closely approximate expert-segmentation (FIG. 13g, FIG. 13f). The UNIT method also led to performance improvements compared with the CycleGAN and masked CycleGAN methods, but was less accurate than the present method. The overall segmentation accuracy using DSC and Hausdorff distances for these methods, including the RF+CRF methods are shown in Table III. As shown, the present method resulted in the highest DSC and lowest Hausdorff distances on test sets that were not used either in training or model selection.

Impact of Network Architecture on Tumor Segmentation Accuracy

The segmentation accuracy was evaluated on two additional segmentation networks, Residual-FCN and Dense-FCN, to assess whether the data augmentation using the proposed method improved segmentation accuracy in those networks. Table IV summarizes the segmentation accuracy achieved when using the different data augmentation strategies. Also shown is the performance of the networks trained with no T2w MR but using only the pseudo MR images produced using proposed tumor-aware augmentation. As seen (Table III, IV), the proposed tumor-aware data augmentation resulted in most accurate segmentations in both networks, including when using the unsupervised training mode (with pseudo MR only training) in the test set. UNIT's accuracy was consistently higher than the masked cycle GAN in all three networks in the test set.

TABLE III

Segmentation accuracies computed using the U-Net for the different data augmentation strategies. Segmentation accuracies are shown using Dice similarity coefficient (DSC), 95th percentile Hausdorff distance (HD95) and volume ratio (VR) metrics.

| | U-Net | | | | | |
|---|---|---|---|---|---|---|
| | Validation | | | Test | | |
| Method | DSC | HD95 mm | VR | DSC | HD95 mm | VR |
| RF + fCRF | 0.51 ± 0.16 | 12.88 ± 10.66 | 0.56 ± 0.61 | 0.55 ± 0.19 | 14.58 ± 10.26 | 0.57 ± 0.47 |
| Standard augmentation of T2w MRI | 0.63 ± 0.27 | 7.22 ± 7.19 | 0.34 ± 0.31 | 0.50 ± 0.26 | 18.42 ± 13.02 | 0.54 ± 0.27 |
| CycleGAN pseudo MRI and T2w MRI | 0.57 ± 0.24 | 11.41 ± 5.57 | 0.50 ± 0.53 | 0.62 ± 0.18 | 15.63 ± 10.23 | 0.54 ± 1.27 |
| masked CycleGAN pseudo and T2w MR | 0.67 ± 0.21 | 7.78 ± 4.40 | 0.84 ± 0.30 | 0.56 ± 0.26 | 20.77 ± 18.18 | 0.37 ± 0.57 |
| UNIT | 0.63 ± 0.29 | 7.74 ± 4.80 | 0.45 ± 0.27 | 0.63 ± 0.22 | 17.00 ± 14.80 | 0.47 ± 0.28 |
| Tumor-aware pseudo MR and T2w MR | 0.70 ± 0.19 | 5.88 ± 2.88 | 0.23 ± 0.15 | 0.75 ± 0.12 | 9.36 ± 6.00 | 0.19 ± 0.15 |
| Tumor-aware pseudo MR | 0.62 ± 0.26 | 7.47 ± 4.66 | 0.35 ± 0.29 | 0.72 ± 0.15 | 12.45 ± 10.87 | 0.25 ± 0.19 |

TABLE IV segmentation accuracy comparison of Residual-FCN (RFCN) and Dense-FCN (DFCN). Segmentation accuracies are shown using Dice similarity coefficient (DSC), $95^{th}$ percentile Hausdorff distance (HD95) and volume ratio (VR) metrics.

| | | Validation | | | Test | | |
|---|---|---|---|---|---|---|---|
| Method | Networks | DSC | HD95 mm | VR | DSC | HD95 mm | VR |
| Standard augmentation of T2w MRI | RFCN | 0.62 ± 0.24 | 9.31 ± 5.30 | 0.33 ± 0.29 | 0.50 ± 0.19 | 23.96 ± 17.00 | 0.48 ± 0.23 |
| | DFCN | 0.68 ± 0.28 | 8.06 ± 4.89 | 0.29 ± 0.25 | 0.57 ± 0.23 | 24.98 ± 16.51 | 0.51 ± 0.99 |
| CycleGAN pseudo MRI and T2w MRI | RFCN | 0.47 ± 0.27 | 11.71 ± 5.99 | 0.41 ± 0.30 | 0.52 ± 0.20 | 17.82 ± 12.11 | 0.54 ± 0.89 |
| | DFCN | 0.60 ± 0.27 | 10.29 ± 6.22 | 0.34 ± 0.26 | 0.60 ± 0.19 | 23.77 ± 17.61 | 0.35 ± 0.55 |
| masked CycleGAN pseudo and T2w MR | RFCN | 0.42 ± 0.28 | 16.01 ± 7.65 | 0.44 ± 0.31 | 0.54 ± 0.25 | 20.36 ± 12.02 | 0.54 ± 1.46 |
| | DFCN | 0.60 ± 0.23 | 9.85 ± 6.85 | 0.48 ± 0.35 | 0.55 ± 0.24 | 25.11 ± 20.89 | 0.47 ± 0.33 |
| UNIT pseudo and T2w MR | RFCN | 0.65 ± 0.24 | 9.03 ± 5.03 | 0.36 ± 0.40 | 0.59 ± 0.22 | 17.49 ± 19.48 | 0.38 ± 0.26 |
| | DFCN | 0.66 ± 0.20 | 7.43 ± 4.28 | 0.43 ± 0.42 | 0.58 ± 0.24 | 28.37 ± 22.94 | 0.47 ± 0.30 |
| Tumor-aware pseudo MR and T2w MR | RFCN | 0.70 ± 0.21 | 7.56 ± 4.85 | 0.22 ± 0.16 | 0.72 ± 0.15 | 16.64 ± 5.85 | 0.25 ± 0.22 |
| | DFCN | 0.68 ± 0.20 | 7.37 ± 5.49 | 0.27 ± 0.28 | 0.73 ± 0.14 | 13.04 ± 6.06 | 0.21 ± 0.19 |
| Tumor-aware pseudo MR | RFCN | 0.59 ± 0.23 | 10.09 ± 5.88 | 0.36 ± 0.32 | 0.69 ± 0.17 | 18.03 ± 12.91 | 0.27 ± 0.25 |
| | DFCN | 0.62 ± 0.21 | 11.09 ± 5.02 | 0.42 ± 0.29 | 0.67 ± 0.16 | 20.70 ± 10.57 | 0.22 ± 0.19 |

Comparison of Longitudinal Segmentations Produced Using Algorithm and Expert

The ability of these methods is assessed to longitudinally segment and measure tumor response to radiation therapy. FIG. 14 shows the estimate of tumor growth computed using the proposed method used to train a U-Net from three patients with weekly MR scans who were not used for training. This method produced a highly similar estimate of tumor growth as an expert as indicated by the differences in tumor growth computed between algorithm and expert segmentation (week one only: 0.067±0.012; CycleGAN: 0.038±0.028; masked Cycle-GAN: 0.042±0.041; UNIT: 0.034±0.031; proposed: 0.020±0.011).

Discussion

A novel approach for augmenting the training of deep neural networks for segmenting lung tumors from MRI with limited expert-segmented training sets was developed. The present approach uses the structure of interest, namely tumor to constrain the CT to MR translation such that the generated pseudo MR preserve the location and shape of the tumors. Global distribution matching methods such as the Cycle-GAN cannot accurately model the transformation of less frequent structures like tumors and result in loss of the tumors in the transformed pseudo MRI. The present method also outperformed the more recent UNIT method that uses variational autoencoders that specifically learn a parametric function (typically a Gaussian) controlling the transformation between modalities. Results show that data augmentation obtained using the present method improves segmentation accuracy and produced the most accurate segmentation of the compared methods regardless of the chosen segmentation architecture (U-Net, Residual-FCN, and Dense-FCN).

Also the performance of the present method was benchmarked against a shallow-learning based random forest classifier, when training with standard data augmentation, and when using only the pseudo MR data produced using the present method. It was found that the random forest classifier produced much lower accuracies due to large number of false positives when compared with all other deep learning methods, confirming prior results that deep learning methods are indeed capable of learning more accurate representation of the underlying data and lead to better classification/segmentation.

The proposed method improved the segmentation performance of other domain adaptation methods despite using only few MRI datasets for training. In fact, it was found that adding any cross-modality augmentation is better than standard augmentation strategies. This is because, the present method like in, leverages labeled information from other imaging modalities to boost the performance in the target imaging modality. Solutions include using networks pre-trained on the same modality but a different task as in or training a cross-modality model to synthesize images resembling the target distribution and as done in the present disclosure. However, for such methods to work, the approximated model is to closely match the target distribution. As shown in the results, the pseudo MRI produced using the present method resulted in the closest match to the T2-w MRI tumor distribution measured by the K-L divergence. Therefore, this led to improved performance as the information from the unrelated, yet relatively large expert-segmented CT modality (N=377 cases) could be better leveraged to improve the performance despite having a small MRI training set. This is further underscored by the result that segmentation networks trained using only the pseudo MRI produced using the present method yielded more accurate segmentations (on test) compared with other cross-modality augmentation methods that included some of the T2w MRI for training.

Prior works have used cycle loss to learn the cross-modality prior to transform modalities, where the network learns the transformation by minimizing global statistical intensity differences between the original and a transformed modality (e.g., CT vs. pseudo CT) produced through circular synthesis (e.g., CT to pseudo MR, and pseudo MR to pseudo CT). Although cycle loss eliminates the need for using perfectly aligned CT and MRI acquired from the same patient for training, it cannot model anatomical characteristics of atypical structures, including tumors. In fact, cycle-GAN based methods have been shown to be limited in their ability to transform images even from one MR to a different MR sequence. This approach overcomes the limitations of the prior approaches by incorporating structure-specific losses that constrain the cross-modality transformations to preserve atypical structures including tumors. However, it is noted that all of these methods produce pseudo MR representations that do not create synthetic MR images modeling the same tissue specific intensities as the original MRI. This is intentional as the goal is simply to create an image representation that resembles an MRI and models the global and local (structure of interest) statistical variations that will enable an algorithm to detect and segment tumors. The fact that the pseudo MR images are unlike T2w MRI is demonstrated by the lower accuracy particularly on test sets when excluding any T2w MRI from training. However, it is notable that the pseudo MR images produced by the method still lead to more accurate segmentations compared with other approaches.

The higher DSC accuracy is speculated in the test sets resulted from the larger tumor volumes in the test 70.86±59.80 cc when compared with validation set of 31.49±42.67 cc. It is known that larger tumors can lead to higher DSC accuracies and can lead to more optimistic bias in the accuracy. The reason for the differences in tumor volumes arose since the validation set used patients (N=6) with both pre-treatment (larger tumors) and during treatment (acquired during weekly treatment) MRI where there the tumors shrunk as they responded to treatment. On the other hand resulting in a total of 36 scans, the test set used only 3 patients with pre- and during-treatment MRIs (N=20), and the remaining (N=19) were all comprised of pre-treatment MRI. The reason for this set up is primarily because additional pre-treatment MRIs were included for testing only after the training models were finalized for blinded evaluation on new samples.

Unlike most prior works that employ transfer learning to fine tune features learned on other tasks, such as natural images, a data augmentation approach was chosen using cross-modality priors. The reason for this is transfer learning performance on networks trained on completely unrelated datasets is easily surpassed even when training from scratch using sparse datasets. This is because features of deeper layers may be too specific for the previously trained task and not easily transferable to a new task. The approach overcomes the issue of learning from small datasets by augmenting training with relevant datasets from a different modality.

This work has a few limitations. First, the approach is limited by the number of test datasets, particularly for longitudinal analysis due to the lack of additional recruitment of patients. Second, due to lack of corresponding patients with CT and MRI, it is not possible to evaluate the patient level correspondences of the pseudo and T2w MR images. Nevertheless, the focus of this work was not to synthesize MR images that are identical to true MRI as is the focus of works using generational adversarial networks to synthesize CT from MR. Instead, the goal was to augment the ability of deep learning to learn despite limited training sets by leveraging datasets mimicking intensity variations as the real MR images. The present approach improves on the prior GAN-based data augmentation approaches, by explicitly modeling the appearance of structures of interest, namely, the tumors for generating fully automatic and longitudinal segmentation of lung tumors from MRI with access to only a few expert-segmented MRI datasets.

Conclusion

A novel deep learning approach using cross-modality prior was developed to train robust models for MR lung tumor segmentation from small expert-labeled MR datasets. This method overcomes the limitation of learning robust models from small datasets by leveraging information from expert-segmented CT datasets through a cross-modality prior model. This method surpasses state-of-the-art methods in segmentation accuracy and demonstrates initial feasibility in auto-segmentation of lung tumors from MRI.

E. Computing and Network Environment

It may be helpful to describe aspects of the operating environment as well as associated system components (e.g., hardware elements) in connection with the methods and systems described herein in conjunction with Sections A-D. Referring to FIG. 15A, an embodiment of a network environment is depicted. In brief overview, the network environment includes one or more clients 1502a-102n (also generally referred to as local machine(s) 1502, client(s) 1502, client node(s) 1502, client machine(s) 1502, client computer(s) 1502, client device(s) 1502, endpoint(s) 1502, or endpoint node(s) 1502) in communication with one or more servers 1506a-1506n (also generally referred to as server(s) 1506, node 1506, or remote machine(s) 1506) via one or more networks 1504. In some embodiments, a client 1502 has the capacity to function as both a client node seeking access to resources provided by a server and as a server providing access to hosted resources for other clients 1502a-1502n.

Although FIG. 15A shows a network 1504 between the clients 1502 and the servers 1506, the clients 1502 and the servers 1506 may be on the same network 1504. In some embodiments, there are multiple networks 1504 between the clients 1502 and the servers 1506. In one of these embodiments, a network 1504' (not shown) may be a private network and a network 1504 may be a public network. In another of these embodiments, a network 1504 may be a private network and a network 1504' a public network. In still another of these embodiments, networks 1504 and 1504' may both be private networks.

The network 1504 may be connected via wired or wireless links. Wired links may include Digital Subscriber Line (DSL), coaxial cable lines, or optical fiber lines. The wireless links may include BLUETOOTH, Wi-Fi, Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 1504 may be any type and/or form of network. The geographical scope of the network 1504 may vary widely and the network 1504 can be a body area network (BAN), a personal area network (PAN), a local-area network (LAN), e.g. Intranet, a metropolitan area network (MAN), a wide area network (WAN), or the Internet. The topology of the network 1504 may be of any form and may include, e.g., any of the following: point-to-point, bus, star, ring, mesh, or tree. The network 1504 may be an overlay network which is virtual and sits on top of one or more layers of other networks 1504'. The network 1504 may be of any such network topology as known to those ordinarily skilled in the art capable of supporting the operations described herein. The network 1504 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 1504 may be a type of a broadcast network, a telecommunications network, a data communication network, or a computer network.

In some embodiments, the system may include multiple, logically-grouped servers 1506. In one of these embodiments, the logical group of servers may be referred to as a server farm 1538 (not shown) or a machine farm 1538. In another of these embodiments, the servers 1506 may be geographically dispersed. In other embodiments, a machine farm 1538 may be administered as a single entity. In still other embodiments, the machine farm 1538 includes a plurality of machine farms 1538. The servers 1506 within each machine farm 1538 can be heterogeneous—one or more of the servers 1506 or machines 1506 can operate according to one type of operating system platform (e.g., WINDOWS NT, manufactured by Microsoft Corp. of Redmond, Washington), while one or more of the other servers 1506 can operate on according to another type of operating system platform (e.g., Unix, Linux, or Mac OS X).

In one embodiment, servers 1506 in the machine farm 1538 may be stored in high-density rack systems, along with associated storage systems, and located in an enterprise data center. In this embodiment, consolidating the servers 1506 in this way may improve system manageability, data security, the physical security of the system, and system performance by locating servers 1506 and high-performance storage systems on localized high-performance networks. Centralizing the servers 1506 and storage systems and coupling them with advanced system management tools allows more efficient use of server resources.

The servers 1506 of each machine farm 1538 do not need to be physically proximate to another server 1506 in the same machine farm 1538. Thus, the group of servers 1506 logically grouped as a machine farm 1538 may be interconnected using a wide-area network (WAN) connection or a metropolitan-area network (MAN) connection. For example, a machine farm 1538 may include servers 1506 physically located in different continents or different regions of a continent, country, state, city, campus, or room. Data transmission speeds between servers 1506 in the machine farm 1538 can be increased if the servers 1506 are connected using a local-area network (LAN) connection or some form of direct connection. Additionally, a heterogeneous machine farm 1538 may include one or more servers 1506 operating according to a type of operating system, while one or more other servers 1506 execute one or more types of hypervisors rather than operating systems. In these embodiments, hypervisors may be used to emulate virtual hardware, partition physical hardware, virtualize physical hardware, and execute virtual machines that provide access to computing environments, allowing multiple operating systems to run concurrently on a host computer. Native hypervisors may run directly on the host computer. Hypervisors may include VMware ESX/Six, manufactured by VMWare, Inc., of Palo Alto, California; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 1538 may be decentralized. For example, one or more servers 1506 may comprise components, subsystems and modules to support one or more management services for the machine farm 1538. In one of these embodiments, one or more servers 1506 provide functionality for management of dynamic data, including techniques for handling failover, data replication, and increasing the robustness of the machine farm 1538. Each server 1506 may communicate with a persistent store and, in some embodiments, with a dynamic store.

Server 1506 may be a file server, application server, web server, proxy server, appliance, network appliance, gateway, gateway server, virtualization server, deployment server, SSL VPN server, or firewall. In one embodiment, the server 1506 may be referred to as a remote machine or a node. In another embodiment, a plurality of nodes may be in the path between any two communicating servers.

Referring to FIG. 15B, a cloud computing environment is depicted. A cloud computing environment may provide client 1502 with one or more resources provided by a network environment. The cloud computing environment may include one or more clients 1502a-102n, in communication with the cloud 1508 over one or more networks 1504. Clients 1502 may include, e.g., thick clients, thin clients, and zero clients. A thick client may provide at least some functionality even when disconnected from the cloud 1508 or servers 1506. A thin client or a zero client may depend on the connection to the cloud 1508 or server 1506 to provide functionality. A zero client may depend on the cloud 1508 or other networks 1504 or servers 1506 to retrieve operating system data for the client device. The cloud 1508 may include back end platforms, e.g., servers 1506, storage, server farms or data centers.

The cloud 1508 may be public, private, or hybrid. Public clouds may include public servers 1506 that are maintained by third parties to the clients 1502 or the owners of the clients. The servers 1506 may be located off-site in remote geographical locations as disclosed above or otherwise. Public clouds may be connected to the servers 1506 over a public network. Private clouds may include private servers 1506 that are physically maintained by clients 1502 or owners of clients. Private clouds may be connected to the servers 1506 over a private network 1504. Hybrid clouds 1508 may include both the private and public networks 1504 and servers 1506.

The cloud 1508 may also include a cloud-based delivery, e.g. Software as a Service (SaaS) 1510, Platform as a Service (PaaS) 1512, and Infrastructure as a Service (IaaS) 1514. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS include AMAZON WEB SERVICES provided by Amazon.com, Inc., of Seattle, Washington, RACKSPACE CLOUD provided by Rackspace US, Inc., of San Antonio, Texas, Google Compute Engine provided by Google Inc. of Mountain View, California, or RIGHTSCALE provided by RightScale, Inc., of Santa Barbara, California. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Washington, Google App Engine provided by Google Inc., and HEROKU provided by Heroku, Inc. of San Francisco, California. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, California, or OFFICE 365 provided by Microsoft Corporation. Examples of SaaS may also include data storage providers, e.g. DROPBOX provided by Dropbox, Inc. of San Francisco, California, Microsoft SKYDRIVE provided by Microsoft Corporation, Google Drive provided by Google Inc., or Apple ICLOUD provided by Apple Inc. of Cupertino, California.

Clients 1502 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 1502 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 1502 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, California). Clients 1502 may also access SaaS resources through smartphone or tablet applications, including, e.g., Salesforce Sales Cloud, or Google Drive app. Clients 1502 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

The client 1502 and server 1506 may be deployed as and/or executed on any type and form of computing device, e.g., a computer, network device or appliance capable of communicating on any type and form of network and performing the operations described herein. FIGS. 15C and 15D depict block diagrams of a computing device 1500 useful for practicing an embodiment of the client 1502 or a server 1506. As shown in FIGS. 15C and 15D, each computing device 1500 includes a central processing unit 1521, and a main memory unit 1522. As shown in FIG. 15C, a computing device 1500 may include a storage device 1528, an installation device 1516, a network interface 1518, an I/O controller 1523, display devices 1524a-1524n, a keyboard 1526 and a pointing device 1527, e.g., a mouse. The storage device 1528 may include, without limitation, an operating system, software, and a software of an image classification system 1520. As shown in FIG. 15D, each computing device 1500 may also include additional optional elements, e.g., a memory port 1503, a bridge 1540, one or more input/output devices 1530a-1530n (generally referred to using reference numeral 1530), and a cache memory 1540 in communication with the central processing unit 1521.

The central processing unit 1521 is any logic circuitry that responds to and processes instructions fetched from the main memory unit 1522. In many embodiments, the central processing unit 1521 is provided by a microprocessor unit, e.g.: those manufactured by Intel Corporation of Mountain View, California; those manufactured by Motorola Corporation of Schaumburg, Illinois; the ARM processor and TEGRA system on a chip (SoC) manufactured by Nvidia of Santa Clara, California; the POWER7 processor, those manufactured by International Business Machines of White Plains, New York; or those manufactured by Advanced Micro Devices of Sunnyvale, California. The computing device 1500 may be based on any of these processors, or any other processor capable of operating as described herein. The central processing unit 1521 may utilize instruction level parallelism, thread level parallelism, different levels of cache, and multi-core processors. A multi-core processor may include two or more processing units on a single computing component. Examples of a multi-core processors include the AMD PHENOM IIX2, INTEL CORE i5 and INTEL CORE i7.

Main memory unit 1522 may include one or more memory chips capable of storing data and allowing any storage location to be directly accessed by the microprocessor 1521. Main memory unit 1522 may be volatile and faster than storage 1528 memory. Main memory units 1522 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 1522 or the storage 1528 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 1522 may be based on any of the above described memory chips, or any other available memory chips capable of operating as described herein. In the embodiment shown in FIG. 15C, the processor 1521 communicates with main memory 1522 via a system bus 1550 (described in more detail below). FIG. 15D depicts an embodiment of a computing device 1500 in which the processor communicates directly with main memory 1522 via a memory port 1503. For example, in FIG. 15D the main memory 1522 may be DRDRAM.

FIG. 15D depicts an embodiment in which the main processor 1521 communicates directly with cache memory 1540 via a secondary bus, sometimes referred to as a backside bus. In other embodiments, the main processor 1521 communicates with cache memory 1540 using the system bus 1550. Cache memory 1540 typically has a faster response time than main memory 1522 and is typically provided by SRAM, BSRAM, or EDRAM. In the embodiment shown in FIG. 15D, the processor 1521 communicates with various I/O devices 1530 via a local system bus 1550. Various buses may be used to connect the central processing unit 1521 to any of the I/O devices 1530, including a PCI bus, a PCI-X bus, or a PCI-Express bus, or a NuBus. For embodiments in which the I/O device is a video display 1524, the processor 1521 may use an Advanced Graphics Port (AGP) to communicate with the display 1524 or the I/O controller 1523 for the display 1524. FIG. 15D depicts an embodiment of a computer 1500 in which the main processor 1521 communicates directly with I/O device 1530b or other processors 1521' via HYPERTRANSPORT, RAPIDIO, or INFINIBAND communications technology. FIG. 15D also depicts an embodiment in which local busses and direct communication are mixed: the processor 1521 communicates with I/O device 1530a using a local interconnect bus while communicating with I/O device 1530b directly.

A wide variety of I/O devices 1530a-1530n may be present in the computing device 1500. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 1530a-1530n may include a combination of multiple input or output devices, including, e.g., Microsoft KINECT, Nintendo Wiimote for the WII, Nintendo WII U GAMEPAD, or Apple IPHONE. Some devices 1530a-1530n allow gesture recognition inputs through combining some of the inputs and outputs. Some devices 1530a-1530n provides for facial recognition which may be utilized as an input for different purposes including authentication and other commands. Some devices 1530a-1530n provides for voice recognition and inputs, including, e.g., Microsoft KINECT, SIRI for IPHONE by Apple, Google Now or Google Voice Search.

Additional devices 1530a-1530n have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touch-screen devices, including, e.g., Microsoft PIXELSENSE or Multi-Touch Collaboration Wall, may have larger surfaces, such as on a table-top or on a wall, and may also interact with other electronic devices. Some I/O devices 1530a-1530n, display devices 1524a-1524n or group of devices may be augment reality devices. The I/O devices may be controlled by an I/O controller 1523 as shown in FIG. 15C. The I/O controller may control one or more I/O devices, such as, e.g., a keyboard 1526 and a pointing device 1527, e.g., a mouse or optical pen. Furthermore, an I/O device may also provide storage and/or an installation medium 1516 for the computing device 1500. In still other embodiments, the computing device 1500 may provide USB connections (not shown) to receive handheld USB storage devices. In further embodiments, an I/O device 1530 may be a bridge between the system bus 1550 and an external communication bus, e.g., a USB bus, a SCSI bus, a FireWire bus, an Ethernet bus, a Gigabit Ethernet bus, a Fibre Channel bus, or a Thunderbolt bus.

In some embodiments, display devices 1524a-1524n may be connected to I/O controller 1523. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g., stereoscopy, polarization filters, active shutters, or autostereoscopic. Display devices 1524a-1524n may also be a head-mounted display (TIMD). In some embodiments, display devices 1524a-1524n or the corresponding I/O controllers 1523 may be controlled through or have hardware support for OPENGL or DIRECTX API or other graphics libraries.

In some embodiments, the computing device 1500 may include or connect to multiple display devices 1524a-1524n, which each may be of the same or different type and/or form. As such, any of the I/O devices 1530a-1530n and/or the I/O controller 1523 may include any type and/or form of suitable hardware, software, or combination of hardware and software to support, enable or provide for the connection and use of multiple display devices 1524a-1524n by the computing device 1500. For example, the computing device 1500 may include any type and/or form of video adapter, video card, driver, and/or library to interface, communicate, connect or otherwise use the display devices 1524a-1524n. In one embodiment, a video adapter may include multiple connectors to interface to multiple display devices 1524a-1524n. In other embodiments, the computing device 1500 may include multiple video adapters, with each video adapter connected to one or more of the display devices 1524a-1524n. In some embodiments, any portion of the operating system of the computing device 1500 may be configured for using multiple displays 1524a-1524n. In other embodiments, one or more of the display devices 1524a-1524n may be provided by one or more other computing devices 1500a or 1500b connected to the computing device 1500, via the network 1504. In some embodiments software may be designed and constructed to use another computer's display device as a second display device 1524a for the computing device 1500. For example, in one embodiment, an Apple iPad may connect to a computing device 1500 and use the display of the device 1500 as an additional display screen that may be used as an extended desktop. One ordinarily skilled in the art will recognize and appreciate the various ways and embodiments that a computing device 1500 may be configured to have multiple display devices 1524a-1524n.

Referring again to FIG. 15C, the computing device 1500 may comprise a storage device 1528 (e.g. one or more hard disk drives or redundant arrays of independent disks) for storing an operating system or other related software, and for storing application software programs such as any program related to the image classification system software 1520. Examples of storage device 1528 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 1528 may be non-volatile, mutable, or read-only. Some storage device 1528 may be internal and connect to the computing device 1500 via a bus 1550. Some storage device 1528 may be external and connect to the computing device 1500 via a I/O device 1530 that provides an external bus. Some storage device 1528 may connect to the computing device 1500 via the network interface 1518 over a network 1504, including, e.g., the Remote Disk for MACBOOK AIR by Apple. Some client devices 1500 may not require a non-volatile storage device 1528 and may be thin clients or zero clients 1502. Some storage device 1528 may also be used as an installation device 1516, and may be suitable for installing software and programs. Additionally, the operating system and the software can be run from a bootable medium, for example, a bootable CD, e.g., KNOPPIX, a bootable CD for GNU/Linux that is available as a GNU/Linux distribution from knoppix.net.

Client device 1500 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 1502. An application distribution platform may include a repository of applications on a server 1506 or a cloud 1508, which the clients 1502a-102n may access over a network 1504. An application distribution platform may include application developed and provided by various developers. A user of a client device 1502 may select, purchase and/or download an application via the application distribution platform.

Furthermore, the computing device 1500 may include a network interface 1518 to interface to the network 1504 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 1500 communicates with other computing devices 1500' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Florida. The network interface 1518 may comprise a built-in network adapter, network interface card, PCMCIA network card, EXPRESS-CARD network card, card bus network adapter, wireless network adapter, USB network adapter, modem or any other device suitable for interfacing the computing device 1500 to any type of network capable of communication and performing the operations described herein.

A computing device 1500 of the sort depicted in FIGS. 15B and 15C may operate under the control of an operating system, which controls scheduling of tasks and access to system resources. The computing device 1500 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Washington; MAC OS and iOS, manufactured by Apple, Inc. of Cupertino, California; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, California, among others. Some operating systems, including, e.g., the CHROME OS by Google, may be used on zero clients or thin clients, including, e.g., CHROMEBOOKS.

The computer system 1500 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 1500 has sufficient processor power and memory capacity to perform the operations described herein. In some embodiments, the computing device 1500 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 1500 is a gaming system. For example, the computer system 1500 may comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Washington.

In some embodiments, the computing device 1500 is a digital audio player such as the Apple IPOD, IPOD Touch, and IPOD NANO lines of devices, manufactured by Apple Computer of Cupertino, California. Some digital audio players may have other functionality, including, e.g., a gaming system or any functionality made available by an application from a digital application distribution platform. For example, the IPOD Touch may access the Apple App Store. In some embodiments, the computing device 1500 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 1500 is a tablet e.g. the IPAD line of devices by Apple; GALAXY TAB family of devices by Samsung; or KINDLE FIRE, by Amazon.com, Inc. of Seattle, Washington. In other embodiments, the computing device 1500 is an eBook reader, e.g. the KINDLE family of devices by Amazon.com, or NOOK family of devices by Barnes & Noble, Inc. of New York City, New York.

In some embodiments, the communications device 1502 includes a combination of devices, e.g. a smartphone combined with a digital audio player or portable media player. For example, one of these embodiments is a smartphone, e.g., the IPHONE family of smartphones manufactured by Apple, Inc.; a Samsung GALAXY family of smartphones manufactured by Samsung, Inc; or a Motorola DROID family of smartphones. In yet another embodiment, the communications device 1502 is a laptop or desktop computer equipped with a web browser and a microphone and speaker system, e.g. a telephony headset. In these embodiments, the communications devices 1502 are web-enabled and can receive and initiate phone calls. In some embodiments, a laptop or desktop computer is also equipped with a webcam or other video capture device that enables video chat and video call.

In some embodiments, the status of one or more machines 1502, 1506 in the network 1504 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

It should be understood that the systems described above may provide multiple ones of any or each of those components and these components may be provided on either a standalone machine or, in some embodiments, on multiple machines in a distributed system. The systems and methods described above may be implemented as a method, apparatus or article of manufacture using programming and/or engineering techniques to produce software, firmware, hardware, or any combination thereof. In addition, the systems and methods described above may be provided as one or more computer-readable programs embodied on or in one or more articles of manufacture. The term "article of manufacture" as used herein is intended to encompass code or logic accessible from and embedded in one or more computer-readable devices, firmware, programmable logic, memory devices (e.g., EEPROMs, ROMs, PROMs, RAMs, SRAMs, etc.), hardware (e.g., integrated circuit chip, Field Programmable Gate Array (FPGA), Application Specific Integrated Circuit (ASIC), etc.), electronic devices, a computer readable non-volatile storage unit (e.g., CD-ROM, floppy disk, hard disk drive, etc.). The article of manufacture may be accessible from a file server providing access to the computer-readable programs via a network transmission line, wireless transmission media, signals propagating through space, radio waves, infrared signals, etc. The article of manufacture may be a flash memory card or a magnetic tape. The article of manufacture includes hardware logic as well as software or programmable code embedded in a computer readable medium that is executed by a processor. In general, the computer-readable programs may be implemented in any programming language, such as LISP, PERL, C, C++, C#, PROLOG, or in any byte code language such as JAVA. The software programs may be stored on or in one or more articles of manufacture as object code.

While various embodiments of the methods and systems have been described, these embodiments are exemplary and in no way limit the scope of the described methods or systems. Those having skill in the relevant art can effect changes to form and details of the described methods and systems without departing from the broadest scope of the described methods and systems. Thus, the scope of the methods and systems described herein should not be limited by any of the exemplary embodiments and should be defined in accordance with the accompanying claims and their equivalents.

What is claimed is:

1. A method of segmenting biomedical images using multi-resolution residual neural networks, comprising:
receiving, by a computing device having one or more processors, an initial biomedical image derived from a tomographic biomedical imaging scan, the initial biomedical image having a first image resolution;
applying, by the computing device, a segmentation model for biomedical images to the initial biomedical image, the segmentation model comprising a plurality of residual layers, the segmentation model comprising:
a first residual layer to maintain a first residual stream using the initial biomedical image and feature maps from succeeding residual layers, the first residual stream carrying a first plurality of feature maps, the first plurality of feature maps each having the first image resolution;
a second residual layer to maintain a second residual stream using a subset of the first plurality of feature maps of the first residual stream and feature maps from successive residual layers, the second residual stream carrying a second plurality of feature maps to be fed into the first residual stream, the second plurality of feature maps each having a second image resolution lower than the first image resolution; and
a third residual layer to maintain a third residual stream using a subset of feature maps from at least one of the first residual stream or the second residual stream, the third residual stream carrying a third plurality of feature maps to be fed into at least one of the first residual stream and the second residual stream, the third plurality of feature maps each having a third image resolution lower than the first image resolution and the second image resolution, and
generating, by the computing device, a segmented biomedical image using output from the first residual layer of the segmentation model.

2. The method of claim 1, further comprising:
identifying, by the computing device, a labeled tomographic biomedical image for training the segmentation model;
determining, by the computing device, a loss metric between the labeled tomographic biomedical image and the segmented biomedical image, the loss metric indicating at least one difference between the labeled tomographic biomedical image and the segmented biomedical image; and
modifying, by the computing device, at least one parameter of the segmentation model based on the loss metric.

3. The method of claim 1, wherein identifying the initial tomographic biomedical image further comprises identifying the initial tomographic biomedical image of a first modality; and further comprising:
training, by the computing device, the segmentation model using training data in, the training data including a plurality of tomographic biomedical images of the first modality and of a second modality different from the first modality.

4. The method of claim 1, further comprising:
identifying, by the computing device, a plurality of sample feature maps for each residual layer derived from a sample tomographic biomedical image for training the segmentation model;
determining, by the computing device, for each residual layer of the segmentation model, a loss metric between a corresponding plurality of feature maps and a corresponding plurality of sample feature maps; and
modifying, by the computing device, for each residual layer of the segmentation model, at least one parameter of the residual layer based on the loss metric for the residual layer.

5. The method of claim 1, wherein applying the segmentation model further comprises applying the segmentation model comprising a pooling operator to select in accordance to a pooling operation the subset of feature maps from one of the plurality of residual layers for another of the plurality of residual layers,
the third residual layer to maintain the third residual stream using the subset of feature maps from the second residual stream, the third residual stream carrying the third plurality of feature maps to be fed into both the first residual stream and the second residual stream.

6. The method of claim 1, wherein applying the segmentation model further comprises applying the segmentation model comprising:
the first residual layer comprising a set of residual units, a set of aggregator operators, and a convolution operator to process the first plurality of feature maps carried by the first residual stream and at least one of the second plurality of feature maps or the third plurality of feature maps;
the second residual layer comprising a set of residual connection units and a set of aggregator operators to process the second plurality of feature maps carried by the second residual stream, the first plurality of feature maps from the first residual stream, and the third plurality of feature maps from the third residual stream;

the third residual layer comprising a set of residual connection units and a set of aggregator operators to process the third plurality of feature maps carried by the third residual stream and at least one of the first plurality of feature maps from the first residual stream and the second plurality of feature maps from the second residual stream.

7. The method of claim 6, wherein applying the segmentation model further comprises applying the segmentation model comprising:

each layer residual connection units of the third residual layer each having a first number of the residual connection unit of the third residual layer equal to or larger than a second number of each residual connection unit of the second residual layer.

8. The method of claim 1, wherein applying the segmentation model further comprises applying the segmentation model comprising:

the second residual layer comprising a set of residual connection units, a set of aggregator operators, and at least one skip aggregator unit to process the second plurality of feature maps carried by the second residual stream, the at least one skip aggregator unit to combine feature maps outputted by a first residual connection unit of the set and by a second residual connection unit of the set of residual connection units.

9. The method of claim 1, wherein generating the segmented biomedical image further comprises generating the segmented biomedical image by combining outputs from the plurality of residual layers of different image resolutions.

10. The method of claim 1, further comprising using, by the computing device, the segmented biomedical image to determine a health metric of a subject from which the initial segmented biomedical is acquired.

11. A system for segmenting biomedical images using multi-resolution residual neural networks, comprising:

a computing device having one or more processors, configured to:

receive an initial biomedical image derived from a tomographic biomedical imaging scan, the initial biomedical image having a first image resolution;

apply a segmentation model for biomedical images to the initial biomedical image, the segmentation model comprising a plurality of residual layers, the segmentation model comprising:

a first residual layer to maintain a first residual stream using the initial biomedical image and feature maps from succeeding residual layers, the first residual stream carrying a first plurality of feature maps, the first plurality of feature maps each having the first image resolution;

a second residual layer to maintain a second residual stream using a subset of the first plurality of feature maps of the first residual stream and feature maps from successive residual layers, the second residual stream carrying a second plurality of feature maps to be fed into the first residual stream, the second plurality of feature maps each having a second image resolution lower than the first image resolution; and a third residual layer to maintain a third residual stream using a subset of feature maps from at least one of the first residual stream or the second residual stream, the third residual stream carrying a third plurality of feature maps to be fed into at least one of the first residual stream and the second residual stream, the third plurality of feature maps each having a third image resolution lower than the first image resolution and the second image resolution, and generate a segmented biomedical image using output from the first residual layer of the segmentation model.

12. The system of claim 11, wherein the computing device is further configured to:

identify a labeled tomographic biomedical image for training the segmentation model;

determine a loss metric between the labeled tomographic biomedical image and the segmented biomedical image, the loss metric indicating at least one difference between the labeled tomographic biomedical image and the segmented biomedical image; and modify at least one parameter of the segmentation model based on the loss metric.

13. The system of claim 11, wherein the computing device is further configured to:

identify the initial tomographic biomedical image of a first modality;

train the segmentation model using training data in, the training data including a plurality of tomographic biomedical images of the first modality and of a second modality different from the first modality.

14. The system of claim 11, wherein the computing device is further configured to:

identify a plurality of sample feature maps for each residual layer derived from a sample tomographic biomedical image for training the segmentation model;

determine, for each residual layer of the segmentation model, a loss metric between a corresponding plurality of feature maps and a corresponding plurality of sample feature maps; and modify, for each residual layer of the segmentation model, at least one parameter of the residual layer based on the loss metric for the residual layer.

15. The system of claim 11, wherein the segmentation model further comprises:

a pooling operator to select in accordance to a pooling operation the subset of feature maps from one of the plurality of residual layers for another of the plurality of residual layers.

16. The system of claim 11, wherein the first residual layer further comprises a set of residual units, a set of aggregator operators, and a convolution operator to process the first plurality of feature maps carried by the first residual stream and at least one of the second plurality of feature maps or the third plurality of feature maps;

wherein the second residual layer further comprises a set of residual connection units and a set of aggregator operators to process the second plurality of feature maps carried by the second residual stream, the first plurality of feature maps from the first residual stream, and the third plurality of feature maps from the third residual stream;

wherein the third residual layer further comprises a set of residual connection units and a set of aggregator operators to process the third plurality of feature maps carried by the third residual stream and at least one of the first plurality of feature maps from the first residual stream and the second plurality of feature maps from the second residual stream.

17. The system of claim 16, wherein each layer residual connection units of the third residual layer each having a first number of the residual connection unit of the third residual layer equal to or larger than a second number of each residual connection unit of the second residual layer.

18. The system of claim 11, wherein the second residual layer further comprises a set of residual connection units, a set of aggregator operators, and at least one skip aggregator unit to process the second plurality of feature maps carried by the second residual stream, the at least one skip aggregator unit to combine feature maps outputted by a first residual connection unit of the set and by a second residual connection unit of the set of residual connection units.

19. The system of claim 11, wherein the computing device is further configured to generate the segmented biomedical image by combining outputs from the plurality of residual layers of different image resolutions.

20. The system of claim 11, wherein the computing device is further configured to use the segmented biomedical image to determine a health metric of a subject from which the initial segmented biomedical is acquired.

* * * * *